(12) United States Patent (10) Patent No.: US 8,163,901 B2
Duncton et al. (45) Date of Patent: Apr. 24, 2012

(54) AMIDE DERIVATIVES AS ION-CHANNEL LIGANDS AND PHARMACEUTICAL COMPOSITIONS AND METHODS OF USING THE SAME

(75) Inventors: Matthew Duncton, San Bruno, CA (US); Donogh John Roger O'Mahony, San Mateo, CA (US); Matthew Cox, San Francisco, CA (US); Maria De Los Angeles Estiarte-Martinez, San Francisco, CA (US)

(73) Assignee: Evotec AG, Hamburg (DE)

( * ) Notice: Subject to any disclaimer, the term of this patent is extended or adjusted under 35 U.S.C. 154(b) by 0 days.

(21) Appl. No.: 12/811,972

(22) PCT Filed: Jan. 9, 2009

(86) PCT No.: PCT/US2009/000150
§ 371 (c)(1),
(2), (4) Date: Oct. 12, 2010

(87) PCT Pub. No.: WO2009/089057
PCT Pub. Date: Jul. 16, 2009

(65) Prior Publication Data
US 2011/0028465 A1 Feb. 3, 2011

Related U.S. Application Data

(60) Provisional application No. 61/010,542, filed on Jan. 9, 2008, provisional application No. 61/124,240, filed on Apr. 14, 2008.

(51) Int. Cl.
| C07D 407/12 | (2006.01) |
| C07D 513/04 | (2006.01) |
| C07D 401/12 | (2006.01) |
| C07D 491/052 | (2006.01) |
| C07D 498/04 | (2006.01) |
| A61K 31/4709 | (2006.01) |

(52) U.S. Cl. .......... 544/91; 544/105; 546/114; 546/115; 546/167; 548/362.5; 514/230.5; 514/301; 514/302; 514/314; 514/406

(58) Field of Classification Search ........................ None
See application file for complete search history.

(56) References Cited

FOREIGN PATENT DOCUMENTS
| EP | 1632477 A | 3/2006 |
| WO | WO 2006/072736 A | 7/2006 |
| WO | WO 2007/109160 A | 9/2007 |
| WO | WO 2007/133637 A | 11/2007 |
| WO | WO 2008/007211 A | 1/2008 |
| WO | WO 2008/090434 A | 7/2008 |

OTHER PUBLICATIONS

Koo, John, et al., "Derivatives of 1,-4 Benzodioxan. I. 1,4 Benzodioxan-2-carboxamides," Journal of the American Chemical Society, vol. 77, No. 20, 1955, pp. 5373-5375.

*Primary Examiner* — Janet Andres
*Assistant Examiner* — Timothy R Rozof
(74) *Attorney, Agent, or Firm* — Klauber & Jackson LLC

(57) ABSTRACT

Compounds are disclosed that have a formula represented by the following:

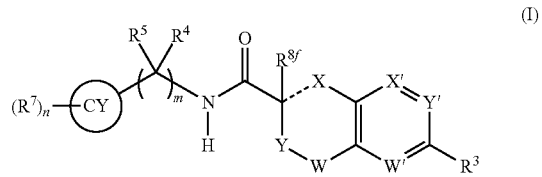

(I)

The compounds may be prepared as pharmaceutical compositions, and may be used for the prevention and treatment of a variety of conditions in mammals including humans, including by way of non-limiting example, pain, inflammation, traumatic injury, and others.

5 Claims, No Drawings

AMIDE DERIVATIVES AS ION-CHANNEL LIGANDS AND PHARMACEUTICAL COMPOSITIONS AND METHODS OF USING THE SAME

CROSS REFERENCE TO RELATED APPLICATIONS

The present application is a National Stage Application claiming the priority of co-pending PCT Application No. PCT/US2009/000150 filed Jan. 9, 2009, which in turn, claims priority from U.S. Provisional application Ser. No. 61/010,542, filed Jan. 9, 2008, and Provisional application Ser. No. 61/124,240, filed Apr. 14, 2008. Applicants claim the benefits of 35 U.S.C. §120 as to the PCT application and priority under 35 U.S.C. §119 as to the said U.S. Provisional applications, and the entire disclosures of all applications are incorporated herein by reference in their entireties.

FIELD OF THE INVENTION

This invention relates to novel compounds and to pharmaceutical compositions containing such compounds. This invention also relates to methods for preventing and/or treating pain and inflammation-related conditions in mammals, such as (but not limited to) arthritis, Parkinson's disease, Alzheimer's disease, stroke, uveitis, asthma, myocardial infarction, the treatment and prophylaxis of pain syndromes (acute and chronic or neuropathic), traumatic brain injury, acute spinal cord injury, neurodegenerative disorders, alopecia (hair loss), inflammatory bowel disease, urinary incontinence, chronic obstructive pulmonary disease, irritable bowel disease, osteoarthritis, and autoimmune disorders, using the compounds and pharmaceutical compositions of the invention.

BACKGROUND OF THE INVENTION

Studies of signaling pathways in the body have revealed the existence of ion channels and sought to explain their role. Ion channels are integral membrane proteins with two distinctive characteristics: they are gated (open and closed) by specific signals such as membrane voltage or the direct binding of chemical ligands and, once open, they conduct ions across the cell membrane at very high rates.

There are many types of ion channels. Based on their selectivity to ions, they can be divided into calcium channel, potassium channel, sodium channel, etc. The calcium channel is more permeable to calcium ions than other types of ions, the potassium channel selects potassium ions over other ions, and so forth. Ion channels may also be classified according to their gating mechanisms. In a voltage-gated ion channel, the opening probability depends on the membrane voltage, whereas in a ligand-gated ion channel, the opening probability is regulated by the binding of small molecules (the ligands). Since ligand-gated ion channels receive signals from the ligand, they may also be considered as "receptors" for ligands.

Examples of ligand-gated ion channels include nAChR (nicotinic acetylcholine receptor) channel, GluR (glutamate receptor) channel, ATP-sensitive potassium channel, G-protein activated channel, cyclic-nucleotide-gated channel, etc.

Transient receptor potential (TRP) channel proteins constitute a large and diverse family of proteins that are expressed in many tissues and cell types. This family of channels mediates responses to nerve growth factors, pheromones, olfaction, tone of blood vessels and metabolic stress et al., and the channels are found in a variety of organisms, tissues and cell types including nonexcitable, smooth muscle and neuronal cells. Furthermore, TRP-related channel proteins are implicated in several diseases, such as several tumors and neuro-degenerative disorders and the like. See, for example, Minke, et al., *APStracts* 9:0006P (2002).

Nociceptors are specialized primary afferent neurons and the first cells in a series of neurons that lead to the sensation of pain. The receptors in these cells can be activated by different noxious chemical or physical stimuli. The essential functions of nociceptors include the transduction of noxious stimuli into depolarizations that trigger action potentials, conduction of action potentials from primary sensory sites to synapses in the central nervous system, and conversion of action potentials into neurotransmitter release at presynaptic terminals, all of which depend on ion channels.

One TRP channel protein of particular interest is the vanilloid receptor. Also known as VR1, the vanilloid receptor is a non-selective cation channel which is activated or sensitized by a series of different stimuli including capsaicin, heat and acid stimulation and products of lipid bilayer metabolism (anandamide), and lipoxygenase metabolites. See, for example Smith, et al., *Nature*, 418:186-190 (2002). VR1 does not discriminate among monovalent cations, however, it exhibits a notable preference for divalent cations with a permeability sequence of $Ca^{2+}>Mg^{2+}>Na^+=K^+=Cs^+$. $Ca^{2+}$ is especially important to VR1 function, as extracellular $Ca^{2+}$ mediates desensitization, a process which enables a neuron to adapt to specific stimuli by diminishing its overall response to a particular chemical or physical signal. VR1 is highly expressed in primary sensory neurons in rats, mice and humans, and innervates many visceral organs including the dermis, bones, bladder, gastrointestinal tract and lungs. It is also expressed in other neuronal and non-neuronal tissues including the CNS, nuclei, kidney, stomach and T-cells. The VR1 channel is a member of the superfamily of ion channels with six membrane-spanning domains, with highest homology to the TRP family of ion channels.

VR1 gene knockout mice have been shown to have reduced sensory sensitivity to thermal and acid stimuli. See, for example, Caterina, et al. *Science*, 14:306-313 (2000). This supports the concept that VR1 contributes not only to generation of pain responses but also to the maintenance of basal activity of sensory nerves. VR1 agonists and antagonists have use as analgesics for the treatment of pain of various genesis or etiology, for example acute, inflammatory and neuropathic pain, dental pain and headache (such as migraine, cluster headache and tension headache). They are also useful as anti-inflammatory agents for the treatment of arthritis, Parkinson's Disease, Alzheimer's Disease, stroke, uveitis, asthma, myocardial infarction, the treatment and prophylaxis of pain syndromes (acute and chronic [neuropathic]), traumatic brain injury, spinal cord injury, neurodegenerative disorders, alopecia (hair loss), inflammatory bowel disease, irritable bowel disease and autoimmune disorders, renal disorders, obesity, eating disorders, cancer, schizophrenia, epilepsy, sleeping disorders, cognition, depression, anxiety, blood pressure, lipid disorders, osteoarthritis, and atherosclerosis.

Compounds, such as those of the present invention, which interact with the vanilloid receptor can thus play a role in treating or preventing or ameliorating these conditions.

A wide variety of Vanilloid compounds of different structures are known in the art, for example those disclosed in European Patent Application Numbers, EP 0 347 000 and EP 0 401 903, UK Patent Application Number GB 2226313 and International Patent Application, Publication Number WO 92/09285. Particularly notable examples of vanilloid compounds or vanilloid receptor modulators are capsaicin or trans 8-methyl-N-vanillyl-6-nonenamide which is isolated from the pepper plant, capsazepine (Tetrahedron, 53, 1997, 4791) and olvanil or —N-(4-hydroxy-3-methoxybenzyl)oleamide (J. Med. Chem., 36, 1993, 2595).

International Patent Application, Publication Number WO 02/08221 discloses diaryl piperazine and related compounds which bind with high selectivity and high affinity to vanilloid receptors, especially Type I Vanilloid receptors, also known as capsaicin or VR1 receptors. The compounds are said to be useful in the treatment of chronic and acute pain conditions, itch and urinary incontinence.

International Patent Application, Publication Numbers WO 02/16317, WO 02/16318 and WO 02/16319 suggest that compounds having a high affinity for the vanilloid receptor are useful for treating stomach-duodenal ulcers.

International Patent Application, Publication No. WO 2005/046683, published May 26, 2005, commonly owned, discloses a series of compounds that have demonstrated activity as VR-1 antagonists, and that are suggested as being useful for the treatment of conditions associated with VR-1 activity.

U.S. Pat. No. 3,424,760 and U.S. Pat. No. 3,424,761 both describe a series of 3-Ureidopyrrolidines that are said to exhibit analgesic, central nervous system, and psychopharmacologic activities. These patents specifically disclose the compounds 1-(1-phenyl-3-pyrrolidinyl)-3-phenyl urea and 1-(1-phenyl-3-pyrrolidinyl)-3-(4-methoxyphenyl)urea respectively. International Patent Applications, Publication Numbers WO 01/62737 and WO 00/69849 disclose a series of pyrazole derivatives which are stated to be useful in the treatment of disorders and diseases associated with the NPY receptor subtype Y5, such as obesity. WO 01/62737 specifically discloses the compound 5-amino-N-isoquinolin-5-yl-1-[3-(trifluoromethyl)phenyl]-1H-pyrazole-3-carboxamide. WO 00/69849 specifically discloses the compounds 5-methyl-N-quinolin-8-yl-1-[3-(trifluoromethyl)phenyl]-1H-pyrazole-3-carboxamide, 5-methyl-N-quinolin-7-yl-1-[3-trifluoromethyl)phenyl]-1H-pyrazole-3-carboxamide, 5-methyl-N-quinolin-3-yl-1-[3-(trifluoromethyl)phenyl]-1H-pyrazole-3-carboxamide, N-isoquinolin-5-yl-5-methyl-1-[3-(trifluoromethyl)phenyl]-1H-pyrazole-3-carboxamide, 5-methyl-N-quinolin-5-yl-1-[3-(trifluoromethyl)phenyl]-1H-pyrazole-3-carboxamide, 1-(3-chlorophenyl)-N-isoquinolin-5-yl-5-methyl-1H-pyrazole-3-carboxamide, N-isoquinolin-5-yl-1-(3-methoxyphenyl)-5-methyl-1H-pyrazole-3-carboxamide, 1-(3-fluorophenyl)-N-isoquinolin-5-yl-5-methyl-1H-pyrazole-3-carboxamide, 1-(2-chloro-5-trifluoromethylphenyl)-N-isoquinolin-5-yl-5-methyl-1N-pyrazole-3-carboxamide, 5-methyl-N-(3-methylisoquinolin-5-yl)-1-[3-(trifluoromethyl)phenyl]-1N-pyrazole-3-carboxamide, 5-methyl-N-(1,2,3,4-tetrahydroisoquinolin-5-yl)-1-[3-(trifluoromethyl)phenyl]-1H-pyrazole-3-carboxamide.

German Patent Application Number 2502588 describes a series of piperazine derivatives. This application specifically discloses the compound N-[3-[2-(diethylamino) ethyl]-1,2-dihydro-4-methyl-2-oxo-7-quinolinyl]-4-phenyl-1-piperazinecarboxamide.

International Patent Application, Publication No. WO 05/003084 discloses 4-(methylsulfonylamino) phenyl analogs as vanilloid antagonists and their use as analgesics, and International Patent Application Publication No. WO02/16318 discloses thiourea derivatives as a modulator for vanilloid receptor and their use as analgesics.

It has now been discovered that certain compounds have surprising potency and selectivity as VR-1 antagonists. The compounds of the present invention are considered to be particularly beneficial as VR-1 antagonists as certain compounds exhibit improved aqueous solubility and metabolic stability.

SUMMARY OF THE INVENTION

It has now been found that compounds such as those set forth herein, are capable of modifying mammalian ion channels such as the VR1 cation channel. Accordingly, the present compounds are potent VR1 antagonists with analgesic activity by systemic administration. The compounds of the present invention may show less toxicity, good absorption, good half-life, good solubility, low protein binding affinity, less drug-drug interaction, a reduced inhibitory activity at the HERG channel, reduced QT prolongation and good metabolic stability. This finding leads to novel compounds having therapeutic value. It also leads to pharmaceutical compositions having the compounds of the present invention as active ingredients and to their use to treat, prevent or ameliorate a range of conditions in mammals such as but not limited to pain of various genesis or etiology, for example acute, chronic, inflammatory and neuropathic pain, dental pain and headache (such as migraine, cluster headache and tension headache).

Accordingly, in a first aspect of the invention, compounds are disclosed that are capable of modifying ion channels, in vivo, having a formula I:

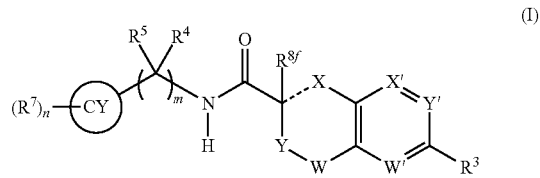

or a pharmaceutically acceptable salt thereof, and isotopic variants thereof, stereoisomers and tautomers thereof, wherein:

CY is bicycloheteroaryl;
W represents O, $CR^{8a}R^{8b}$, or $NR^{8c}$;
X represents N, O, $CR^{8a}$, $CR^{8a}R^{8b}$, or $NR^{8c}$;
Y represents $CR^{8d}R^{8e}$;
W', X', and Y' each independently represent $CR^8$ or N; provided that all three of W', X' and Y' can not be N at the same time;
$R^3$ represents hydrogen, halogen, hydroxy, substituted or unsubstituted ($C_1$-$C_6$)alkyl, substituted or unsubstituted ($C_1$-$C_6$)alkoxy or substituted or unsubstituted 3-8 membered cycloalkyl;
$R^4$ and $R^5$ each independently represent hydrogen or substituted or unsubstituted ($C_1$-$C_6$)alkyl; m is 0 or 1;
each $R^7$ is H, halogen, hydroxy, ($C_1$-$C_6$)acyl, cyano, substituted or unsubstituted ($C_1$-$C_6$)alkyl, or substituted or unsubstituted ($C_1$-$C_6$)alkoxy; or $R^7$ is ($C_1$-$C_6$)alkyl, halo ($C_1$-$C_6$)alkyl, hydroxy($C_1$-$C_6$)alkyl, ($C_1$-$C_6$)alkoxy, hydroxy($C_1$-$C_6$)alkoxy, halo($C_1$-$C_6$)alkoxy; n is 1, 2, 3, 4 or 5;
each $R^8$ independently represents hydrogen, halogen, hydroxy, cyano, substituted or unsubstituted ($C_1$-$C_6$) alkyl, substituted or unsubstituted ($C_1$-$C_6$)alkoxy, or substituted or unsubstituted 3-8 membered cycloalkyl;
each $R^{8a}$, $R^{8b}$, $R^{8d}$, $R^{8e}$ and $R^{8f}$ independently represents hydrogen, halo, hydroxy, substituted or unsubstituted ($C_1$-$C_6$)alkyl, or substituted or unsubstituted 3-8 membered cycloalkyl;

$R^{8c}$ represents hydrogen, or substituted or unsubstituted $(C_1-C_6)$alkyl; and the dotted bond represents a single or a double bond;

provided that:

i) when the dotted bond is a double bond, then $R^{8f}$ is absent;

ii) when X is N or O; then $R^{8f}$ is H or substituted or unsubstituted alkyl;

iii) when X is O; then W is O or $NR^{8c}$; and iv) when W is O; and the dotted bond is a single bond; then X is O or $NR^{8c}$.

In one particular embodiment, with respect to compounds of formula I, the dotted bond is a single bond.

In one particular embodiment, with respect to compounds of formula I, the dotted bond is a double bond.

In one particular embodiment, with respect to compounds of formula I, m is 0.

In one particular embodiment, with respect to compounds of formula I, m is 1.

The compounds of the present invention are useful for the treatment of inflammatory pain and associated hyperalgesia and allodynia. They are also useful for the treatment of neuropathic pain and associated hyperalgesia and allodynia (e.g. trigeminal or herpetic neuralgia, diabetic neuropathy, causalgia, sympathetically maintained pain and deafferentation syndromes such as brachial plexus avulsion). The compounds of the present invention are also useful as anti-inflammatory agents for the treatment of arthritis, and as agents to treat Parkinson's Disease, Alzheimer's Disease, stroke, uveitis, asthma, myocardial infarction, traumatic brain injury, spinal cord injury, neurodegenerative disorders, alopecia (hair loss), inflammatory bowel disease and autoimmune disorders, renal disorders, obesity, eating disorders, cancer, schizophrenia, epilepsy, sleeping disorders, cognition, depression, anxiety, blood pressure, lipid disorders, and atherosclerosis.

In one aspect, this invention provides compounds which are capable of modifying ion channels, in vivo. Representative ion channels so modified include voltage-gated channels and ligand-gated channels, including cation channels such as vanilloid channels.

In a further aspect, the present invention provides pharmaceutical compositions comprising a compound of the invention, and a pharmaceutical carrier, excipient or diluent. In this aspect of the invention, the pharmaceutical composition can comprise one or more of the compounds described herein.

In a further aspect of the invention, a method is disclosed for treating mammals, including humans, as well as lower mammalian species, susceptible to or afflicted with a condition from among those listed herein, and particularly, such condition as may be associated with e.g. arthritis, uveitis, asthma, myocardial infarction, traumatic brain injury, acute spinal cord injury, alopecia (hair loss), inflammatory bowel disease and autoimmune disorders, which method comprises administering an effective amount of one or more of the compounds or the pharmaceutical compositions described above and herein.

In yet another method of treatment aspect, this invention provides a method of treating a mammal susceptible to or afflicted with a condition that gives rise to pain responses or that relates to imbalances in the maintenance of basal activity of sensory nerves. Compounds have use as analgesics for the treatment of pain of various geneses or etiology, for example acute, inflammatory pain (such as pain associated with osteoarthritis and rheumatoid arthritis); various neuropathic pain syndromes (such as post-herpetic neuralgia, trigeminal neuralgia, reflex sympathetic dystrophy, diabetic neuropathy, Guillian Barre syndrome, fibromyalgia, phantom limb pain, post-mastectomy pain, peripheral neuropathy, HIV neuropathy, and chemotherapy-induced and other iatrogenic neuropathies); visceral pain, (such as that associated with gastroesophageal reflex disease, irritable bowel syndrome, inflammatory bowel disease, pancreatitis, and various gynecological and urological disorders), dental pain and headache (such as migraine, cluster headache and tension headache).

In additional method of treatment aspects, this invention provides methods of treating a mammal susceptible to or afflicted with neurodegenerative diseases and disorders such as, for example Parkinson's disease, Alzheimer's disease and multiple sclerosis; diseases and disorders which are mediated by or result in neuroinflammation such as, for example traumatic brain injury, stroke, and encephalitis; centrally-mediated neuropsychiatric diseases and disorders such as, for example depression mania, bipolar disease, anxiety, schizophrenia, eating disorders, sleep disorders and cognition disorders; epilepsy and seizure disorders; prostate, bladder and bowel dysfunction such as, for example urinary incontinence, urinary hesitancy, rectal hypersensitivity, fecal incontinence, benign prostatic hypertrophy and inflammatory bowel disease; irritable bowel syndrome, over active bladder, respiratory and airway disease and disorders such as, for example, allergic rhinitis, asthma and reactive airway disease and chronic obstructive pulmonary disease; diseases and disorders which are mediated by or result in inflammation such as, for example rheumatoid arthritis and osteoarthritis, myocardial infarction, various autoimmune diseases and disorders, uveitis and atherosclerosis; itch/pruritus such as, for example psoriasis; alopecia (hair loss); obesity; lipid disorders; cancer; blood pressure; spinal cord injury; and renal disorders; which methods comprise administering an effective condition-treating or condition-preventing amount of one or more of the pharmaceutical compositions just described.

In addition to the methods of treatment set forth above, the present invention extends to the use of any of the compounds of the invention for the preparation of medicaments that may be administered for such treatments, as well as to such compounds for use in the treatments disclosed and specified.

In additional aspects, this invention provides methods for synthesizing the compounds of the invention, with representative synthetic protocols and pathways disclosed later on herein.

Other objects and advantages will become apparent to those skilled in the art from a consideration of the ensuing detailed description.

DETAILED DESCRIPTION OF THE PREFERRED EMBODIMENTS

Definitions

The following terms are intended to have the meanings presented therewith below and are useful in understanding the description and intended scope of the present invention.

When describing the invention, which may include compounds, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein.

The articles "a" and "an" may be used herein to refer to one or to more than one (i.e. at least one) of the grammatical objects of the article. By way of example "an analogue" means one analogue or more than one analogue.

'Acyl' or 'Alkanoyl' refers to a radical —C(O)R$^{20}$, where R$^{20}$ is hydrogen, C$_1$-C$_8$ alkyl, C$_3$-C$_{10}$ cycloalkyl, C$_3$-C$_{10}$ cycloalkylmethyl, 4-10 membered heterocycloalkyl, aryl, arylalkyl, 5-10 membered heteroaryl or heteroarylalkyl as defined herein. Representative examples include, but are not limited to, formyl, acetyl, cyclohexylcarbonyl, cyclohexylmethylcarbonyl, benzoyl and benzylcarbonyl. Exemplary 'acyl' groups are —C(O)H, —C(O)—C$_1$-C$_8$ alkyl, —C(O)—(CH$_2$)$_t$(C$_6$-C$_{10}$ aryl), —C(O)—(CH$_2$)$_t$(5-10 membered heteroaryl), —C(O)—(CH$_2$)$_t$(C$_3$-C$_{10}$ cycloalkyl), and —C(O)—(CH$_2$)$_t$(4-10 membered heterocycloalkyl), wherein t is an integer from 0 to 4.

'Substituted Acyl' or 'Substituted Alkanoyl' refers to a radical —C(O)R$^{21}$, wherein R$^{21}$ is independently
  C$_1$-C$_8$ alkyl, substituted with halo or hydroxy; or
  C$_3$-C$_{10}$ cycloalkyl, 4-10 membered heterocycloalkyl, C$_6$-C$_{10}$ aryl, arylalkyl, 5-10 membered heteroaryl or heteroarylalkyl, each of which is substituted with unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

'Acylamino' refers to a radical —NR$^{22}$C(O)R$^{23}$, where R$^{22}$ is hydrogen, C$_1$-C$_8$ alkyl, C$_3$-C$_{10}$ cycloalkyl, 4-10 membered heterocycloalkyl, C$_6$-C$_{10}$ aryl, arylalkyl, 5-10 membered heteroaryl or heteroarylalkyl and R$^{23}$ is hydrogen, C$_1$-C$_8$ alkyl, C$_3$-C$_{10}$ cycloalkyl, 4-10 membered heterocycloalkyl, C$_6$-C$_{10}$ aryl, arylalkyl, 5-10 membered heteroaryl or heteroarylalkyl, as defined herein. Exemplary 'acylamino' include, but are not limited to, formylamino, acetylamino, cyclohexylcarbonylamino, cyclohexylmethyl-carbonylamino, benzoylamino and benzylcarbonylamino. Exemplary 'acylamino' groups are —NR$^{21'}$C(O)—C$_1$-C$_8$ alkyl, —NR$^{21'}$C(O)—(CH$_2$)$_t$(C$_6$-C$_{10}$ aryl), groups are —NR$^{21'}$C(O)—(CH$_2$)$_t$(5-10 membered heteroaryl), —NR$^{21'}$C(O)—(CH$_2$)$_t$(C$_3$-C$_{10}$ cycloalkyl), and —NR$^{21'}$C(O)—(CH$_2$)$_t$(4-10 membered heterocycloalkyl), wherein t is an integer from 0 to 4, each R$^{21'}$ independently represents H or C$_1$-C$_8$ alkyl.

'Substituted Acylamino' refers to a radical —NR$^{24}$C(O)R$^{25}$, wherein:
  R$^{24}$ is independently
  H, C$_1$-C$_8$ alkyl, substituted with halo or hydroxy; or
  C$_3$-C$_{10}$ cycloalkyl, 4-10 membered heterocycloalkyl, C$_6$-C$_{10}$ aryl, arylalkyl, 5-10 membered heteroaryl or heteroarylalkyl, each of which is substituted with unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy; and
  R$^{25}$ is independently
  H, C$_1$-C$_8$ alkyl, substituted with halo or hydroxy; or
  C$_3$-C$_{10}$ cycloalkyl, 4-10 membered heterocycloalkyl, C$_6$-C$_{10}$ aryl, arylalkyl, 5-10 membered heteroaryl or heteroarylalkyl, each of which is substituted with unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxyl;
  provided that at least one of R$^{24}$ and R$^{25}$ is other than H.

'Alkoxy' refers to the group —OR$^{26}$ where R$^{26}$ is C$_1$-C$_8$ alkyl. Particular alkoxy groups are methoxy, ethoxy, n-propoxy, isopropoxy, n-butoxy, tert-butoxy, sec-butoxy, n-pentoxy, n-hexoxy, and 1,2-dimethylbutoxy. Particular alkoxy groups are lower alkoxy, i.e. with between 1 and 6 carbon atoms. Further particular alkoxy groups have between 1 and 4 carbon atoms.

'Substituted alkoxy' refers to an alkoxy group substituted with one or more of those groups recited in the definition of "substituted" herein, and particularly refers to an alkoxy group having 1 or more substituents, for instance from 1 to 5 substituents, and particularly from 1 to 3 substituents, in particular 1 substituent, selected from the group consisting of amino, substituted amino, C$_6$-C$_{10}$ aryl, —O-Aryl, carboxyl, cyano, C$_3$-C$_{10}$ cycloalkyl, 4-10 membered heterocycloalkyl, halogen, 5-10 membered heteroaryl, hydroxyl, nitro, thioalkoxy, thio-O-aryl, thiol, alkyl-S(O)—, aryl-S(O)—, alkyl-S(O)$_2$— and aryl-S(O)$_2$—. Exemplary 'substituted alkoxy' groups are —O—(CH$_2$)$_t$(C$_6$-C$_{10}$ aryl), —O—(CH$_2$)$_t$(5-10 membered heteroaryl), —O—(CH$_2$)$_t$(C$_3$-C$_{10}$ cycloalkyl), and —O—(CH$_2$)$_t$(4-10 membered heterocycloalkyl), wherein t is an integer from 0 to 4 and any aryl, heteroaryl, cycloalkyl or heterocycloalkyl groups present, may themselves be substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy. Particular exemplary 'substituted alkoxy' groups are OCF$_3$, OCH$_2$CF$_3$, OCH$_2$Ph, OCH$_2$-cyclopropyl, OCH$_2$CH$_2$OH, and OCH$_2$CH$_2$NMe$_2$.

'Alkoxycarbonyl' refers to a radical —C(O)—OR$^{27}$ where R$^{27}$ represents an C$_1$-C$_8$ alkyl, C$_3$-C$_{10}$ cycloalkyl, C$_3$-C$_{10}$ cycloalkylalkyl, 4-10 membered heterocycloalkylalkyl, aralkyl, or 5-10 membered heteroarylalkyl as defined herein. Exemplary "alkoxycarbonyl" groups are C(O)O—C$_1$-C$_8$ alkyl, —C(O)O—(CH$_2$)$_t$(C$_6$-C$_{10}$ aryl), —C(O)O—(CH$_2$)$_t$(5-10 membered heteroaryl), —C(O)O—(CH$_2$)$_t$(C$_3$-C$_{10}$ cycloalkyl), and —C(O)O—(CH$_2$)$_t$(4-10 membered heterocycloalkyl), wherein t is an integer from 1 to 4.

'Substituted Alkoxycarbonyl' refers to a radical —C(O)—OR$^{28}$ where R$^{28}$ represents:
  C$_1$-C$_8$ alkyl, C$_3$-C$_{10}$ cycloalkyl, C$_3$-C$_{10}$ cycloalkylalkyl, or 4-10 membered heterocycloalkylalkyl, each of which is substituted with halo, substituted or unsubstituted amino, or hydroxy; or
  C$_6$-C$_{10}$ aralkyl, or 5-10 membered heteroarylalkyl, each of which is substituted with unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxyl.

'O-Aryl-carbonyl' refers to a radical —C(O)—OR$^{29}$ where R$^{29}$ represents an C$_6$-C$_{10}$ aryl, as defined herein. Exemplary "O-Aryl-carbonyl" groups is —C(O)O—(C$_6$-C$_{10}$ aryl).

'Substituted O-Aryl-carbonyl' refers to a radical —C(O)—OR$^{30}$ where R$^{30}$ represents a
  C$_6$-C$_{10}$ aryl, substituted with unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxyl.

'Hetero-O-Aryl-carbonyl' refers to a radical —C(O)—OR$^{31}$ where R$^{31}$ represents a 5-10 membered heteroaryl, as defined herein.

'Substituted Hetero-O-Aryl-carbonyl' refers to a radical —C(O)—OR$^{32}$ where R$^{32}$ represents a:
  5-10 membered heteroaryl, substituted with unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxyl.

'Alkyl' means straight or branched aliphatic hydrocarbon having 1 to 20 carbon atoms. Particular alkyl has 1 to 12 carbon atoms. More particular is lower alkyl which has 1 to 6 carbon atoms. A further particular group has 1 to 4 carbon atoms. Exemplary straight chained groups include methyl, ethyl n-propyl, and n-butyl. Branched means that one or more lower alkyl groups such as methyl, ethyl, propyl or butyl is attached to a linear alkyl chain, exemplary branched chain groups include isopropyl, iso-butyl, t-butyl and isoamyl.

'Substituted alkyl' refers to an alkyl group as defined above substituted with one or more of those groups recited in the definition of "substituted" herein, and particularly refers to an alkyl group having 1 or more substituents, for instance from 1 to 5 substituents, and particularly from 1 to 3 substituents, in particular 1 substituent, selected from the group consisting of acyl, acylamino, acyloxy (—O-acyl or —OC(O)$R^{20}$), alkoxy, alkoxycarbonyl, alkoxycarbonylamino (—NR"-alkoxycarbonyl or —NH—C(O)—$OR^{27}$), amino, substituted amino, aminocarbonyl (carbamoyl or amido or —C(O)—NR"$_2$), aminocarbonylamino (—NR"—C(O)—NR"$_2$), aminocarbonyloxy (—O—C(O)—NR"$_2$), aminosulfonyl, sulfonylamino, aryl, aryloxy, azido, carboxyl, cyano, cycloalkyl, halogen, hydroxy, heteroaryl, nitro, thiol, —S-alkyl, —S-aryl, —S(O)-alkyl, —S(O)-aryl, —S(O)$_2$-alkyl, and —S(O)$_2$- aryl. In a particular embodiment 'substituted alkyl' refers to a $C_1$-$C_8$ alkyl group substituted with halo, cyano, nitro, trifluoromethyl, trifluoromethoxy, azido, —NR'''$SO_2$R''', —$SO_2$NR''R''', —C(O)R''', —C(O)OR''', —OC(O)R''', —NR'''C(O)R''', —C(O)NR'''R''', —NR'''R''', or —(CR'''R''')$_m$OR'''; wherein each R' is independently selected from H, $C_1$-$C_8$ alkyl, —(CH$_2$)$_t$($C_6$-$C_{10}$ aryl), —(CH$_2$)$_t$(5-10 membered heteroaryl), —(CH$_2$)$_t$($C_3$-$C_{10}$ cycloalkyl), and —(CH$_2$)$_t$(4-10 membered heterocycloalkyl), wherein t is an integer from 0 to 4 and any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. Each of R''' and R'''' independently represents H or $C_1$-$C_8$ alkyl.

'Amino' refers to the radical —$NH_2$.

'Substituted amino' refers to an amino group substituted with one or more of those groups recited in the definition of 'substituted' herein, and particularly refers to the group —N($R^{33}$)$_2$ where each $R^{33}$ is independently selected from:
hydrogen, $C_1$-$C_8$ alkyl, $C_6$-$C_{10}$ aryl, 5-10 membered heteroaryl, 4-10 membered heterocycloalkyl, or $C_3$-$C_{10}$ cycloalkyl; or
$C_1$-$C_8$ alkyl, substituted with halo or hydroxy; or
—(CH$_2$)$_t$($C_6$-$C_{10}$ aryl), —(CH$_2$)$_t$(5-10 membered heteroaryl), —(CH$_2$)$_t$($C_3$-$C_{10}$ cycloalkyl) or —(CH$_2$)$_t$(4-10 membered heterocycloalkyl) wherein t is an integer between 0 and 8, each of which is substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy; or
both $R^{33}$ groups are joined to form an alkylene group.
When both $R^{33}$ groups are hydrogen, —N($R^{33}$)$_2$ is an amino group. Exemplary 'substituted amino' groups are —$NR^{33'}$—$C_1$-$C_8$ alkyl, —$NR^{33'}$—(CH$_2$)$_t$($C_6$-$C_{10}$ aryl), —$NR^{33'}$—(CH$_2$)$_t$(5-10 membered heteroaryl), —$NR^{33'}$—(CH$_2$)$_t$($C_3$-$C_{10}$ cycloalkyl), and —$NR^{33'}$—(CH$_2$)$_t$(4-10 membered heterocycloalkyl), wherein t is an integer from 0 to 4, each $R^{33'}$ independently represents H or $C_1$-$C_8$ alkyl; and any alkyl groups present, may themselves be substituted by halo, substituted or unsubstituted amino, or hydroxy; and any aryl, heteroaryl, cycloalkyl or heterocycloalkyl groups present, may be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. For the avoidance of doubt, the term "substituted amino" includes the groups alkylamino, substituted alkylamino, alkylarylamino, substituted alkylarylamino, arylamino, substituted arylamino, dialkylamino and substituted dialkylamino as defined below.

'Alkylamino' refers to the group —$NHR^{34}$, wherein $R^{34}$ is $C_1$-$C_8$ alkyl. 'Substituted Alkylamino' refers to the group —$NHR^{35}$, wherein $R^{35}$ is $C_1$-$C_8$ alkyl; and the alkyl group is substituted with halo, substituted or unsubstituted amino, hydroxy, $C_3$-$C_{10}$ cycloalkyl, 4-10 membered heterocycloalkyl, $C_6$-$C_{10}$ aryl, 5-10 membered heteroaryl, aralkyl or heteroaralkyl; and any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

'Alkylarylamino' refers to the group —$NR^{36}R^{37}$, wherein $R^{36}$ is $C_6$-$C_{10}$ aryl and $R^{37}$ is $C_1$-$C_8$ alkyl.

'Substituted Alkylarylamino' refers to the group —$NR^{38}R^{39}$, wherein $R^{38}$ is $C_6$-$C_{10}$ aryl and $R^{39}$ is $C_1$-$C_8$ alkyl; and the alkyl group is substituted with halo, substituted or unsubstituted amino, hydroxy, $C_3$-$C_{10}$ cycloalkyl, 4-10 membered heterocycloalkyl, $C_6$-$C_{10}$ aryl, 5-10 membered heteroaryl, aralkyl or heteroaralkyl; and any aryl, heteroaryl, cycloalkyl or heterocycloalkyl groups present, may themselves be substituted by unsubstituted $C_1$-$C_4$ alkyl, halo, cyano, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

'Arylamino' means a radical —$NHR^{40}$ where $R^{40}$ is selected from $C_6$-$C_{10}$ aryl and 5-10 membered heteroaryl as defined herein.

'Substituted Arylamino' refers to the group —$NHR^{41}$, wherein $R^{41}$ is independently selected from $C_6$-$C_{10}$ aryl and 5-10 membered heteroaryl; and any aryl or heteroaryl groups present, may themselves be substituted by unsubstituted $C_1$-$C_4$ alkyl, halo, cyano, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

'Dialkylamino' refers to the group —$NR^{42}R^{43}$, wherein each of $R^{42}$ and $R^{43}$ are independently selected from $C_1$-$C_8$ alkyl.

'Substituted Dialkylamino' refers to the group —$NR^{44}R^{45}$, wherein each of $R^{44}$ and $R^{45}$ are independently selected from $C_1$-$C_8$ alkyl; and the alkyl group is independently substituted with halo, hydroxy, $C_3$-$C_{10}$ cycloalkyl, 4-10 membered heterocycloalkyl, $C_6$-$C_{10}$ aryl, 5-10 membered heteroaryl, aralkyl or heteroaralkyl; and any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_{1-4}$ haloalkyl, unsubstituted $C_1$-$C_4$ hydroxyalkyl, or unsubstituted $C_1$-$C_4$ haloalkoxy or hydroxy.

'Diarylamino' refers to the group —$NR^{46}R^{47}$, wherein each of $R^{46}$ and $R^{47}$ are independently selected from $C_6$-$C_{10}$ aryl.

'Aminosulfonyl' or 'Sulfonamide' refers to the radical —$S(O_2)NH_2$.

'Substituted aminosulfonyl' or 'substituted sulfonamide' refers to a radical such as —$S(O_2)N(R^{48})_2$ wherein each $R^{48}$ is independently selected from:
H, $C_1$-$C_8$ alkyl, $C_3$-$C_{10}$ cycloalkyl, 4-10 membered heterocycloalkyl, $C_6$-$C_{10}$ aryl, aralkyl, 5-10 membered heteroaryl, and heteroaralkyl; or
$C_1$-$C_8$ alkyl substituted with halo or hydroxy; or $C_3$-$C_{10}$ cycloalkyl, 4-10 membered heterocycloalkyl, $C_6$-$C_{10}$ aryl, aralkyl, 5-10 membered heteroaryl, or heteroaralkyl, substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy;

provided that at least one $R^{48}$ is other than H.

Exemplary 'substituted aminosulfonyl' or 'substituted sulfonamide' groups are —S(O$_2$)N(R$^{48'}$)—$C_1$-$C_8$ alkyl, —S(O$_2$)N(R$^{48'}$)—(CH$_2$)$_t$($C_6$-$C_{10}$ aryl), —S(O$_2$)N(R$^{48'}$)—(CH$_2$)$_t$(5-10 membered heteroaryl), —S(O$_2$)N(R$^{48'}$)—(CH$_2$)$_t$($C_3$-$C_{10}$ cycloalkyl), and —S(O$_2$)N(R$^{48'}$)—(CH$_2$)$_t$(4-10 membered heterocycloalkyl), wherein t is an integer from 0 to 4; each $R^{48'}$ independently represents H or $C_1$-$C_8$ alkyl; and any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

'Aralkyl' or 'arylalkyl' refers to an alkyl group, as defined above, substituted with one or more aryl groups, as defined above. Particular aralkyl or arylalkyl groups are alkyl groups substituted with one aryl group.

'Substituted Aralkyl' or 'substituted arylalkyl' refers to an alkyl group, as defined above, substituted with one or more aryl groups; and at least one of any aryl group present, may themselves be substituted by unsubstituted $C_1$-$C_4$ alkyl, halo, cyano, unsubstituted $C_1$-$C_4$ alkoxy, unsubstituted $C_1$-$C_4$ haloalkyl, unsubstituted $C_1$-$C_4$ hydroxyalkyl, or unsubstituted haloalkoxy or hydroxy.

'Aryl' refers to a monovalent aromatic hydrocarbon group derived by the removal of one hydrogen atom from a single carbon atom of a parent aromatic ring system. In particular aryl refers to an aromatic ring structure, mono-cyclic or polycyclic that includes from 5 to 12 ring members, more usually 6 to 10. Where the aryl group is a monocyclic ring system it preferentially contains 6 carbon atoms. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene and trinaphthalene. Particularly aryl groups include phenyl, naphthyl, indenyl, and tetrahydronaphthyl.

'Substituted Aryl' refers to an aryl group substituted with one or more of those groups recited in the definition of 'substituted' herein, and particularly refers to an aryl group that may optionally be substituted with 1 or more substituents, for instance from 1 to 5 substituents, particularly 1 to 3 substituents, in particular 1 substituent. Particularly, 'Substituted Aryl' refers to an aryl group substituted with one or more of groups selected from halo, $C_1$-$C_8$ alkyl, $C_1$-$C_8$ haloalkyl, $C_1$-$C_8$ haloalkoxy, cyano, hydroxy, $C_1$-$C_8$ alkoxy, and amino. Examples of representative substituted aryls include the following

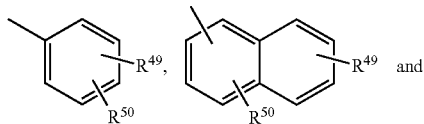

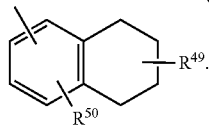

In these formulae one of $R^{49}$ and $R^{50}$ may be hydrogen and at least one of $R^{49}$ and $R^{50}$ is each independently selected from $C_1$-$C_8$ alkyl, 4-10 membered heterocycloalkyl, alkanoyl, $C_1$-$C_8$ alkoxy, heteroO-Aryl, alkylamino, arylamino, heteroarylamino, NR$^{51}$COR$^{52}$, NR$^{51}$SOR$^{52}$NR$^{51}$SO$_2$R$^{52}$, COOalkyl, COOaryl, CONR$^{51}$R$^{52}$, CONR$^{51}$R$^{52}$, NR$^{51}$R$^{52}$, SO$_2$NR$^{51}$R$^{52}$, S-alkyl, SOalkyl, SO$_2$alkyl, Saryl, SOaryl, SO$_2$aryl; or $R^{49}$ and $R^{50}$ may be joined to form a cyclic ring (saturated or unsaturated) from 5 to 8 atoms, optionally containing one or more heteroatoms selected from the group N, O or S. $R^{51}$, and $R^{52}$ are independently hydrogen, $C_1$-$C_8$ alkyl, $C_1$-$C_4$ haloalkyl, $C_3$-$C_{10}$ cycloalkyl, 4-10 membered heterocycloalkyl, $C_6$-$C_{10}$ aryl, substituted aryl, 5-10 membered heteroaryl.

'Arylalkyloxy' refers to an —O-alkylaryl radical where alkylaryl is as defined herein. 'Substituted Arylalkyloxy' refers to an —O-alkylaryl radical where alkylaryl is as defined herein; and any aryl groups present, may themselves be substituted by unsubstituted $C_1$-$C_4$ alkyl, halo, cyano, unsubstituted $C_1$-$C_4$ alkoxy, unsubstituted $C_{1-4}$ haloalkyl, unsubstituted $C_1$-$C_4$ hydroxyalkyl, or unsubstituted $C_1$-$C_4$ haloalkoxy or hydroxy.

'Azido' refers to the radical —N$_3$.

'Carbamoyl or amido' refers to the radical —C(O)NH$_2$.

'Substituted Carbamoyl or substituted amido' refers to the radical —C(O)N(R$^{53}$)$_2$ wherein each $R^{53}$ is independently
   H, $C_1$-$C_8$ alkyl, $C_3$-$C_{10}$ cycloalkyl, 4-10 membered heterocycloalkyl, $C_6$-$C_{10}$ aryl, aralkyl, 5-10 membered heteroaryl, and heteroaralkyl; or
   $C_1$-$C_8$ alkyl substituted with halo or hydroxy; or
   $C_3$-$C_{10}$ cycloalkyl, 4-10 membered heterocycloalkyl, $C_6$-$C_{10}$ aryl, aralkyl, 5-10 membered heteroaryl, or heteroaralkyl, each of which is substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy;
   provided that at least one $R^{53}$ is other than H.

Exemplary 'Substituted Amido/Carbamoyl' groups are —C(O)NR$^{53'}$-$C_1$-$C_8$ alkyl, —C(O)NR$^{53'}$-(CH$_2$)$_t$($C_6$-$C_{10}$ aryl), —C(O)N$^{53'}$—(CH$_2$)$_t$(5-10 membered heteroaryl), —C(O)NR$^{53'}$—(CH$_2$)$_t$($C_3$-$C_{10}$ cycloalkyl), and —C(O)NR$^{53'}$—(CH$_2$)$_t$(4-10 membered heterocycloalkyl), wherein t is an integer from 0 to 4, each $R^{53'}$ independently represents H or $C_1$-$C_8$ alkyl and any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

'Carboxy' refers to the radical —C(O)OH.

'Cycloalkyl' refers to cyclic non-aromatic hydrocarbyl groups having from 3 to 10 carbon atoms. Such cycloalkyl groups include, by way of example, single ring structures such as cyclopropyl, cyclobutyl, cyclopentyl, cyclohexyl, cycloheptyl, and cyclooctyl.

'Substituted cycloalkyl' refers to a cycloalkyl group as defined above substituted with one or more of those groups recited in the definition of 'substituted' herein, and particularly refers to a cycloalkyl group having 1 or more substituents, for instance from 1 to 5 substituents, and particularly from 1 to 3 substituents, in particular 1 substituent 'Cyano' refers to the radical —CN.

'Halo' or 'halogen' refers to fluoro (F), chloro (Cl), bromo (Br) and iodo (I). Particular halo groups are either fluoro or chloro.

'Hetero' when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g. heteroalkyl, cycloalkyl, e.g. heterocycloalkyl, aryl, e.g. heteroaryl, cycloalkenyl, e.g. cycloheteroalkenyl, and the like having from 1 to 5, and particularly from 1 to 3 heteroatoms.

'Heteroaryl' means an aromatic ring structure, mono-cyclic or polycyclic, that includes one or more heteroatoms and 5 to 12 ring members, more usually 5 to 10 ring members. The heteroaryl group can be, for example, a five membered or six membered monocyclic ring or a bicyclic structure formed from fused five and six membered rings or two fused six membered rings or, by way of a further example, two fused five membered rings. Each ring may contain up to four heteroatoms typically selected from nitrogen, sulphur and oxygen. Typically the heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five. Examples of five membered monocyclic heteroaryl groups include but are not limited to pyrrole, furan, thiophene, imidazole, furazan, oxazole, oxadiazole, oxatriazole, isoxazole, thiazole, isothiazole, pyrazole, triazole and tetrazole groups. Examples of six membered monocyclic heteroaryl groups include but are not limited to pyridine, pyrazine, pyridazine, pyrimidine and triazine. Particular examples of bicyclic heteroaryl groups containing a five membered ring fused to another five membered ring include but are not limited to imidazothiazole and imidazoimidazole. Particular examples of bicyclic heteroaryl groups containing a six membered ring fused to a five membered ring include but are not limited to benzofuran, benzothiophene, benzimidazole, benzoxazole, isobenzoxazole, benzisoxazole, benzthiazole, benzisothiazole, isobenzofuran, indole, isoindole, isoindolone, indolizine, indoline, isoindoline, purine (e.g., adenine, guanine), indazole, pyrazolopyrimidine, triazolopyrimidine, benzodioxole and pyrazolopyridine groups. Particular examples of bicyclic heteroaryl groups containing two fused six membered rings include but are not limited to quinoline, isoquinoline, chroman, thiochroman, chromene, isochromene, chroman, isochroman, benzodioxan, quinolizine, benzoxazine, benzodiazine, pyridopyridine, quinoxaline, quinazoline, cinnoline, phthalazine, naphthyridine and pteridine groups. Particular heteroaryl groups are those derived from thiophene, pyrrole, benzothiophene, benzofuran, indole, pyridine, quinoline, imidazole, oxazole and pyrazine.

Examples of representative aryl having hetero atoms containing substitution include the following:

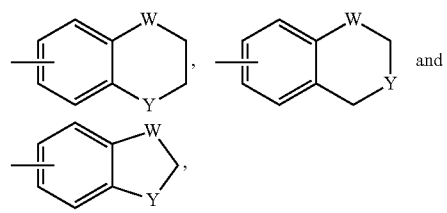

wherein each W is selected from $C(R^{54})_2$, $NR^{54}$, O and S; and each Y is selected from carbonyl, $NR^{54}$, O and S; and $R^{54}$ is independently hydrogen, $C_1$-$C_8$ alkyl, $C_3$-$C_{10}$ cycloalkyl, 4-10 membered heterocycloalkyl, $C_6$-$C_{10}$ aryl, and 5-10 membered heteroaryl.

Examples of representative heteroaryls include the following:

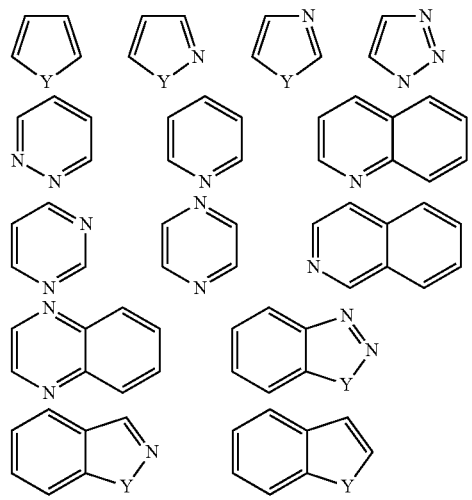

wherein each Y is selected from carbonyl, N, $NR^{55}$, O and S; and $R^{55}$ is independently hydrogen, $C_1$-$C_8$ alkyl, $C_3$-$C_{10}$ cycloalkyl, 4-10 membered heterocycloalkyl, $C_6$-$C_{10}$ aryl, and 5-10 membered heteroaryl.

As used herein, the term 'heterocycloalkyl' refers to a 4-10 membered, stable heterocyclic non-aromatic ring and/or including rings containing one or more heteroatoms independently selected from N, O and S, fused thereto. A fused heterocyclic ring system may include carbocyclic rings and need only include one heterocyclic ring. Examples of heterocyclic rings include, but are not limited to, morpholine, piperidine (e.g. 1-piperidinyl, 2-piperidinyl, 3-piperidinyl and 4-piperidinyl), pyrrolidine (e.g. 1-pyrrolidinyl, 2-pyrrolidinyl and 3-pyrrolidinyl), pyrrolidone, pyran (2H-pyran or 4H-pyran), dihydrothiophene, dihydropyran, dihydrofuran, dihydrothiazole, tetrahydrofuran, tetrahydrothiophene, dioxane, tetrahydropyran (e.g. 4-tetrahydro pyranyl), imidazoline, imidazolidinone, oxazoline, thiazoline, 2-pyrazoline, pyrazolidine, piperazine, and N-alkyl piperazines such as N-methyl piperazine. Further examples include thiomorpholine and its S-oxide and S,S-dioxide (particularly thiomorpholine). Still further examples include azetidine, piperidone, piperazone, and N-alkyl piperidines such as N-methyl piperidine. Particular examples of heterocycloalkyl groups are shown in the following illustrative examples:

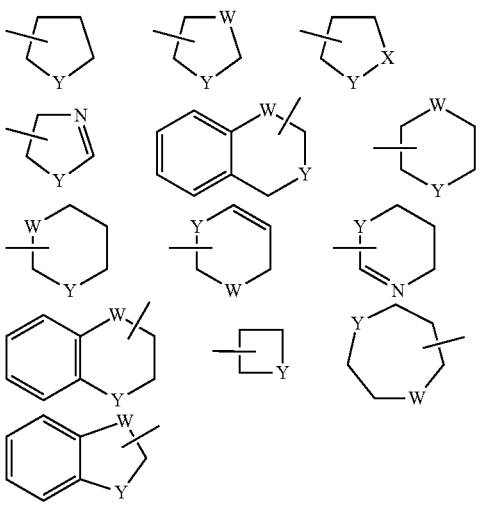

wherein each W is selected from CR$^{56}$, C(R$^{56}$)$_2$, NR$^{56}$, O and S; and each Y is selected from NR$^{56}$, O and S; and R$^{56}$ is independently hydrogen, C$_1$-C$_8$ alkyl, C$_3$-C$_{10}$ cycloalkyl, 4-10 membered heterocycloalkyl, C$_6$-C$_{10}$ aryl, 5-10 membered heteroaryl, These heterocycloalkyl rings may be optionally substituted with one or more groups selected from the group consisting of acyl, acylamino, acyloxy (—O-acyl or —OC(O)R$^{20}$), alkoxy, alkoxycarbonyl, alkoxycarbonylamino (—NR"-alkoxycarbonyl or —NH—C(O)—OR$^{27}$), amino, substituted amino, aminocarbonyl (amido or —C(O)—NR"$_2$), aminocarbonylamino (—NR"—C(O)—NR"$_2$), aminocarbonyloxy (—O—C(O)—NR"$_2$), aminosulfonyl, sulfonylamino, aryl, —O-Aryl, azido, carboxyl, cyano, cycloalkyl, halogen, hydroxy, nitro, thiol, —S-alkyl, —S-aryl, —S(O)-alkyl, —S(O)-aryl, —S(O)$_2$-alkyl, and —S(O)$_2$-aryl. Substituting groups include carbonyl or thiocarbonyl which provide, for example, lactam and urea derivatives.

'Hydroxy' refers to the radical —OH.

'Nitro' refers to the radical —NO$_2$.

'Substituted' refers to a group in which one or more hydrogen atoms are each independently replaced with the same or different substituent(s). Typical substituents may be selected from the group consisting of:

halogen, —R$^{57}$, —O$^-$, =O, —OR", —SR$^{57}$, —S$^-$, =S, —NR$^{57}$R$^{58}$, =NR$^{57}$, —CCl$_3$, —CF$_3$, —CN, —OCN, —SCN, —NO, —NO$_2$, =N$_2$, —N$_3$, —S(O)$_2$O$^-$, —S(O)$_2$OH, —S(O)$_2$R$^{57}$, —OS(O$_2$)O$^-$, —OS(O)$_2$R$^{57}$, —P(O)(O$^-$)$_2$, —P(O)(OR$^{57}$)(O$^-$), —OP(O)(OR$^{57}$)(OR$^{58}$), —C(O)R$^{57}$, —C(S)R$^{57}$, —C(O)OR$^{57}$, —C(O)NR$^{57}$, —C(O)NR$^{57}$R$^{58}$, —C(O)O$^-$, —C(S)OR$^{57}$, —NR$^{59}$C(O)NR$^{57}$R$^{58}$, —NR$^{59}$C(S)NR$^{57}$R$^{58}$, —NR$^{60}$C(NR$^{59}$)NR$^{57}$R$^{58}$ and —C(NR$^{59}$)NR$^{57}$R$^{58}$;

wherein each R$^{57}$, R$^{58}$, R$^{59}$ and R$^{60}$ are independently:
hydrogen, C$_1$-C$_8$ alkyl, C$_6$-C$_{10}$ aryl, arylalkyl, C$_3$-C$_{10}$ cycloalkyl, 4-10 membered heterocycloalkyl, 5-10 membered heteroaryl, heteroarylalkyl; or C$_1$-C$_8$ alkyl substituted with halo or hydroxy; or C$_6$-C$_{10}$ aryl, 5-10 membered heteroaryl, C$_6$-C$_{10}$ cycloalkyl or 4-10 membered heterocycloalkyl substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

In a particular embodiment, substituted groups are substituted with one or more substituents, particularly with 1 to 3 substituents, in particular with one substituent group.

In a further particular embodiment the substituent group or groups are selected from: halo, cyano, nitro, trifluoromethyl, trifluoromethoxy, azido, —NR'''SO$_2$R''', —SO$_2$NR''R''', —C(O)R'', —C(O)OR'', —OC(O)R'', —NR'''C(O)R'', —C(O)NR''R''', —NR''R''', —(CR'''R''')$_m$OR''', wherein each R'' is independently selected from H, C$_1$-C$_8$ alkyl, —(CH$_2$)$_t$(C$_6$-C$_{10}$ aryl), —(CH$_2$)$_t$(5-10 membered heteroaryl), —(CH$_2$)$_t$(C$_3$-C$_{10}$ cycloalkyl), and —(CH$_2$)$_t$(4-10 membered heterocycloalkyl), wherein t is an integer from 0 to 4; and any alkyl groups present, may themselves be substituted by halo or hydroxy; and any aryl, heteroaryl, cycloalkyl or heterocycloalkyl groups present, may themselves be substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

Each R''' independently represents H or C$_1$-C$_6$alkyl.

'Substituted sulfanyl' refers to the group —SR$^{61}$, wherein R$^{61}$ is selected from:

C$_1$-C$_8$ alkyl, C$_3$-C$_{10}$ cycloalkyl, 4-10 membered heterocycloalkyl, C$_6$-C$_{10}$ aryl, aralkyl, 5-10 membered heteroaryl, and heteroaralkyl; or C$_1$-C$_8$ alkyl substituted with halo, substituted or unsubstituted amino, or hydroxy; or C$_3$-C$_{10}$ cycloalkyl, 4-10 membered heterocycloalkyl, C$_6$-C$_{10}$ aryl, aralkyl, 5-10 membered heteroaryl, or heteroaralkyl, each of which is substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

Exemplary 'substituted sulfanyl' groups are —S—(C$_1$-C$_8$ alkyl) and —S—(C$_3$-C$_{10}$ cycloalkyl), —S—(CH$_2$)$_t$(C$_6$-C$_{10}$ aryl), —S—(CH$_2$)$_t$(5-10 membered heteroaryl), —S—(CH$_2$)$_t$ (C$_3$-C$_{10}$ cycloalkyl), and —S—(CH$_2$)$_t$(4-10 membered heterocycloalkyl), wherein t is an integer from 0 to 4 and any aryl, heteroaryl, cycloalkyl or heterocycloalkyl groups present, may themselves be substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy. The term 'substituted sulfanyl' includes the groups 'alkylsulfanyl' or 'alkylthio', 'substituted alkylthio' or 'substituted alkylsulfanyl', 'cycloalkylsulfanyl' or 'cycloalkylthio', 'substituted cycloalkylsulfanyl' or 'substituted cycloalkylthio', 'arylsulfanyl' or 'arylthio' and 'heteroarylsulfanyl' or 'heteroarylthio' as defined below.

'Alkylthio' or 'Alkylsulfanyl' refers to a radical —SR$^{62}$ where R$^{62}$ is a C$_1$-C$_8$ alkyl or group as defined herein. Representative examples include, but are not limited to, methylthio, ethylthio, propylthio and butylthio.

'Substituted Alkylthio' or 'substituted alkylsulfanyl' refers to the group —SR$^{63}$ where R$^{63}$ is a C$_1$-C$_8$ alkyl, substituted with halo, substituted or unsubstituted amino, or hydroxy.

'Cycloalkylthio' or 'Cycloalkylsulfanyl' refers to a radical —SR$^{64}$ where R$^{64}$ is a C$_3$-C$_{10}$ cycloalkyl or group as defined herein. Representative examples include, but are not limited to, cyclopropylthio, cyclohexylthio, and cyclopentylthio.

'Substituted cycloalkylthio' or 'substituted cycloalkylsulfanyl' refers to the group —SR$^{65}$ where R$^{65}$ is a C$_3$-C$_{10}$ cycloalkyl, substituted with halo, substituted or unsubstituted amino, or hydroxy.

'Arylthio' or 'Arylsulfanyl' refers to a radical —SR$^{66}$ where R$^{66}$ is a C$_6$-C$_{10}$ aryl group as defined herein.

'Heteroarylthio' or 'Heteroarylsulfanyl' refers to a radical —SR$^{67}$ where R$^{67}$ is a 5-10 membered heteroaryl group as defined herein.

'Substituted sulfinyl' refers to the group —S(O)R$^{68}$, wherein R$^{68}$ is selected from:
- C$_1$-C$_8$ alkyl, C$_3$-C$_{10}$ cycloalkyl, 4-10 membered heterocycloalkyl, C$_6$-C$_{10}$ aryl, aralkyl, 5-10 membered heteroaryl, and heteroaralkyl; or
- C$_1$-C$_8$ alkyl substituted with halo, substituted or unsubstituted amino, or hydroxy; or
- C$_3$-C$_{10}$ cycloalkyl, 4-10 membered heterocycloalkyl, C$_6$-C$_{10}$ aryl, aralkyl, 5-10 membered heteroaryl, or heteroaralkyl, substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

Exemplary 'substituted sulfinyl' groups are —S(O)—(C$_1$-C$_8$ alkyl) and —S(O)—(C$_3$-C$_{10}$ cycloalkyl), —S(O)—(CH$_2$)$_t$(C$_6$-C$_{10}$ aryl), —S(O)—(CH$_2$)$_t$(5-10 membered heteroaryl), —S(O)—(CH$_2$)$_t$(C$_3$-C$_{10}$ cycloalkyl), and —S(O)—(CH$_2$)$_t$(4-10 membered heterocycloalkyl), wherein t is an integer from 0 to 4 and any aryl, heteroaryl, cycloalkyl or heterocycloalkyl groups present, may themselves be substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy. The term substituted sulfinyl includes the groups 'alkylsulfinyl', 'substituted alkylsulfinyl', 'cycloalkylsulfinyl', 'substituted cycloalkylsulfinyl', 'arylsulfinyl' and 'heteroarylsulfinyl' as defined herein.

'Alkylsulfinyl' refers to a radical —S(O)R$^{69}$ where R$^{69}$ is a C$_1$-C$_8$ alkyl group as defined herein. Representative examples include, but are not limited to, methylsulfinyl, ethylsulfinyl, propylsulfinyl and butylsulfinyl.

'Substituted Alkylsulfinyl' refers to a radical —S(O)R$^{70}$ where R$^{70}$ is a C$_1$-C$_8$ alkyl group as defined herein, substituted with halo, substituted or unsubstituted amino, or hydroxy.

'Cycloalkylsulfinyl' refers to a radical —S(O)R$^{71}$ where R$^{71}$ is a C$_3$-C$_{10}$ cycloalkyl or group as defined herein. Representative examples include, but are not limited to, cyclopropylsulfinyl, cyclohexylsulfinyl, and cyclopentylsulfinyl.

'Substituted cycloalkylsulfinyl' refers to the group —S(O)R$^{72}$ where R$^{72}$ is a C$_3$-C$_{10}$ cycloalkyl, substituted with halo, substituted or unsubstituted amino, or hydroxy.

'Arylsulfinyl' refers to a radical —S(O)R$^{73}$ where R$^{73}$ is a C$_6$-C$_{10}$ aryl group as defined herein.

'Heteroarylsulfinyl' refers to a radical —S(O)R$^{74}$ where R$^{74}$ is a 5-10 membered heteroaryl group as defined herein.

'Substituted sulfonyl' refers to the group —S(O)$_2$R$^{75}$, wherein R$^{75}$ is selected from:
- C$_1$-C$_8$ alkyl, C$_3$-C$_{10}$ cycloalkyl, 4-10 membered heterocycloalkyl, C$_6$-C$_{10}$ aryl, aralkyl, 5-10 membered heteroaryl, and heteroaralkyl; or
- C$_1$-C$_8$ alkyl substituted with halo, substituted or unsubstituted amino, or hydroxy; or
- C$_3$-C$_{10}$ cycloalkyl, 4-10 membered heterocycloalkyl, C$_6$-C$_{10}$ aryl, aralkyl, 5-10 membered heteroaryl, or heteroaralkyl, each of which is substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

Exemplary 'substituted sulfonyl' groups are —S(O)$_2$—(C$_1$-C$_8$ alkyl) and —S(O)$_2$—(C$_3$-C$_{10}$ cycloalkyl), —S(O)$_2$—(CH$_2$)$_t$(C$_6$-C$_{10}$ aryl), —S(O)$_2$—(CH$_2$)$_t$(5-10 membered heteroaryl), —S(O)$_2$—(CH$_2$)$_t$(C$_3$-C$_{10}$ cycloalkyl), and —S(O)$_2$—(CH$_2$)$_t$(4-10 membered heterocycloalkyl), wherein t is an integer from 0 to 4 and any aryl, heteroaryl, cycloalkyl or heterocycloalkyl groups present, may themselves be substituted by unsubstituted C$_1$-C$_4$ alkyl, halo, unsubstituted C$_1$-C$_4$ alkoxy, unsubstituted C$_1$-C$_4$ hydroxyalkyl, or unsubstituted C$_1$-C$_4$ haloalkoxy or hydroxy. The term substituted sulfonyl includes the groups alkylsulfonyl, substituted alkylsulfonyl, cycloalkylsulfonyl, substituted cycloalkylsulfonyl, arylsulfonyl and heteroarylsulfonyl.

'Alkylsulfonyl' refers to a radical —S(O)$_2$R$^{76}$ where R$^{76}$ is an C$_1$-C$_8$ alkyl group as defined herein. Representative examples include, but are not limited to, methylsulfonyl, ethylsulfonyl, propylsulfonyl and butylsulfonyl.

'Substituted Alkylsulfonyl' refers to a radical —S(O)$_2$R$^{77}$ where R$^{77}$ is an C$_1$-C$_8$ alkyl group as defined herein, substituted with halo, substituted or unsubstituted amino, or hydroxy.

'Cycloalkylsulfonyl' refers to a radical —S(O)$_2$R$^{78}$ where R$^{78}$ is a C$_3$-C$_{10}$ cycloalkyl or group as defined herein. Representative examples include, but are not limited to, cyclopropylsulfonyl, cyclohexylsulfonyl, and cyclopentylsulfonyl.

'Substituted cycloalkylsulfonyl' refers to the group —S(O)$_2$ R$^{79}$ where R$^{79}$ is a C$_3$-C$_{10}$ cycloalkyl, substituted with halo, substituted or unsubstituted amino, or hydroxy.

'Arylsulfonyl' refers to a radical —S(O)$_2$R$^{80}$ where R$^{80}$ is an C$_6$-C$_{10}$ aryl group as defined herein.

'Heteroarylsulfonyl' refers to a radical —S(O)$_2$R$^{81}$ where R$^{81}$ is an 5-10 membered heteroaryl group as defined herein.

'Sulfo' or 'sulfonic acid' refers to a radical such as —SO$_3$H.

'Substituted sulfo' or 'sulfonic acid ester' refers to the group —S(O)$_2$OR$^{82}$, wherein R$^{82}$ is selected from:
- C$_1$-C$_8$ alkyl, C$_3$-C$_{10}$ cycloalkyl, 4-10 membered heterocycloalkyl, C$_6$-C$_{10}$ aryl, aralkyl, 5-10 membered heteroaryl, and heteroaralkyl; or
- C$_1$-C$_8$ alkyl substituted with halo, substituted or unsubstituted amino, or hydroxy; or
- C$_3$-C$_{10}$ cycloalkyl, 4-10 membered heterocycloalkyl, C$_6$-C$_{10}$ aryl, aralkyl, 5-10 membered heteroaryl, or heteroaralkyl, each of which is substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

Exemplary 'Substituted sulfo' or 'sulfonic acid ester' groups are —S(O)$_2$—O—(C$_1$-C$_8$ alkyl) and —S(O)$_2$—O—(C$_3$-C$_{10}$ cycloalkyl), —S(O)$_2$—O—(CH$_2$)$_t$(C$_6$-C$_{10}$ aryl), —S(O)$_2$—O—(CH$_2$)$_t$(5-10 membered heteroaryl), —S(O)$_2$—O—(CH$_2$)$_t$(C$_3$-C$_{10}$ cycloalkyl), and —S(O)$_2$—O—(CH$_2$)$_t$(4-10 membered heterocycloalkyl), wherein t is an integer from 0 to 4 and any aryl, heteroaryl, cycloalkyl or heterocycloalkyl groups present, may themselves be substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

'Thiol' refers to the group —SH.

One having ordinary skill in the art of organic synthesis will recognize that the maximum number of heteroatoms in a stable, chemically feasible heterocyclic ring, whether it is aromatic or non aromatic, is determined by the size of the ring, the degree of unsaturation and the valence of the heteroatoms. In general, a heterocyclic ring may have one to four heteroatoms so long as the heteroaromatic ring is chemically feasible and stable.

'Pharmaceutically acceptable' means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

'Pharmaceutically acceptable salt' refers to a salt of a compound of the invention that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like. The term "pharmaceutically acceptable cation" refers to an acceptable cationic counter-ion of an acidic functional group. Such cations are exemplified by sodium, potassium, calcium, magnesium, ammonium, tetraalkylammonium cations, and the like.

'Pharmaceutically acceptable vehicle' refers to a diluent, adjuvant, excipient or carrier with which a compound of the invention is administered.

'Preventing' or 'prevention' refers to a reduction in risk of acquiring a disease or disorder (i.e., causing at least one of the clinical symptoms of the disease not to develop in a subject that may be exposed to or predisposed to the disease but does not yet experience or display symptoms of the disease). This term encompasses the term 'prophylaxis', which means a measure taken for the prevention of a disease.

'Prodrugs' refers to compounds, including derivatives of the compounds of the invention, which have cleavable groups and become by solvolysis or under physiological conditions the compounds of the invention which are pharmaceutically active in vivo. Such examples include, but are not limited to, choline ester derivatives and the like, N-alkylmorpholine esters and the like.

'Solvate' refers to forms of the compound that are associated with a solvent, usually by a solvolysis reaction. This physical association includes hydrogen bonding. Conventional solvents include water, ethanol, acetic acid and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates. In certain instances the solvate will be capable of isolation, for example when one or more solvent molecules are incorporated in the crystal lattice of the crystalline solid. 'Solvate' encompasses both solution-phase and isolable solvates. Representative solvates include hydrates, ethanolates and methanolates.

'Subject' includes humans. The terms 'human', 'patient' and 'subject' are used interchangeably herein.

'Therapeutically effective amount' means the amount of a compound that, when administered to a subject for treating a disease, is sufficient to effect such treatment for the disease. The "therapeutically effective amount" can vary depending on the compound, the disease and its severity, and the age, weight, etc., of the subject to be treated.

'Treating' or 'treatment' of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, 'treating' or 'treatment' refers to delaying the onset of the disease or disorder.

'Compounds of the present invention', and equivalent expressions, are meant to embrace compounds of the Formula (e) as hereinbefore described, which expression includes the prodrugs, the pharmaceutically acceptable salts, and the solvates, e.g., hydrates, where the context so permits. Similarly, reference to intermediates, whether or not they themselves are claimed, is meant to embrace their salts, and solvates, where the context so permits.

Other derivatives of the compounds of this invention have activity in both their acid and acid derivative forms, but in the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendent on the compounds of this invention are particularly useful prodrugs. In some cases it is desirable to prepare double ester type prodrugs such as (acyloxy)alkyl esters or ((alkoxycarbonyl)oxy)alkylesters. Particular such prodrugs are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds of the invention.

As used herein, the term 'isotopic variant' refers to a compound that contains unnatural proportions of isotopes at one or more of the atoms that constitute such compound. For example, an 'isotopic variant' of a compound can contain one or more non-radioactive isotopes, such as for example, deuterium ($^2H$ or D), carbon-13 ($^{13}C$), nitrogen-15 ($^{15}N$), or the like. It will be understood that, in a compound where such isotopic substitution is made, the following atoms, where present, may vary, so that for example, any hydrogen may be $^2H$/D, any carbon may be $^{13}C$, or any nitrogen may be $^{15}N$, and that the presence and placement of such atoms may be determined within the skill of the art. Likewise, the invention may include the preparation of isotopic variants with radioisotopes, in the instance for example, where the resulting compounds may be used for drug and/or substrate tissue distribution studies. The radioactive isotopes tritium, i.e. $^3H$, and carbon-14, i.e. $^{14}C$, are particularly useful for this purpose in view of their ease of incorporation and ready means of detection. Further, compounds may be prepared that are substituted with positron emitting isotopes, such as $^{11}C$, $^{18}F$, $^{15}O$ and $^{13}$N, and would be useful in Positron Emission Topography (PET) studies for examining substrate receptor occupancy.

All isotopic variants of the compounds provided herein, radioactive or not, are intended to be encompassed within the scope of the invention.

It is also to be understood that compounds that have the same molecular formula but differ in the nature or sequence of bonding of their atoms or the arrangement of their atoms in space are termed 'isomers'. Isomers that differ in the arrangement of their atoms in space are termed 'stereoisomers'.

Stereoisomers that are not mirror images of one another are termed 'diastereomers' and those that are non-superimposable mirror images of each other are termed 'enantiomers'. When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a 'racemic mixture'.

'Tautomers' refer to compounds that are interchangeable forms of a particular compound structure, and that vary in the displacement of hydrogen atoms and electrons. Thus, two structures may be in equilibrium through the movement of a electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest.

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

Compounds

As set forth earlier herein, the compounds of the present invention are useful for preventing and/or treating a broad range of conditions, among them, arthritis, Parkinson's disease, Alzheimer's disease, stroke, uveitis, asthma, myocardial infarction, the treatment and prophylaxis of pain syndromes (acute and chronic or neuropathic), traumatic brain injury, acute spinal cord injury, neurodegenerative disorders, alopecia (hair loss), inflammatory bowel disease and autoimmune disorders or conditions in mammals.

In order that the invention described herein may be more fully understood, the following structures representing compounds typical of the invention are set forth. It should be understood that these examples are for illustrative purposes only and are not to be construed as limiting this invention in any manner.

Accordingly, in a first aspect of the invention, compounds are disclosed that are capable of modifying ion channels, in vivo, having a formula I:

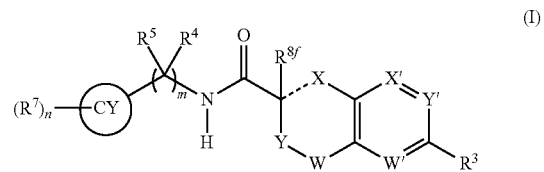

or a pharmaceutically acceptable salt thereof, and isotopic variants thereof, stereoisomers and tautomers thereof, wherein:

CY is bicycloheteroaryl;

W represents O, $CR^{8a}R^{8b}$, or $NR^{8c}$;

X represents N, O, $CR^{8a}$, $CR^{8a}R^{8b}$, or $NR^{8c}$;

Y represents $CR^{8d}R^{8e}$;

W', X', and Y' each independently represent $CR^8$ or N; provided that all three of W', X' and Y' can not be N at the same time;

$R^3$ represents hydrogen, halogen, hydroxy, substituted or unsubstituted ($C_1$-$C_6$)alkyl, substituted or unsubstituted ($C_1$-$C_6$)alkoxy or substituted or unsubstituted 3-8 membered cycloalkyl;

$R^4$ and $R^5$ each independently represent hydrogen or substituted or unsubstituted ($C_1$-$C_6$)alkyl; m is 0 or 1;

each $R^7$ is H, halogen, hydroxy, ($C_1$-$C_6$)acyl, cyano, substituted or unsubstituted ($C_1$-$C_6$)alkyl, or substituted or unsubstituted ($C_1$-$C_6$)alkoxy; or $R^7$ is ($C_1$-$C_6$)alkyl, halo($C_1$-$C_6$)alkyl, hydroxy($C_1$-$C_6$)alkyl, ($C_1$-$C_6$)alkoxy, hydroxy($C_1$-$C_6$)alkoxy, halo($C_1$-$C_6$)alkoxy; n is 1, 2, 3, 4 or 5;

each $R^8$ independently represents hydrogen, halogen, hydroxy, cyano, substituted or unsubstituted ($C_1$-$C_6$) alkyl, substituted or unsubstituted ($C_1$-$C_6$)alkoxy, or substituted or unsubstituted 3-8 membered cycloalkyl;

each $R^{8a}$, $R^{8b}$, $R^{8d}$, $R^{8e}$ and $R^{8f}$ independently represents hydrogen, halo, hydroxy, substituted or unsubstituted ($C_1$-$C_6$)alkyl, or substituted or unsubstituted 3-8 membered cycloalkyl;

$R^{81}$ represents hydrogen, or substituted or unsubstituted ($C_1$-$C_6$)alkyl; and the dotted bond represents a single or a double bond;

provided that:
  i) when the dotted bond is a double bond, then $R^{8f}$ is absent;
  ii) when X is N or O; then $R^{8f}$ is H or substituted or unsubstituted alkyl;
  iii) when X is O; then W is O or $NR^{8c}$; and
  iv) when W is O; and the dotted bond is a single bond; then X is O or $NR^{8c}$.

In one particular embodiment, with respect to compounds of formula I, the dotted bond is a single bond.

In one particular embodiment, with respect to compounds of formula I, the dotted bond is a double bond.

In one particular embodiment, with respect to compounds of formula I, when $R^3$, $R^4$, $R^5$, $R^7$, $R^8$, $R^{8a}$, $R^{8b}$, $R^{8c}$, $R^{8d}$, $R^{8e}$ or $R^{8f}$ is substituted ($C_1$-$C_6$)alkyl; the substitution is selected from one or more halo, hydroxy or ($C_1$-$C_6$)alkoxy.

In one particular embodiment, with respect to compounds of formula I, $R^3$, $R^4$, $R^5$, $R^7$, $R^8$, $R^{8a}$, $R^{8b}$, $R^{8c}$, $R^{8d}$, $R^{8e}$ or $R^{8f}$ is ($C_1$-$C_6$)alkyl, halo($C_1$-$C_6$)alkyl, hydroxy($C_1$-$C_6$)alkyl, or ($C_1$-$C_6$)alkoxy ($C_1$-$C_6$)alkyl.

In one particular embodiment, with respect to compounds of formula I, $R^3$, $R^4$, $R^5$, $R^7$, $R^8$, $R^{8a}$, $R^{8b}$, $R^{8c}$, $R^{8d}$, $R^{8e}$ or $R^{8f}$ is hydrogen.

In one particular embodiment, with respect to compounds of formula I, $R^3$, $R^4$, $R^5$, $R^7$, $R^8$, $R^{8a}$, $R^{8b}$, $R^{8c}$, $R^{8d}$, $R^{8e}$ or $R^{8f}$ is other than hydrogen.

In one particular embodiment, with respect to compounds of formula I, $R^{8c}$ is hydrogen.

In one particular embodiment, with respect to compounds of formula I, $R^{8c}$ is other than hydrogen.

In one particular embodiment, with respect to compounds of formula I, when $R^3$, $R^8$, $R^{8a}$, $R^{8b}$, $R^{8d}$, $R^{8e}$ or $R^{8f}$ is substituted 3-6 membered cycloalkyl; the substitution is selected from one or more halo, hydroxy or $(C_1-C_6)$alkyl.

In one particular embodiment, with respect to compounds of formula I, when $R^3$, $R^7$, or $R^8$ is substituted $(C_1-C_6)$alkoxy; the substitution is selected from one or more halo, hydroxy or $(C_1-C_6)$alkoxy.

In one particular embodiment, with respect to compounds of formula I, $R^7$ is $(C_1-C_6)$alkyl, halo$(C_1-C_6)$alkyl, hydroxy$(C_1-C_6)$alkyl, $(C_1-C_6)$alkoxy, hydroxy$(C_1-C_6)$alkoxy, halo$(C_1-C_6)$alkoxy.

In one particular embodiment, with respect to compounds of formula I, $R^7$ is acyl, or hydroxymethyl.

In one particular embodiment, with respect to compounds of formula I, $R^3$ is $(C_1-C_6)$alkyl, halo$(C_1-C_6)$alkyl, hydroxy$(C_1-C_6)$alkyl, $(C_1-C_6)$alkoxy, hydroxy$(C_1-C_6)$alkoxy, halo$(C_1-C_6)$alkoxy.

In one particular embodiment, with respect to compounds of formula I, when $R^3$ is halo$(C_1-C_6)$alkyl, dihalo$(C_1-C_6)$alkyl, or trihalo$(C_1-C_6)$alkyl.

In one particular embodiment, with respect to compounds of formula I, $R^3$ is fluoro$(C_1-C_6)$alkyl, difluoro$(C_1-C_6)$alkyl, or trifluoro$(C_1-C_6)$alkyl.

In one particular embodiment, with respect to compounds of formula I, $R^3$ is halo$(C_1-C_6)$alkoxy, dihalo$(C_1-C_6)$alkoxy, or trihalo$(C_1-C_6)$alkoxy.

In one particular embodiment, with respect to compounds of formula I, $R^3$ is fluoro$(C_1-C_6)$alkoxy, difluoro$(C_1-C_6)$alkoxy, or trifluoro$(C_1-C_6)$alkoxy.

In one particular embodiment, with respect to compounds of formula I, $R^8$ is $(C_1-C_6)$alkyl, halo$(C_1-C_6)$alkyl, hydroxy$(C_1-C_6)$alkyl, $(C_1-C_6)$alkoxy, hydroxy$(C_1-C_6)$alkoxy, halo$(C_1-C_6)$alkoxy.

In one particular embodiment, with respect to compounds of formula I, $R^8$ is halo$(C_1-C_6)$alkyl, dihalo$(C_1-C_6)$alkyl, or trihalo$(C_1-C_6)$alkyl.

In one particular embodiment, with respect to compounds of formula I, $R^8$ is fluoro$(C_1-C_6)$alkyl, difluoro$(C_1-C_6)$alkyl, or trifluoro$(C_1-C_6)$alkyl.

In one particular embodiment, with respect to compounds of formula I, $R^8$ is halo$(C_1-C_6)$alkoxy, dihalo$(C_1-C_6)$alkoxy, or trihalo$(C_1-C_6)$alkoxy.

In one particular embodiment, with respect to compounds of formula I, $R^8$ is fluoro$(C_1-C_6)$alkoxy, difluoro$(C_1-C_6)$alkoxy, or trifluoro$(C_1-C_6)$alkoxy.

In one particular embodiment, with respect to compounds of formula I, CY is unsubstituted quinolinyl, isoquinolinyl, indolyl, dihydroindolyl, benzofuranyl, benzothiophenyl, benzopyranyl, pyranopyridyl, benzimidazolyl, indazolyl, benzthiazolyl, benzoxazolyl, pyrazolopyridine, pyrazolooxazinyl, or thiazolopyridine.

In one particular embodiment, with respect to compounds of formula I, CY is quinolinyl, isoquinolinyl, indolyl, dihydroindolyl, benzofuranyl, benzothiophenyl, benzopyranyl, pyranopyridyl, benzimidazolyl, indazolyl, benzthiazolyl, benzoxazolyl, pyrazolopyridine, pyrazolooxazinyl, or thiazolopyridine; substituted with one or more groups selected from halogen, hydroxy, substituted or unsubstituted $(C_1-C_6)$alkyl, and substituted or unsubstituted $(C_1-C_6)$alkoxy.

In one particular embodiment, with respect to compounds of formula I, CY is substituted quinolinyl, isoquinolinyl, indolyl, dihydroindolyl, benzofuranyl, benzothiophenyl, benzopyranyl, pyranopyridyl, benzimidazolyl, indazolyl, benzthiazolyl, benzoxazolyl, pyrazolopyridine, pyrazolooxazinyl, or thiazolopyridine; and the substitution is selected from halogen, hydroxy, unsubstituted $(C_1-C_6)$alkyl, and unsubstituted $(C_1-C_6)$alkoxy.

In one particular embodiment, with respect to compounds of formula I, CY is quinolinyl, isoquinolinyl, indolyl, dihydroindolyl, benzofuranyl, benzothiophenyl, benzopyranyl, pyranopyridyl, benzimidazolyl, indazolyl, benzthiazolyl, benzoxazolyl, pyrazolopyridine, pyrazolooxazinyl, or thiazolopyridine; substituted with substituted $(C_1-C_6)$alkyl, and substituted $(C_1-C_6)$alkoxy; and the substitution on alkyl or alkoxy is selected from one or more halo, hydroxy or $(C_1-C_6)$alkoxy.

In one particular embodiment, with respect to compounds of formula I, CY is quinolinyl, isoquinolinyl, indolyl, benzofuranyl, benzothiophenyl, benzopyranyl, pyranopyridyl, benzimidazolyl, indazolyl, benzthiazolyl, benzoxazolyl, pyrazolopyridine, or thiazolopyridine; substituted with one or more groups selected from Cl, F, Me, and $CF_3$.

In one particular embodiment, with respect to compounds of formula I, the compound is according to formulae IIa-IIh:

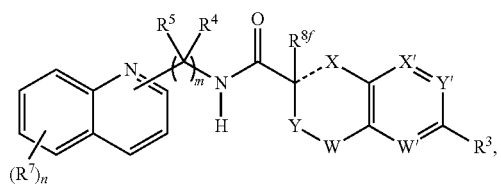

IIa

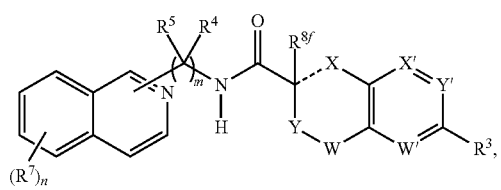

IIb

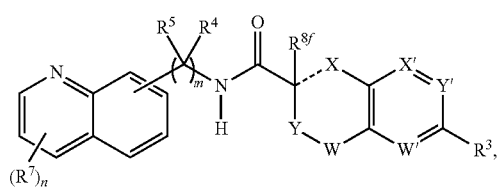

IIc

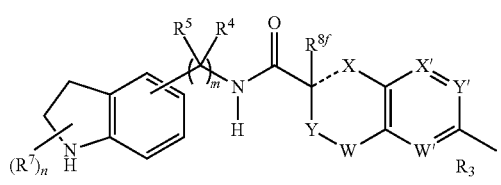

IId

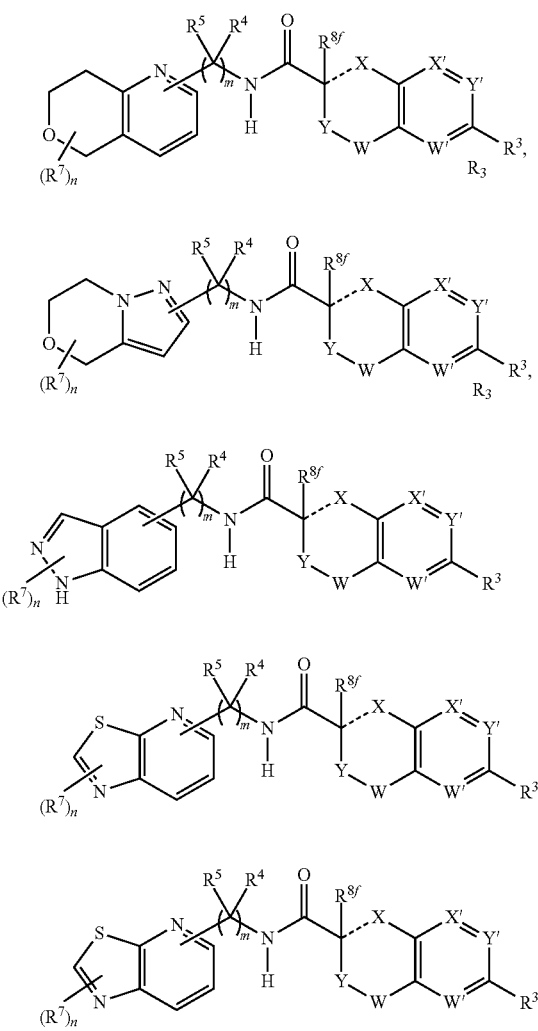

wherein W, X, Y, W', X', Y', $R^3$, $R^4$, $R^5$, and $R^{8f}$ are described for formula I; $R^7$ is H, halogen, hydroxy, $(C_1-C_6)$acyl, $(C_1-C_6)$alkyl unsubstituted or substituted with one or more groups selected from halo, hydroxy and $(C_1-C_6)$alkoxy, or $(C_1-C_6)$alkoxy unsubstituted or substituted with one or more groups selected from halo, hydroxy and $(C_1-C_6)$alkoxy; m is 0 or 1; n is 1, 2, 3 or 4; and the dotted bond represents a single or a double bond.

In one particular embodiment, with respect to compounds of formula I-IIh, W and X each independently represent $CR^{8a}R^{8b}$; and the dotted bond is a single bond.

In one particular embodiment, with respect to compounds of formula I-IIh, W represents $CR^{8a}R^{8b}$; X represents $CR^{8a}$; and the dotted bond is a double bond.

In one particular embodiment, with respect to compounds of formula I-IIh, W represents O; the dotted bond is a double bond; and X is $CR^{8a}$.

In one particular embodiment, with respect to compounds of formula I-IIh, X represents O; and the dotted bond is a single bond.

In one particular embodiment, with respect to compounds of formula I-IIh, W represents $CR^{8a}R^{8b}$.

In one particular embodiment, with respect to compounds of formula I-IIh, W represents $NR^{8c}$.

In one particular embodiment, with respect to compounds of formula I-IIh, W represents $NR^{8c}$; and $R^{8c}$ is hydrogen.

In one particular embodiment, with respect to compounds of formula I-IIh, W represents $NR^{8c}$; and $R^{8c}$ is other than hydrogen.

In one particular embodiment, with respect to compounds of formula I-IIh, W represents O.

In one particular embodiment, with respect to compounds of formula I-IIh, X represents $NR^{8c}$.

In one particular embodiment, with respect to compounds of formula I-IIh, X represents $NR^{8c}$; and $R^{8c}$ is hydrogen.

In one particular embodiment, with respect to compounds of formula I-IIh, X represents $NR^{8c}$; and $R^{8c}$ is other than hydrogen.

In one particular embodiment, with respect to compounds of formula I-IIh, X represents O.

In one particular embodiment, with respect to compounds of formula I-IIh, $R^5$ is hydrogen.

In one particular embodiment, with respect to compounds of formula I-IIh, $R^5$ is Me.

In one particular embodiment, with respect to compounds of formula I-IIh, $R^{8f}$ is H or Me.

In one particular embodiment, with respect to compounds of formula I-IIh, $R^7$ is H.

In one particular embodiment, with respect to compounds of formula I-IIh, n is 1 or 2; and $R^7$ is alkyl or hydroxyalkyl.

In one particular embodiment, with respect to compounds of formula I-IIh, n is 1 or 2; and $R^7$ is Me, Et, or $CH_2OH$.

In one particular embodiment, with respect to compounds of formula I-IIh, m is 1

In one particular embodiment, with respect to compounds of formula I-IIh, m is 0.

In one particular embodiment, with respect to compounds of formula I, the compound is according to formulae IIIa, IIIb, IIIc, IIId, or IIIe:

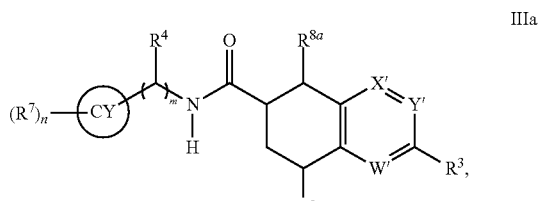

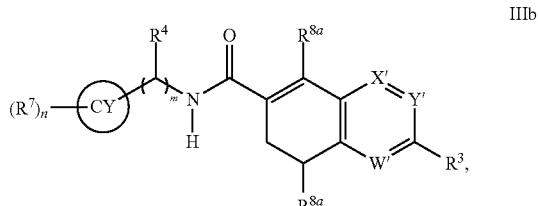

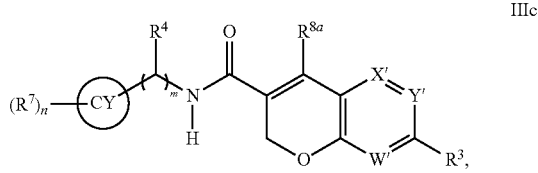

-continued

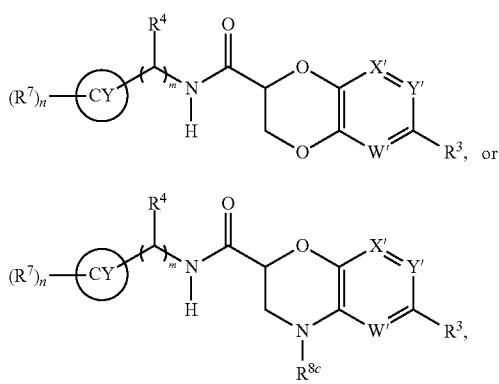

or a pharmaceutically acceptable salt, and isotopic variants thereof, stereoisomers and tautomers thereof, wherein CY, W', X', Y', m, n, $R^3$, $R^4$, $R^{8a}$, and $R^{8c}$, are described for formula I; and $R^7$ is H, halogen, hydroxy, $(C_1\text{-}C_6)$ acyl, $(C_1\text{-}C_6)$alkyl unsubstituted or substituted with one or more groups selected from halo, hydroxy and $(C_1\text{-}C_6)$ alkoxy, or $(C_1\text{-}C_6)$alkoxy unsubstituted or substituted with one or more groups selected from halo, hydroxy and $(C_1\text{-}C_6)$alkoxy.

In one particular embodiment, with respect to compounds of formula IIIa-IIIc, the dotted bond is a single bond.

In one particular embodiment, with respect to compounds of formula IIIa-IIIc, the dotted bond is a double bond.

In one particular embodiment, with respect to compounds of formula I-IIIe, X' is $CR^8$.

In one particular embodiment, with respect to compounds of formula I-IIIe, Y' is $CR^8$.

In one particular embodiment, with respect to compounds of formula I-IIIe, X', and Y' each independently represent $CR^8$.

In one particular embodiment, with respect to compounds of formula I-IIIe, X' is CH.

In one particular embodiment, with respect to compounds of formula I-IIIe, Y' is CH.

In one particular embodiment, with respect to compounds of formula I-IIIe, X', and Y' each independently represent CH.

In one particular embodiment, with respect to compounds of formula I-IIIe, one of X', and Y' represents N and the other represents $CR^8$.

In one particular embodiment, with respect to compounds of formula I-IIIe, X' is N.

In one particular embodiment, with respect to compounds of formula I-IIIe, Y' is N.

In one particular embodiment, with respect to compounds of formula I-IIIe, X' is N, and Y' is CH.

In one particular embodiment, with respect to compounds of formula I-IIIe, X' is CH, and Y' is N.

In one particular embodiment, with respect to compounds of formula I-IIIe, Y' is CH, and X' is $CR^8$.

In one particular embodiment, with respect to compounds of formula I-IIIe, CY is quinolinyl, isoquinolinyl, indazolyl, thiazolopyridinyl, tetrahydropyranopyridyl, or dihydroindolyl.

In one particular embodiment, with respect to compounds of formula I-IIIe, CY is quinolinyl, or indazolyl.

In one particular embodiment, with respect to compounds of formula I-IIIe, CY is thiazolopyridinyl.

In one particular embodiment, with respect to compounds of formula I-IIIe, CY is tetrahydropyranopyridyl.

In one particular embodiment, with respect to compounds of formula I-IIIe, CY is dihydroindolyl.

In one particular embodiment, with respect to compounds of formula I-IIIe, CY is indolinyl.

In one particular embodiment, with respect to compounds of formula IIIa-IIIe, $R^5$ is hydrogen.

In one particular embodiment, with respect to compounds of formula IIIa-IIIe, $R^5$ is Me.

In one particular embodiment, with respect to compounds of formula IIIa-IIIe, $R^{8f}$ is H or Me.

In one particular embodiment, with respect to compounds of formula IIIa-IIIe, $R^7$ is H.

In one particular embodiment, with respect to compounds of formula IIIa-IIIe, n is 1 or 2; and $R^7$ is alkyl or hydroxyalkyl.

In one particular embodiment, with respect to compounds of formula IIIa-IIIe, n is 1 or 2; and $R^7$ is Me, Et, or $CH_2OH$.

In one particular embodiment, with respect to compounds of formula IIIa-IIIe, m is 1

In one particular embodiment, with respect to compounds of formula IIIa-IIIe, m is 0.

In one particular embodiment, with respect to compounds of formula I-IIIe, X', is CH; and Y' is $CR^8$.

In one particular embodiment, with respect to compounds of formula I-IIIe, X', is CH; Y' is $CR^8$; and $R^8$ is $(C_1\text{-}C_6)$alkyl, halo$(C_1\text{-}C_6)$alkoxy, or halo$(C_1\text{-}C_6)$alkyl.

In one particular embodiment, with respect to compounds of formula I-IIIe, X', is CH; Y' is $CR^8$; and $R^8$ is F, Br, Cl, $OCF_3$, or $CF_3$.

In one particular embodiment, with respect to compounds of formula I-IIIe, X', is CH; Y' is $CR^8$; and $R^8$ is Cl, $OCF_3$, or $CF_3$.

In one particular embodiment, with respect to compounds of formula I-IIIe, $R^{8a}$ is H.

In one particular embodiment, with respect to compounds of formula I-IIIe, $R^{8a}$ is Me.

In one particular embodiment, with respect to compounds of formula I-IIIe, $R^{8c}$ is Me.

In one particular embodiment, with respect to compounds of formula I-IIIe, $R^4$ is H.

In one particular embodiment, with respect to compounds of formula I-IIIe, $R^4$ is Me.

In one particular embodiment, with respect to compounds of formula IIIe, $R^{8c}$ is hydrogen.

In one particular embodiment, with respect to compounds of formula IIIe, $R^{8c}$ is other than hydrogen.

In one particular embodiment, with respect to compounds of formula I, the compound is according to formulae IVa, IVb, IVc, IVd, or IVe:

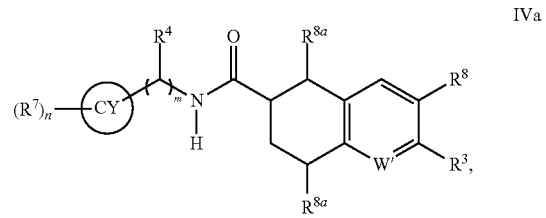

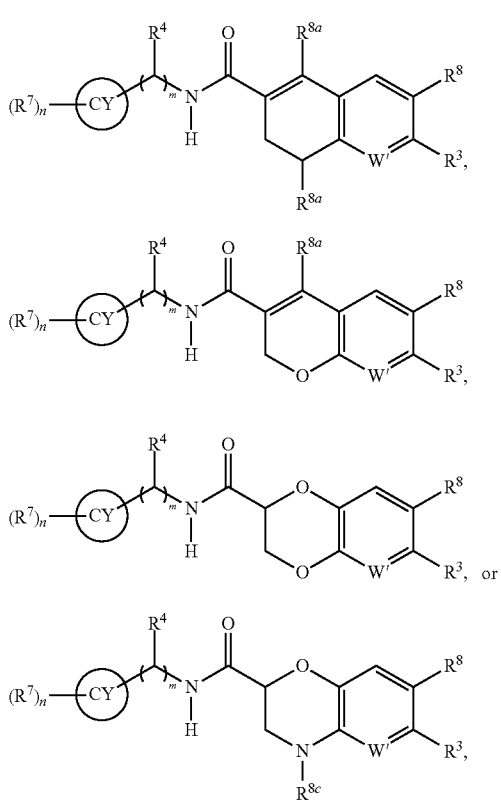

or a pharmaceutically acceptable salt, and isotopic variants thereof, stereoisomers and tautomers thereof, wherein m, n, $R^3$, $R^8$, $R^{8a}$, and $R^{8c}$, are as described for formula I; $R^7$ is H, halogen, hydroxy, $(C_1$-$C_6)$acyl, $(C_1$-$C_6)$alkyl unsubstituted or substituted with one or more groups selected from halo, hydroxy and $(C_1$-$C_6)$alkoxy, or $(C_1$-$C_6)$alkoxy unsubstituted or substituted with one or more groups selected from halo, hydroxy and $(C_1$-$C_6)$alkoxy; W' is CH or N; and CY is

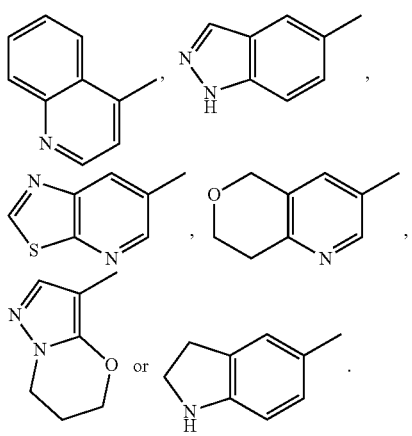

In one particular embodiment, with respect to compounds of formula I-IVe, $R^7$ is H.

In one particular embodiment, with respect to compounds of formula I-IVe, $R^7$ is Me, $CH_2OH$ or $CH(OH)CH_2OH$; and n is 1.

In one particular embodiment, with respect to compounds of formula I-IVe, W' is N.

In one particular embodiment, with respect to compounds of formula I-IVe, W' is CH.

In one particular embodiment, with respect to compounds of formula I-IVe, $R^3$ is H, halo, alkyl, alkoxy, haloalkoxy, or haloalkyl.

In one particular embodiment, with respect to compounds of formula I-IVe, $R^3$ is $(C_1$-$C_6)$alkyl, halo$(C_1$-$C_6)$alkoxy, or halo$(C_1$-$C_6)$alkyl.

In one particular embodiment, with respect to compounds of formula I-IVe, $R^3$ is H.

In one particular embodiment, with respect to compounds of formula I-IVe, $R^3$ is H, F, Br, Cl, $OCF_3$, or $CF_3$.

In one particular embodiment, with respect to compounds of formula I-IVe, $R^3$ is H, Me, Et, i-Pr, t-Bu, 1-methyl-1-trifluoromethylethyl, or 1-methyl-1-hydroxyethyl.

In one particular embodiment, with respect to compounds of formula I-IVe, $R^3$ is H or $CF_3$.

In one particular embodiment, with respect to compounds of formula I-IVe, $R^8$ is H, halo, $(C_1$-$C_6)$alkyl, $(C_1$-$C_6)$alkoxy, haloalkoxy, or halo$(C_1$-$C_6)$alkyl.

In one particular embodiment, with respect to compounds of formula I-IVe, $R^8$ is $C_1$-$C_6$ alkyl, halo $C_1$-$C_6$ alkoxy, or halo $C_1$-$C_6$ alkyl.

In one particular embodiment, with respect to compounds of formula I-IVe, $R^8$ is H.

In one particular embodiment, with respect to compounds of formula I-IVe, $R^8$ is H, F, Br, Cl, $OCF_3$, or $CF_3$.

In one particular embodiment, with respect to compounds of formula I-IVe, $R^8$ is H, Me, Et, i-Pr, t-Bu, 1-methyl-1-trifluoromethylethyl, or 1-methyl-1-hydroxyethyl.

In one particular embodiment, with respect to compounds of formula I-IVe, $R^8$ is H or $CF_3$.

In one particular embodiment, with respect to compounds of formula I-IVe, $R^3$ is $CF_3$ and $R^8$ is H.

In one particular embodiment, with respect to compounds of formula I-IVe, $R^3$ is 1-methyl-1-hydroxyethyl and $R^8$ is H.

In one particular embodiment, with respect to compounds of formula I-IVe, $R^3$ is 1-methyl-1-trifluoromethylethyl and $R^8$ is H.

In one particular embodiment, with respect to compounds of formula I-IVe, $R^8$ is $CF_3$ and $R^3$ is H.

In one particular embodiment, with respect to compounds of formula I-IVe, $R^8$ is 1-methyl-1-hydroxyethyl and $R^3$ is H.

In one particular embodiment, with respect to compounds of formula I-IVe, $R^8$ is 1-methyl-1-trifluoromethylethyl and $R^3$ is H.

In one particular embodiment, with respect to compounds of formula I-IVe, $R^{8a}$ is H.

In one particular embodiment, with respect to compounds of formula I-IVe, $R^{8a}$ is Me.

In one particular embodiment, with respect to compounds of formula I-IVe, $R^{8c}$ is Me.

In one particular embodiment, with respect to compounds of formula I-IVe, $R^{8c}$ is Me, Et, or i-Pr.

In one particular embodiment, with respect to compounds of formula I-IVe, m is 0.

In one particular embodiment, with respect to compounds of formula I-IVe, m is 1; and $R^4$ is H.

In one particular embodiment, with respect to compounds of formula I-IVe, m is 1; and $R^4$ is Me.

In one particular embodiment, with respect to compounds of formula IVe, $R^{8c}$ is hydrogen.

In one particular embodiment, with respect to compounds of formula IVe, $R^{8c}$ is other than hydrogen.

In one particular embodiment, with respect to compounds of formula I-IVe, CY is

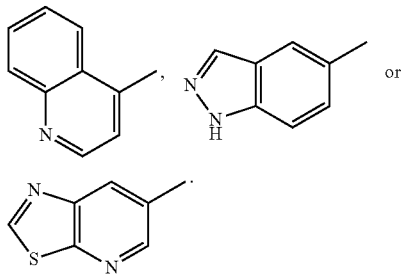

In one particular embodiment, with respect to compounds of formula I-IVe, CY is

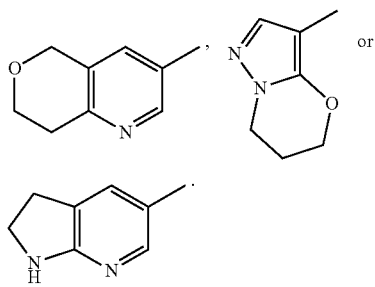

In one particular embodiment, with respect to compounds of formula I-IVe, the dotted bound is a single bond.

In one particular embodiment, with respect to compounds of formula I-IVe, the dotted bound is a double bond.

In one particular embodiment, with respect to compounds of formula I, CY is quinolinyl, isoquinolinyl, 1,5-naphthyridinyl, indolyl, indolinyl, benzofuranyl, benzothiophenyl, benzopyranyl, pyranopyridyl, benzimidazolyl, indazolyl, benzthiazolyl, benzoxazolyl, pyrazolopyridine, pyrrolopyridinyl, dihydropyrrolopyridinyl, or thiazolopyridine. In one embodiment, the substitution ($R^7$) on CY is selected from one or more groups from halogen, hydroxy, substituted or unsubstituted ($C_1$-$C_6$)alkyl, and substituted or unsubstituted ($C_1$-$C_6$)alkoxy. In another embodiment the substitution ($R^7$) on CY is selected from one or more groups from ($C_1$-$C_6$)alkyl, hydroxy($C_1$-$C_6$)alkyl, ($C_1$-$C_6$)alkoxy, hydroxy($C_1$-$C_6$)alkoxy, ($C_1$-$C_6$)alkoxy-($C_1$-$C_6$)alkyl, ($C_1$-$C_6$)alkoxy-($C_1$-$C_6$)alkoxy, and halo($C_1$-$C_6$)alkyl.

In one particular embodiment, with respect to compounds of formula I, CY is quinolinyl, isoquinolinyl, indolyl, benzofuranyl, benzothiophenyl, benzopyranyl, pyranopyridyl, benzimidazolyl, indazolyl, benzthiazolyl, benzoxazolyl, pyrazolopyridine, or thiazolopyridine; substituted with one or more groups selected from halogen, hydroxy, substituted or unsubstituted ($C_1$-$C_6$)alkyl, and substituted or unsubstituted ($C_1$-$C_6$)alkoxy.

In one particular embodiment, with respect to compounds of formula I, W', X', and Y' each independently represent $CR^8$.

In one particular embodiment, with respect to compounds of formula I, one of W', X', and Y' is N and the rest are each independently $CR^8$. In another embodiment, W' is N and the rest are each independently $CR^8$.

In one particular embodiment, with respect to compounds of formula I, two of W', X' and Y' is N and the rest are each independently $CR^8$. In another embodiment, W' is N; Y' is N; and X' is $CR^8$.

In one embodiment, with respect to compounds of formulae I-IIh, W' is N and Y' is $CR^8$.

In one embodiment, with respect to compounds of formulae I-IIh, W' is $CR^8$ and Y' is N.

In one embodiment, with respect to compounds of formulae I-IIh, each of W' and Y' is N.

In one embodiment, with respect to compounds of formulae I-IIh, n is 1, 2, or 3. In another embodiment, n is 1 or 2. In yet another embodiment, n is 1.

In one embodiment, with respect to compounds of formulae I-IIh, each $R^7$ is independently selected from halogen, hydroxy, substituted or unsubstituted ($C_1$-$C_6$)alkyl, substituted or unsubstituted ($C_1$-$C_6$)alkoxy. In another embodiment, each $R^7$ is selected from Cl, F, Me, Et, or $CF_3$.

In certain embodiments, $R^3$, $R^7$, $R^8$, $R^{8a}$, $R^{8b}$, $R^{8c}$, $R^{8d}$, $R^{8e}$ or $R^{8f}$ is ($C_1$-$C_6$)alkyl; In another embodiment, the alkyl group is $C_1$-$C_5$alkyl. In a further embodiment, the alkyl group is $C_1$-$C_4$alkyl.

In one embodiment, the alkyl group is optionally substituted by one or more groups (such as 1 to 3 substituents, in particular one substituent group, which substituent group may be independently selected from halo, hydroxy, cyano, nitro, trifluoromethyl, trifluoromethoxy, azido, $-NR^{10}SO_2R^9$, $-SO_2NR^9R^{10}$, $-C(O)R^9$, $-C(O)OR^9$, $-OC(O)R^9$, $-C(O)NR^9R^{10}$, $-NR^9R^{10}$, $-(CR^{10}R^{11})_m$ $OR^{10}$ and wherein m is an integer from 1 to 5.

In one embodiment, the ($C_1$-$C_6$)alkyl group is optionally substituted by one or more halogens.

In one embodiment, the ($C_1$-$C_6$)alkyl group is optionally substituted by one or more F.

In one embodiment, the ($C_1$-$C_6$)alkyl group is optionally substituted by OH.

In one embodiment, each $R^9$ is independently selected from H, $C_1$-$C_8$alkyl, $-(CH_2)_t(C_6$-$C_{10}$ aryl), $-(CH_2)_t(C_5$-$C_{10}$ heteroaryl), $-(CH_2)_t(C_3$-$C_{10}$ cycloalkyl), and $-(CH_2)_t$ ($C_5$-$C_{10}$ heterocycloalkyl), wherein t is an integer from 0 to 4.

In one embodiment, each $R^9$ is as described above, and any aryl, heteroaryl, cycloalkyl or heterocycloalkyl groups present, may themselves be substituted by $C_1$-$C_4$alkyl, halo, $C_1$-$C_4$alkoxy, $C_{1-4}$haloalkyl, $C_1$-$C_4$hydroxyalkyl, or $C_1$-$C_4$haloalkoxy or hydroxy.

In one embodiment, each $R^9$ is as described above, and each of $R^{10}$ and $R^{11}$ independently represents H or $C_1$-$C_6$alkyl.

In one embodiment, each $R^9$ is as described above and each of $R^{12}$ and $R^{13}$ independently represents H or $C_1$-$C_4$alkyl.

In one embodiment, each of $R^{10}$ and $R^{11}$ independently represents H or $C_1$-$C_6$alkyl.

In one embodiment, each $R^9$ is other than H.

In certain embodiments, when $R^3$, $R^7$ or $R^8$ is alkoxy; the alkoxy group is $-OR^9$; and $R^9$ is as described in the above embodiments; provided that $R^9$ is other than H.

In certain embodiments, when $R^3$, $R^7$, $R^8$, $R^{8a}$, $R^{8b}$, $R^{8c}$, $R^{8d}$, $R^{8e}$ or $R^{8f}$ is cycloalkyl; the cycloalkyl group is $C_3$-$C_{10}$cycloalkyl. In another embodiment, the cycloalkyl group is $C_3$-$C_8$cycloalkyl. In a further embodiment, the cycloalkyl group is $C_3$-$C_7$cycloalkyl.

In one embodiment, the cycloalkyl group is optionally substituted by one or more groups, such as 1 to 3 substituents, in particular one substituent group, which substituent group may be independently selected from halo, $C_1$-$C_6$alkyl, and trifluoromethyl.

In another embodiment, with respect to compounds of formula I, the compound is selected from:
6-tert-Butyl-2,3-dihydro-benzo[1,4]dioxine-2-carboxylic acid (quinolin-4-ylmethyl)-amide;

6-Chloro-2H-chromene-3-carboxylic acid (quinolin-4-ylmethyl)-amide;
6-Bromo-2H-chromene-3-carboxylic acid (quinolin-4-ylmethyl)-amide;
6-Trifluoromethoxy-2H-chromene-3-carboxylic acid (quinolin-4-ylmethyl)-amide;
6-Chloro-2H-chromene-3-carboxylic acid [1-(1H-indazol-5-yl)-ethyl]-amide;
(S)-6-tert-Butyl-2,3-dihydro-benzo[1,4]dioxine-2-carboxylic acid [1-(1H-indazol-5-yl)-ethyl]-amide;
(R)-6-tert-Butyl-2,3-dihydro-benzo[1,4]dioxine-2-carboxylic acid [1-(1H-indazol-5-yl)-ethyl]-amide;
7-tert-Butyl-2,3-dihydro-benzo[1,4]dioxine-2-carboxylic acid (2-hydroxymethyl-thiazolo[5,4-b]pyridin-6-yl)-amide;
4-Methyl-6-trifluoromethyl-3,4-dihydro-2H-benzo[1,4]oxazine-2-carboxylic acid [1-(1H-indazol-5-yl)-ethyl]-amide;
2-(2,2,2-Trifluoro-1,1-dimethyl-ethyl)-5,6,7,8-tetrahydroquinoline-6-carboxylic acid [1-(1H-indazol-5-yl)-ethyl]-amide;
(R)-2-(2,2,2-Trifluoro-1,1-dimethyl-ethyl)-5,6,7,8-tetrahydro-quinoline-6-carboxylic acid [(R)-1-(1H-indazol-5-yl)-ethyl]-amide;
(S)-2-(2,2,2-Trifluoro-1,1-dimethyl-ethyl)-5,6,7,8-tetrahydro-quinoline-6-carboxylic acid [(R)-1-(1H-indazol-5-yl)-ethyl]-amide;
(R)-6-Trifluoromethyl-2,3-dihydro-benzo[1,4]dioxine-2-carboxylic acid [1-(1H-indazol-5-yl)-ethyl]-amide;
(S)-6-Trifluoromethyl-2,3-dihydro-benzo[1,4]dioxine-2-carboxylic acid [1-(1H-indazol-5-yl)-ethyl]-amide;
(R)-2-(2,2,2-Trifluoro-1,1-dimethyl-ethyl)-5,6,7,8-tetrahydro-quinoline-6-carboxylic acid (2-hydroxymethyl-thiazolo[5,4-b]pyridin-6-yl)-amide;
(R)-6-Trifluoromethyl-2,3-dihydro-benzo[1,4]dioxine-2-carboxylic acid (2-hydroxymethyl-thiazolo[5,4-b]pyridin-6-yl)-amide;
(R)-6-Trifluoromethyl-2,3-dihydro-benzo[1,4]dioxine-2-carboxylic acid (7,8-dihydro-5H-pyrano[4,3-b]pyridin-3-yl)-amide;
(R)-2-(2,2,2-Trifluoro-1,1-dimethyl-ethyl)-5,6,7,8-tetrahydro-quinoline-6-carboxylic acid (7,8-dihydro-5H-pyrano[4,3-b]pyridin-3-yl)-amide;
(S)-2-(2,2,2-Trifluoro-1,1-dimethyl-ethyl)-5,6,7,8-tetrahydro-quinoline-6-carboxylic acid (7,8-dihydro-5H-pyrano[4,3-b]pyridin-3-yl)-amide;
(R)-2-(2,2,2-Trifluoro-1,1-dimethyl-ethyl)-5,6,7,8-tetrahydro-quinoline-6-carboxylic acid [(R)-1-(6,7-dihydro-5H-pyrazolo[5,1-b][1,3]oxazin-3-yl)-ethyl]-amide;
(R)-2-(2,2,2-Trifluoro-1,1-dimethyl-ethyl)-5,6,7,8-tetrahydro-quinoline-6-carboxylic acid quinolin-3-ylamide;
(S)-2-(2,2,2-Trifluoro-1,1-dimethyl-ethyl)-5,6,7,8-tetrahydro-quinoline-6-carboxylic acid [(R)-1-(6,7-dihydro-5H-pyrazolo[5,1-b][1,3]oxazin-3-yl)-ethyl]-amide;
(R)-2-(2,2,2-Trifluoro-1,1-dimethyl-ethyl)-5,6,7,8-tetrahydro-quinoline-6-carboxylic acid (1-acetyl-2,3-dihydro-1H-indol-6-yl)-amide;
6-Methyl-2-(2,2,2-trifluoro-1,1-dimethyl-ethyl)-5,6,7,8-tetrahydro-quinoline-6-carboxylic acid (2-hydroxymethyl-thiazolo[5,4-b]pyridin-6-yl)-amide;
(S)-6-Trifluoromethyl-2,3-dihydro-benzo[1,4]dioxine-2-carboxylic acid [(R)-1-(1H-indazol-5-yl)-ethyl]-amide; and
(R)-6-Trifluoromethyl-2,3-dihydro-benzo[1,4]dioxine-2-carboxylic acid [(R)-1-(1H-indazol-5-yl)-ethyl]-amide;
or a pharmaceutically acceptable salt thereof, and isotopic variants thereof, stereoisomers and tautomers thereof.

In yet further particular embodiments, the compounds of the invention are set forth and may be selected from a comprehensive listing of such compounds, set forth later on herein in Table 1. The Table contains in excess of 10 compounds that have been or can be synthesized and have as a group, demonstrated activity in their capacity of modifying ion channels, in vivo, and thereby functioning in the therapeutic applications set forth herein in relation to capsaicin and the vanilloid receptor.

As discussed above, suitable compounds capable of modifying ion channels in vivo, may be selected from those listed in Table 1, below, and may be prepared either as shown or in the form of a pharmaceutically acceptable salt, solvate or prodrug thereof; and stereoisomers and tautomers thereof. All such variants are contemplated herein and are within the scope of the present invention.

In certain aspects, the present invention provides prodrugs and derivatives of the compounds according to the formulae above. Prodrugs are derivatives of the compounds of the invention, which have cleavable groups and become by solvolysis or under physiological conditions the compounds of the invention, which are pharmaceutically active, in vivo. Such examples include, but are not limited to, choline ester derivatives and the like, N-alkylmorpholine esters and the like.

Other derivatives of the compounds of this invention have activity in both their acid and acid derivative forms, but the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Particular prodrugs include simple aliphatic or aromatic esters, amides and anhydrides derived from acidic groups pendent on the compounds of this invention. In some cases it is desirable to prepare double ester type prodrugs such as (acyloxy)alkyl esters or ((alkoxycarbonyl)oxy)alkylesters. Particular esters are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds of the invention.

Assay Methods

Chronic Constriction Injury Model (CCI Model):

Male Sprague-Dawley rats (270-300 g; B.W., Charles River, Tsukuba, Japan) are used. The chronic constriction injury (CCI) operation is performed according to the method described by Bennett and Xie (Bennett, G. J. and Xie, Y. K. Pain, 33:87-107, 1988). Briefly, animals are anesthetized with sodium pentobarbital (64.8 mg/kg, i.p.) and the left common sciatic nerve is exposed at the level of the middle of the thigh by blunt dissection through the biceps femoris. A portion of the sciatic nerve proximal to its trifurcation is freed of adhering tissue and 4 ligatures (4-0 silk) are tied loosely around it with about 1 mm space. A sham operation is performed as same as CCI surgery except for sciatic nerve ligation. Two weeks after surgery, mechanical allodynia is evaluated by application of von Frey hairs (VFHs) to the plantar surface of the hind paw. The lowest amount of force of VFH required to elicit a response is recorded as the paw withdrawal threshold (PWT). VFH testing is performed at 0.5, 1 and 2 hr post-dosing. Experimental data are analyzed using Kruskal-Wallis test followed by Dunn's test for multiple comparisons or Mann-Whitney U-test for paired comparison.

Caco-2 Permeability

Caco-2 permeability is measured according to the method described in Shiyin Yee, Pharmaceutical Research, 763 (1997).

Caco-2 cells are grown on filter supports (Falcon HTS multiwell insert system) for 14 days. Culture medium is removed from both the apical and basolateral compartments and the monolayers are preincubated with pre-warmed 0.3 ml apical buffer and 1.0 ml basolateral buffer for 0.75 hour at 37° C. in a shaker water bath at 50 cycles/min. The apical buffer consists of Hanks Balanced Salt Solution, 25 mM D-glucose monohydrate, 20 mM MES Biological Buffer, 1.25 mM $CaCl_2$ and 0.5 mM $MgCl_2$ (pH 6.5). The basolateral buffer consists of Hanks Balanced Salt Solution, 25 mM D-glucose monohydrate, 20 mM HEPES Biological Buffer, 1.25 mM $CaCl_2$ and 0.5 mM $MgCl_2$ (pH 7.4). At the end of the preincubation, the media is removed and test compound solution (10 μM) in buffer is added to the apical compartment. The inserts are moved to wells containing fresh basolateral buffer and incubated for 1 hr. Drug concentration in the buffer is measured by LC/MS analysis.

Flux rate (F, mass/time) is calculated from the slope of the cumulative appearance of substrate on the receiver side and apparent permeability coefficient (Papp) is calculated from the following equation:

$$Papp(cm/sec)=(F*VD)/(SA*MD)$$

where SA is surface area for transport (0.3 $cm^2$), VD is the donor volume (0.3 ml), MD is the total amount of drug on the donor side at t=0. All data represent the mean of 2 inserts. Monolayer integrity is determined by Lucifer Yellow transport.

Human Dofetilide Binding

A cell paste of HEK-293 cells expressing the HERG product can be suspended in 10-fold volume of 50 mM Tris buffer adjusted at pH 7.5 at 25° C. with 2 M HCl containing 1 mM $MgCl_2$, 10 mM KCl. The cells are homogenized using a Polytron homogenizer (at the maximum power for 20 seconds) and centrifuged at 48,000 g for 20 minutes at 4° C. The pellet is resuspended, homogenized and centrifuged once more in the same manner. The resultant supernatant is discarded and the final pellet is resuspended (10-fold volume of 50 mM Tris buffer) and homogenized at the maximum power for 20 seconds. The membrane homogenate is aliquoted and stored at −80° C. until use. An aliquot is used for protein concentration determination using a Protein Assay Rapid Kit and ARVO SX plate reader (Wallac). All the manipulation, stock solution and equipment are kept on ice at all times. For saturation assays, experiments are conducted in a total volume of 200 μl. Saturation is determined by incubating 20 μl of [3H]-dofetilide and 160 μl of membrane homogenates (20-30 μg protein per well) for 60 min at room temperature in the absence or presence of 10 μM dofetilide at final concentrations (20 μl) for total or nonspecific binding, respectively. All incubations are terminated by rapid vacuum filtration over polyetherimide (PEI) soaked glass fiber filter papers using Skatron cell harvester followed by two washes with 50 mM Tris buffer (pH 7.5 at 25° C.). Receptor-bound radioactivity is quantified by liquid scintillation counting using a Packard LS counter.

For the competition assay, compounds are diluted in 96 well polypropylene plates as 4-point dilutions in semi-log format. All dilutions are performed in DMSO first and then transferred into 50 mM Tris buffer (pH 7.5 at 25° C.) containing 1 mM $MgCl_2$, 10 mM KCl so that the final DMSO concentration becomes equal to 1%. Compounds are dispensed in triplicate in assay plates (4 μl). Total binding and nonspecific binding wells are set up in 6 wells as vehicle and 10 μM dofetilide at final concentration, respectively. The radioligand is prepared at 5.6× final concentration and this solution is added to each well (36 μl). The assay is initiated by addition of YSi poly-L-lysine Scintillation Proximity Assay (SPA) beads (50 μl, 1 mg/well) and membranes (110 μl, 20 μg/well). Incubation is continued for 60 min at room temperature. Plates are incubated for a further 3 hours at room temperature for beads to settle. Receptor-bound radioactivity is quantified by counting Wallac MicroBeta plate counter.

HERG Assay

HEK 293 cells which stably express the HERG potassium channel are used for electrophysiological study. The methodology for stable transfection of this channel in HEK cells can be found elsewhere (Z. Zhou et al., 1998, Biophysical Journal, 74, pp 230-241). Before the day of experimentation, the cells are harvested from culture flasks and plated onto glass coverslips in a standard Minimum Essential Medium (MEM) medium with 10% Fetal Calf Serum (FCS). The plated cells are stored in an incubator at 37° C. maintained in an atmosphere of 95% $O_2$/5% $CO_2$. Cells are studied between 15-28 hrs after harvest.

HERG currents are studied using standard patch clamp techniques in the whole-cell mode. During the experiment the cells are superfused with a standard external solution of the following composition (mM); NaCl, 130; KCl, 4; $CaCl_2$, 2; $MgCl_2$, 1; Glucose, 10; HEPES, 5; pH 7.4 with NaOH. Whole-cell recordings are made using a patch clamp amplifier and patch pipettes which have a resistance of 1-3 MOhm when filled with the standard internal solution of the following composition (mM); KCl, 130; MgATP, 5; $MgCl_2$, 1.0; HEPES, 10; EGTA 5, pH 7.2 with KOH. Only those cells with access resistances below 15 MΩ and seal resistances>1 GΩ are accepted for further experimentation. Series resistance compensation is applied up to a maximum of 80%. No leak subtraction is done. However, acceptable access resistance depends on the size of the recorded currents and the level of series resistance compensation that can safely be used. Following the achievement of whole cell configuration and sufficient time for cell dialysis with pipette solution (>5 min), a standard voltage protocol is applied to the cell to evoke membrane currents. The voltage protocol is as follows. The membrane is depolarized from a holding potential of −80 mV to +40 mV for 1000 ms. This is followed by a descending voltage ramp (rate 0.5 mV msec−1) back to the holding potential. The voltage protocol is applied to a cell continuously throughout the experiment every 4 seconds (0.25 Hz). The amplitude of the peak current elicited around −40 mV during the ramp is measured. Once stable evoked current responses are obtained in the external solution, vehicle (0.5% DMSO in the standard external solution) is applied for 10-20 mM by a peristaltic pump. Provided there are minimal changes in the amplitude of the evoked current response in the vehicle control condition, the test compound of 0.3, 1, 3 or 10 mM is applied for a 10 min period. The 10 min period includes the time during which supplying solution is passing through the tube from solution reservoir to the recording chamber via the pump. Exposure time of cells to the compound solution is more than 5 min after the drug concentration in the chamber well reaches the intended concentration. There is a subsequent wash period of a 10-20 min to assess reversibility. Finally, the cells are exposed to high dose of dofetilide (5 mM), a specific IKr blocker, to evaluate the insensitive endogenous current.

All experiments are performed at room temperature (23±1° C.). Evoked membrane currents are recorded on-line on a computer, filtered at 500-1 KHz (Bessel −3 dB) and sampled at 1-2KHz using the patch clamp amplifier and a specific data analyzing software. Peak current amplitude, which generally occurs at around −40 mV, is measured off line on the computer.

The arithmetic mean of the ten values of amplitude is calculated under vehicle control conditions and in the presence of drug. Percent decrease of IN in each experiment is obtained by the normalized current value using the following formula: IN=(1−ID/IC)×100, where ID is the mean current value in the presence of drug and IC is the mean current value under control conditions. Separate experiments are performed for each drug concentration or time-matched control, and arithmetic mean in each experiment is defined as the result of the study.

Half-Life in Human Liver Microsomes (HLM)

Test compounds (1 µM) are incubated with 3.3 mM $MgCl_2$ and 0.78 mg/mL HLM (HL101) in 100 mM potassium phosphate buffer (pH 7.4) at 37° C. on the 96-deep well plate. The reaction mixture is split into two groups, a non-P450 and a P450 group. NADPH is only added to the reaction mixture of the P450 group. An aliquot of samples of the P450 group is collected at 0, 10, 30, and 60 min time point, where 0 min time point indicates the time when NADPH is added into the reaction mixture of the P450 group. An aliquot of samples of non-P450 group is collected at −10 and 65 min time point. Collected aliquots are extracted with acetonitrile solution containing an internal standard. The precipitated protein is spun down in a centrifuge (2000 rpm, 15 min). The compound concentration in the supernatant is measured by LC/MS/MS system.

The half-life value is obtained by plotting the natural logarithm of the peak area ratio of compounds/internal standard versus time. The slope of the line of best fit through the points yields the rate of metabolism (k). This is converted to a half-life value using following equations:

Half-life=ln 2/$k$

Mono-Iodoacetate (MIA)-Induced OA Model

Male 6-weeks-old Sprague-Dawley (SD, Japan SLC or Charles River Japan) rats are anesthetized with pentobarbital. The injection site (knee) of MIA is shaved and cleaned with 70% ethanol. Twenty-five ml of MIA solution or saline is injected in the right knee joint using a 29 G needle. The effect of joint damage on the weight distribution through the right (damaged) and left (untreated) knee is assessed using an incapacitance tester (Linton Instrumentation, Norfolk, UK). The force exerted by each hind limb is measured in grams. The weight-bearing (WB) deficit is determined by a difference of weight loaded on each paw. Rats are trained to measure the WB once a week until 20 days post MIA-injection. Analgesic effects of compounds are measured at 21 days after the MIA injection. Before the compound administration, the "pre value" of WB deficit is measured. After the administration of compounds, attenuation of WB deficits is determined as analgesic effects.

Complete Freund's Adjuvant (CFA) Induced Thermal and Mechanical Hyperalgesia in Rats Thermal Hyperalgesia Male 6-week-old SD rats are used. Complete Freund's adjuvant (CFA, 300 mg of *Mycobacterium Tuberculosis* H37RA (Difco, MI) in 100 µL of liquid paraffin (Wako, Osaka, Japan)) is injected into the plantar surface of a hind paw of the rats. Two days after CFA-injection, thermal hyperalgesia is determined by the method described previously (Hargreaves et al., 1988) using the plantar test apparatus (Ugo-Basil, Varese, Italy). Rats are adapted to the testing environment for at least 15 minutes prior to any stimulation. Radiant heat is applied to the plantar surface of a hind paw and paw withdrawal latencies (PWL, seconds) are determined. The intensity of radiant heat is adjusted to produce the stable PWL of 10 to 15 seconds. The test compound is administered in a volume of 0.5 mL per 100 g body weight. PWL are measured after 1, 3 or 5 hours after drug administration.

Mechanical Hyperalgesia

Male 4-week-old SD rats are used. CFA (300 mg of *Mycobacterium Tuberculosis* H37RA (Difco, MI) in 100 µL of liquid paraffin (Wako, Osaka, Japan)) is injected into the plantar surface of a hind paw of the rats. Two days after CFA-injection, mechanical hyperalgesia is tested by measuring paw withdrawal threshold (PWT, grams) to pressure using the analgesy-Meter (Ugo-Basile, Varese, Italy). The animals are gently restrained, and steadily increasing pressure is applied to the dorsal surface of a hind paw via a plastic tip. The pressure required to elicit paw withdrawal is determined. The test compound is administered in a volume of 0.5 mL per 100 g body weight. PWT are measured after 1, 3 or 5 hours after drug administration.

Pharmaceutical Compositions

When employed as pharmaceuticals, the amide compounds of this invention are typically administered in the form of a pharmaceutical composition. Such compositions can be prepared in a manner well known in the pharmaceutical art and comprise at least one active compound.

Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of this invention can be administered by a variety of routes including by way of non limiting example, oral, rectal, transdermal, subcutaneous, intravenous, intramuscular and intranasal. Depending upon the intended route of delivery, the compounds of this invention are preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the furansulfonic acid compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope of this invention.

The compounds of this invention can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of Remington's The Science and Practice of Pharmacy, 21st edition, 2005, Publisher: Lippincott Williams & Wilkins, which is incorporated herein by reference.

The compounds of this invention can also be administered in sustained release forms or from sustained release drug delivery systems. A description of representative sustained release materials can be found in Remington's Pharmaceutical Sciences.

The following formulation examples illustrate representative pharmaceutical compositions that may be prepared in accordance with this invention. The present invention, however, is not limited to the following pharmaceutical compositions.

Formulation 1

Tablets

A compound of the invention is admixed as a dry powder with a dry gelatin binder in an approximate 1:2 weight ratio. A minor amount of magnesium stearate is added as a lubricant. The mixture is formed into 240-270 mg tablets (80-90 mg of active compound per tablet) in a tablet press.

Formulation 2

Capsules

A compound of the invention is admixed as a dry powder with a starch diluent in an approximate 1:1 weight ratio. The mixture is filled into 250 mg capsules (125 mg of active compound per capsule).

Formulation 3

Liquid

A compound of the invention (125 mg) may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water may then added to produce a total volume of 5 mL.

Formulation 4

Tablets

A compound of the invention may be admixed as a dry powder with a dry gelatin binder in an approximate 1:2 weight ratio. A minor amount of magnesium stearate is added as a lubricant. The mixture is formed into 450-900 mg tablets (150-300 mg of active compound) in a tablet press.

Formulation 5

Injection

A compound of the invention is dissolved or suspended in a buffered sterile saline injectable aqueous medium to a concentration of approximately 5 mg/mL.

Formulation 6

Topical

Stearyl alcohol (250 g) and a white petrolatum (250 g) are melted at about 75° C. and then a mixture of a compound of the invention (50 g) methylparaben (0.25 g), propylparaben (0.15 g), sodium lauryl sulfate (10 g), and propylene glycol (120 g) dissolved in water (about 370 g) is added and the resulting mixture is stirred until it congeals.

Methods of Treatment

The present compounds are used as therapeutic agents for the treatment of conditions in mammals. Accordingly, the compounds and pharmaceutical compositions of this invention find use as therapeutics for preventing and/or treating neurodegenerative, autoimmune and inflammatory conditions in mammals including humans. Thus, and as stated earlier, the present invention includes within its scope, and extends to, the recited methods of treatment, as well as to the compounds for use in such methods, and for the preparation of medicaments useful for such methods.

In a method of treatment aspect, this invention provides a method of treating a mammal susceptible to or afflicted with a condition associated with arthritis, uveitis, asthma, myocardial infarction, traumatic brain injury, acute spinal cord injury, alopecia (hair loss), inflammatory bowel disease and autoimmune disorders, which method comprises administering an effective amount of one or more of the pharmaceutical compositions just described.

In yet another method of treatment aspect, this invention provides a method of treating a mammal susceptible to or afflicted with a condition that gives rise to pain responses or that relates to imbalances in the maintenance of basal activity of sensory nerves. Compounds have use as analgesics for the treatment of pain of various geneses or etiology, for example acute, inflammatory pain (such as pain associated with osteoarthritis and rheumatoid arthritis); various neuropathic pain syndromes (such as post-herpetic neuralgia, trigeminal neuralgia, reflex sympathetic dystrophy, diabetic neuropathy, Guillian Barre syndrome, fibromyalgia, phantom limb pain, post-mastectomy pain, peripheral neuropathy, HIV neuropathy, and chemotherapy-induced and other iatrogenic neuropathies); visceral pain, (such as that associated with gastroesophageal reflex disease, irritable bowel syndrome, inflammatory bowel disease, pancreatitis, and various gynecological and urological disorders), dental pain and headache (such as migraine, cluster headache and tension headache).

In additional method of treatment aspects, this invention provides methods of treating a mammal susceptible to or afflicted with neurodegenerative diseases and disorders such as, for example Parkinson's disease, Alzheimer's disease and multiple sclerosis; diseases and disorders which are mediated by or result in neuroinflammation such as, for example traumatic brain injury, stroke, and encephalitis; centrally-mediated neuropsychiatric diseases and disorders such as, for example depression mania, bipolar disease, anxiety, schizophrenia, eating disorders, sleep disorders and cognition disorders; epilepsy and seizure disorders; prostate, bladder and bowel dysfunction such as, for example urinary incontinence, urinary hesitancy, rectal hypersensitivity, fecal incontinence, benign prostatic hypertrophy and inflammatory bowel disease; respiratory and airway disease and disorders such as, for example, allergic rhinitis, asthma and reactive airway disease and chronic obstructive pulmonary disease; diseases and disorders which are mediated by or result in inflammation such as, for example rheumatoid arthritis and osteoarthritis, myocardial infarction, various autoimmune diseases and disorders, uveitis and atherosclerosis; itch/pruritus such as, for example psoriasis; alopecia (hair loss); obesity; lipid disorders; cancer; blood pressure; spinal cord injury; and renal disorders method comprises administering an effective condition-treating or condition-preventing amount of one or more of the pharmaceutical compositions just described.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

For the prevention and/or treatment of long-term conditions, such as neurodegenerative and autoimmune conditions, the regimen for treatment usually stretches over many months or years so oral dosing is preferred for patient convenience and tolerance. With oral dosing, one to five and especially two to four and typically three oral doses per day are representative regimens. Using these dosing patterns, each dose provides from about 0.01 to about 20 mg/kg of the compound or its derivative, with preferred doses each providing from about 0.1 to about 10 mg/kg and especially about 1 to about 5 mg/kg.

Transdermal doses are generally selected to provide similar or lower blood levels than are achieved using injection doses.

When used to prevent the onset of a neurodegenerative, autoimmune or inflammatory condition, the compounds or their derivatives of this invention will be administered to a patient at risk for developing the condition, typically on the advice and under the supervision of a physician, at the dosage levels described above. Patients at risk for developing a particular condition generally include those that have a family history of the condition, or those who have been identified by genetic testing or screening to be particularly susceptible to developing the condition.

The compounds of this invention can be administered as the sole active agent or they can be administered in combination with other agents, including other active derivatives. A VR1 antagonist may be usefully combined with another pharmacologically active compound, or with two or more other pharmacologically active compounds, particularly in the treatment of pain. For example, a VR1 antagonist, particularly a compound of formula (I), or a pharmaceutically acceptable salt or solvate thereof, as defined above, may be administered simultaneously, sequentially or separately in combination with one or more agents selected from:

an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;

a nonsteroidal antiinflammatory drug (NSAID), e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac;

a barbiturate sedative, e.g. amobarbital, aprobarbital, butabarbital, butalbital, mephobarbital, metharbital, methohexital, pentobarbital, phenobarbital, secobarbital, talbutal, theamylal or thiopental;

a benzodiazepine having a sedative action, e.g. chlordiazepoxide, clorazepate, diazepam, flurazepam, lorazepam, oxazepam, temazepam or triazolam;

an H1 antagonist having a sedative action, e.g. diphenhydramine, pyrilamine, promethazine, chlorpheniramine or chlorocyclizine;

a sedative such as glutethimide, meprobamate, methaqualone or dichloralphenazone;

a skeletal muscle relaxant, e.g. baclofen, carisoprodol, chlorzoxazone, cyclobenzaprine, methocarbamol or orphrenadine;

an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex®, a combination formulation of morphine and dextromethorphan), topiramate, neramexane or perzinfotel including an NR2B antagonist, e.g. ifenprodil, traxoprodil or (−)-(R)-6-{2-[4-(3-fluorophenyl)-4-hydroxy-1-piperidinyl]-1-hydroxyethyl-3,4-dihydro-2(1H)-quinolinone;

an alpha-adrenergic, e.g. doxazocin, tamsulosin, clonidine, guanfacine, dexmetatomidine, modafinil, or 4-amino-6,7-dimethoxy-2-(5-methane-sulfonamido-1,2,3,4-tetrahydroisoquinol-2-yl)-5-(2-pyridyl) quinazoline;

a tricyclic antidepressant, e.g. desipramine, imipramine, amitriptyline or nortriptyline;

an anticonvulsant, e.g. carbamazepine, lamotrigine, topiratmate or valproate;

a tachykinin (NK) antagonist, particularly an NK-3, NK-2 or NK-1 antagonist, e.g. (aR,9R)-7-[3,5-bis(trifluoromethyl) benzyl]-8,9,10,11-tetrahydro-9-methyl-5-(4-methylphenyl)-7H-[1,4]diazocino[2,1-g][1,7]-naphthyridine-6-13-dione (TAK-637), 5-[[(2R,3S)-2-[(1R)-1-[3,5-bis(trifluoromethyl) phenyl]ethoxy-3-(4-fluorophenyl)-4-morpholinyl]-methyl]-

1,2-dihydro-3H-1,2,4-triazol-3-one (MK-869), aprepitant, lanepitant, dapitant or 3-[[2-methoxy-5-(trifluoromethoxy) phenyl]-methylamino]-2-phenylpiperidine (2S,3S);

a muscarinic antagonist, e.g oxybutynin, tolterodine, propiverine, tropsium chloride, darifenacin, solifenacin, temiverine and ipratropium;

a COX-2 selective inhibitor, e.g. celecoxib, rofecoxib, parecoxib, valdecoxib, deracoxib, etoricoxib, or lumiracoxib;

a coal-tar analgesic, in particular paracetamol;

a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion® or sarizotan;

a beta-adrenergic such as propranolol;

a local anaesthetic such as mexiletine;

a corticosteroid such as dexamethasone;

a 5-HT receptor agonist or antagonist, particularly a 5-HT1B/1D agonist such as eletriptan, sumatriptan, naratriptan, zolmitriptan or rizatriptan;

a 5-HT2A receptor antagonist such as R(+)-alpha-(2,3-dimethoxy-phenyl)-1-[2-(4-fluorophenylethyl)]-4-piperidinemethanol (MDL-100907);

a cholinergic (nicotinic) analgesic, such as ispronicline (TC-1734), (E)-N-methyl-4-(3-pyridinyl)-3-buten-1-amine (RJR-2403), (R)-5-(2-azetidinylmethoxy)-2-chloropyridine (ABT-594) or nicotine;

Tramadol®;

a PDEV inhibitor, such as 5-[2-ethoxy-5-(4-methyl-1-piperazinyl-sulphonyl)phenyl]-1-methyl-3-n-propyl-1,6-dihydro-7H-pyrazolo[4,3-d]pyrimidin-7-one (sildenafil), (6R,12aR)-2,3,6,7,12,12a-hexahydro-2-methyl-6-(3,4-methylenedioxyphenyl)-pyrazino[2',1':6,1]-pyrido[3,4-b]indole-1,4-dione (IC-351 or tadalafil), 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil), 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one, 5-(5-acetyl-2-propoxy-3-pyridinyl)-3-ethyl-2-(1-isopropyl-3-azetidinyl)-2,6-dihydro-7H-pyrazolo[4,3-d]pyrimidin-7-one, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, 4-[(3-chloro-4-methoxybenzyl)amino]-2-[(2S)-2-(hydroxymethyl) pyrrolidin-1-yl]-N-(pyrimidin-2-ylmethyl)pyrimidine-5-carboxamide, 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide;

an alpha-2-delta ligand such as gabapentin, pregabalin, 3-methylgabapentin, (1a,3a,5a)(3-amino-methyl-bicyclo[3.2.0]hept-3-yl)-acetic acid, (3S,5R)-3_aminomethyl-5_methyl-heptanoic acid, (3S,5R)-3_amino-5_methyl-heptanoic acid, (3S,5R)-3_amino-5_methyl-octanoic acid, (2S,4S)-4-(3-chlorophenoxy)proline, (2S,4S)-4-(3-fluorobenzyl)-proline, [(1R,5R,6S)-6-(aminomethyl)bicyclo[3.2.0]hept-6-yl]acetic acid, 3-(1-aminomethyl-cyclohexylmethyl)-4H-[1,2,4]oxadiazol-5-one, C-[1-(1H-tetrazol-5-ylmethyl)-cycloheptyl]-methylamine, (3S,4S)-(1-aminomethyl-3,4-dimethyl-cyclopentyl)-acetic acid, (3S,5R)-3_aminomethyl-5_methyl-octanoic acid, (3S,5R)-3_amino-5_methyl-nonanoic acid, (3S,5R)-3_amino-5_methyl-octanoic acid, (3R,4R,5R)-3-amino-4,5-dimethyl-heptanoic acid and (3R,4R,5R)-3-amino-4,5-dimethyl-octanoic acid;

a cannabinoid;

a serotonin reuptake inhibitor such as sertraline, sertraline metabolite demethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine and trazodone;

a noradrenaline (norepinephrine) reuptake inhibitor, such as maprotiline, lofepramine, mirtazepine, oxaprotiline, fezolamine, tomoxetine, mianserin, buprorion, buprorion metabolite hydroxybuproprion, nomifensine and viloxazine (Vivalan®), especially a selective noradrenaline reuptake inhibitor such as reboxetine, in particular (S,S)-reboxetine;

a dual serotonin-noradrenaline reuptake inhibitor, such as venlafaxine, venlafaxine metabolite O-desmethylvenlafaxine, clomipramine, clomipramine metabolite desmethylclomipramine, duloxetine, milnacipran and imipramine;

an inducible nitric oxide synthase (iNOS) inhibitor such as S-[2-[(1-iminoethyl)amino]ethyl]-L-homocysteine, S-[2-[(1-iminoethyl)-amino]ethyl]-4,4-dioxo-L-cysteine, S-[2-[(1-iminoethyl)amino]ethyl]-2-methyl-L-cysteine, (2S,5Z)-2-amino-2-methyl-7-[(1-iminoethyl)amino]-5-heptenoic acid, 2-[[(1R,3S)-3-amino-4-hydroxy-1-(5-thiazolyl)-butyl]thio]-5-chloro-3-pyridinecarbonitrile; 2-[[(1R,3S)-3-amino-4-hydroxy-1-(5-thiazolyl)butyl]thio]-4-chlorobenzonitrile, (2S,4R)-2-amino-4-[[2-chloro-5-(trifluoromethyl)phenyl]thio]-5-thiazolebutanol, 2-[[(1R,3S)-3-amino-4-hydroxy-1-(5-thiazolyl) butyl]thio]-6-(trifluoromethyl)-3 pyridinecarbonitrile, 2-[[(1R,3S)-3-amino-4-hydroxy-1-(5-thiazolyl)butyl]thio]-5-chlorobenzonitrile, N-[4-[2-(3-chlorobenzylamino)ethyl]phenyl]thiophene-2-carboxamidine, or guanidinoethyldisulfide;

an acetylcholinesterase inhibitor such as donepezil;

a prostaglandin E2 subtype 4 (EP4) antagonist such as N-[({2-[4-(2-ethyl-4,6-dimethyl-1H-imidazo[4,5-c]pyridin-1-yl)phenyl]ethyl}amino)-carbonyl]-4-methylbenzenesulfonamide or 4-[(1S)-1-({[5-chloro-2-(3-fluorophenoxy) pyridin-3-yl]carbonyl}amino)ethyl]benzoic acid;

a leukotriene B4 antagonist; such as 1-(3-biphenyl-4-ylmethyl-4-hydroxy-chroman-7-yl)-cyclopentanecarboxylic acid (CP-105696), 5-[2-(2-Carboxyethyl)-3-[6-(4-methoxyphenyl)-5E-hexenyl]oxyphenoxy]-valeric acid (ONO-4057) or DPC-11870, a 5-lipoxygenase inhibitor, such as zileuton, 6-[(3-fluoro-5-[4-methoxy-3,4,5,6-tetrahydro-2H-pyran-4-yl])phenoxymethyl]-1-methyl-2-quinolone (ZD-2138), or 2,3,5-trimethyl-6-(3-pyridylmethyl),1,4-benzoquinone (CV-6504);

a sodium channel blocker, such as lidocaine;

a 5-HT3 antagonist, such as ondansetron;

and the pharmaceutically acceptable salts and solvates thereof.

In as much as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions.

Preparation of the Compounds

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The target compounds are synthesized by known reactions outlined in the following schemes. The products are isolated and purified by known standard procedures. Such procedures include (but are not limited to) recrystallization, column chromatography or HPLC.

In this specification, especially in "General Synthesis" and "Examples", the following abbreviations can and may be used:

BEP 2-bromo-1-ethylpyridinium tetrafluoroborate

BOP benzotriazol-1-yloxy-tris(dimethylamino)phosphonium hexafluorophosphate

CDI 2-chloro-1,3-dimethylimidazolinium chloride

Co(TPP) 5, 10, 15, 20 tetraphenyl-21H, 23H porphine Co(II)

DCC dicyclohexylcarbodiimide

DCM dichloromethane

DME 1,2-dimethoxyethane, dimethoxyethane

DMF N,N-dimethylformamide

DMSO dimethyl sulfoxide

EDC 1-ethyl-3-(3'-dimethylaminopropyl)carbodiimide hydrogen chloride)

EtOAc ethyl acetate

EtOH ethanol

HBTU O-Benzotriazole-N,N,N',N'-tetramethyl-uronium-hexafluoro-phosphate

HOBt 1-hydroxybenzotriazole

MeOH methanol

NMP N-methyl-2-pyrrolidone

PdCl$_2$(pddf).CH$_2$Cl$_2$ palladiumdichloro-1,1'-bis(diphenylphosphino)ferrocene-dichloromethane complex THF tetrahydrofuran TFA trifluoroacetic acid General Synthesis The compounds of the present invention may be prepared by a variety of processes well known for the preparation of compounds of this type, for example as shown in the following reaction Schemes. The term "protecting group", as used hereinafter, means a hydroxy or amino protecting group which is selected from typical hydroxy or amino protecting groups described in Protective Groups in Organic Synthesis edited by T. W. Greene et al. (John Wiley & Sons, 1999).

Synthesis of Intermediates

Intermediate 1

2-(1,1,1-Trifluoro-2-methylpropan-2-yl)-5,6,7,8-tetrahydroquinoline-6-carboxylic acid

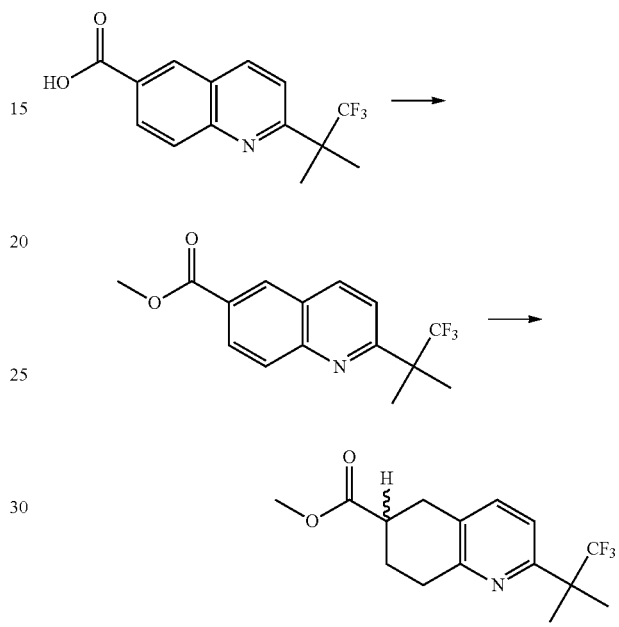

A. Methyl 2-(1,1,1-trifluoro-2-methylpropan-2-yl) quinoline-6-carboxylate and Methyl 2-(1,1,1-trifluoro-2-methylpropan-2-yl)-5,6,7,8-tetrahydroquinoline-6-carboxylate Methanolic HCl, prepared from methanol (8 mL) and acetyl chloride (1.1 mL, 15 mmol, 3 equiv), was charged to a 30 mL pressure vessel containing 2-(2,2,2-trifluoro-1,1-dimethyl-ethyl)-quinoline-6-carboxylic acid (1.42 g, 5.00 mmol), and the mixture placed in an oil bath at. After 1.6 h the mixture was removed from the heat and concentrated to afford the quinoline methyl ester (assumed 5.0 mmol) as a solid, which was used directly in the next step.

A 250 mL flask was charged with the crude methyl ester (assumed 5.00 mmol), platinum dioxide monohydrate (110 mg, 0.50 mmol, 10 mol %) and trifluoroacetic acid (20 mL), then evacuated and flushed with hydrogen 3 times. The mixture was placed in an oil bath at 60° C. and hydrogenated for 14.5 h. The mixture was diluted with water (20 mL), poured into 2M Na$_2$CO$_3$ (170 mL), and extracted with DCM (2×50 mL). The combined organic layers were dried (MgSO$_4$), filtered and concentrated to an oil, which was absorbed on silica. Chromatography on silica (0-10% EtOAc/hexane) afforded the pyridyl ester (0.98 g, 65%) as an oil. $^1$H NMR (400 MHz, CDCl$_3$) δ 9.22 (d, J=8.1 Hz, 1H), 7.48 (d, J=8.1 Hz, 1H), 3.74 (s, 3H), 3.08-2.88 (m, 4H), 2.82-2.72 (m, 1H), 2.36-2.26 (m, 1H), 2.02-1.92 (m, 1H), 1.58 (s, 6H). m/z=302.0 (M+H)$^+$.

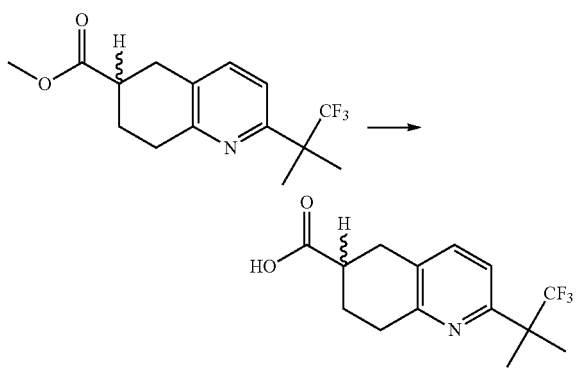

B. 2-(1,1,1-Trifluoro-2-methylpropan-2-yl)-5,6,7,8-tetrahydroquinoline-6-carboxylic acid A solution of methyl 2-(1,1,1-trifluoro-2-methylpropan-2-yl)-5,6,7,8-tetrahydroquinoline-6-carboxylate (0.97 g, 3.2 mmol) in methanol (20 mL) was treated with 1 M aqueous sodium hydroxide (6 mL, 2 equiv), and the mixture was heated to reflux. After 1.5 h the cooled mixture was diluted with water (40 mL), adjusted to pH 6 with $H_3PO_4$, and extracted with DCM (3×20 mL). The combined organic layers were dried ($Na_2SO_4$), filtered and concentrated to a solid (0.76 g, 82%). $^1$H NMR (400 MHz, DMSO-$d_6$) δ 12.34 (br s, 1H), 7.55 (d, J=8.1 Hz, 1H), 7.41 (d, J=8.1 Hz, 1H), 2.99-2.83 (m, 4H), 2.77-2.69 (m, 1H), 2.19-2.11 (m, 1H), 1.91-1.81 (m, 1H), 1.54 (s, 6H); m/z=288.4 (M+H)$^+$.

Alternative Synthesis of Ester Precursor

The following describes the preparation of an ester (ethyl 4-(pyrrolidin-1-yl)cyclohex-3-enecarboxylate and ethyl 2-(1,1,1-trifluoro-2-methylpropan-2-yl)-5,6,7,8-tetrahydroquinoline-6-carboxylate) that may serve as a precursor in the preparation of Intermediate 1.

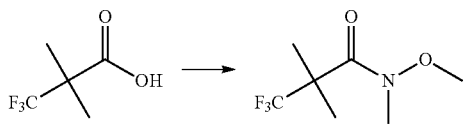

3,3,3-Trifluoro-N-methoxy-N,2,2-trimethylpropanamide

A 100 mL flask was charged with 3,3,3-trifluoro-2,2-dimethylpropanoic acid (1.00 g, 6.41 mmol), methylene chloride (25 mL) and DMF (1 drop). The system was purged with nitrogen and cooled to 0° C. Oxalyl chloride (0.650 mL, 7.69 mmol) was added dropwise over about 1 minute and the reaction was stirred at 0° C. for 2 min, then allowed to warm to room temperature. After 4 hours, a solution of N,O-dimethylhydroxylamine hydrochloride (0.937 g, 9.61 mmol) and N,N-diisopropylethylamine (3.35 mL, 19.2 mmol) in methylene chloride (5 mL) was added to the resulting acid chloride and the mixture was stirred at room temperature for 1 hour. The mixture was diluted with ether (50 mL) and washed with 1 M $NaH_2PO_4$ (2×15 mL), saturated $NaHCO_3$ (15 mL), dried ($Na_2SO_4$), filtered and evaporated to obtain the amide as an oil (1.38 g, quant.), which was used in the next step without further purification. $^1$H NMR (400 MHz, CDCl$_3$) 3.70 (s, 3H), 3.21 (s, 3H), 1.50 (s, 6H); m/z=200.3 (M+H)$^+$.

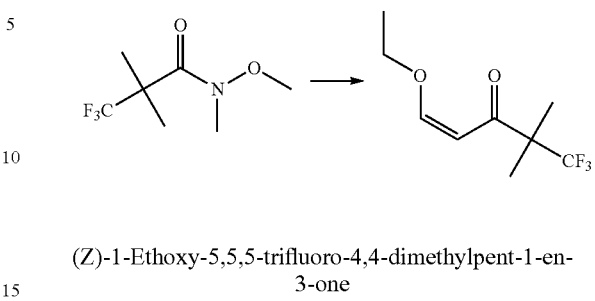

(Z)-1-Ethoxy-5,5,5-trifluoro-4,4-dimethylpent-1-en-3-one

A dried 250 mL flask was purged with nitrogen then charged with β-bromovinyl ethyl ether (3.52 g, 23.3 mmol) and tetrahydrofuran (46 mL) and the mixture was cooled to −78° C. 1.2 M tert-butyllithium in pentane (23.3 mL, 28.0 mmol) was added dropwise over 15 minutes and the mixture was stirred at −78° C. for 1.5 hours. A solution of 3,3,3-trifluoro-N-methoxy-N,2,2-trimethylpropanamide (0.93 g, 4.7 mmol) in tetrahydrofuran (10 mL) was added dropwise over 3 minutes and the mixture was stirred at −78° C. for 2.5 hours, then carefully quenched with 1M $NaH_2PO_4$ (50 mL). The mixture was diluted with water (50 mL) and extracted with ether (100 mL). The aqueous layer was diluted with additional water (100 mL) and extracted with ether (50 mL) and the combined organics were dried ($Na_2SO_4$), filtered and evaporated. The crude product was purified by silica chromatography (0-100% DCM in hexanes) to obtain the Z-enone as an oil (770 mg, 78%), which epimerized to the E-enone on standing overnight. $^1$H NMR (E-enone) (400 MHz, CDCl$_3$) 7.67 (d, J=12.0 Hz, 1H), 5.95 (d, J=12.0 Hz, 1H), 4.00 (q, J=7.1 Hz, 2H), 1.36 (t, J=7.1 Hz, 3H), 1.35 (s, 6H); m/z=211.3 (M+H)$^+$.

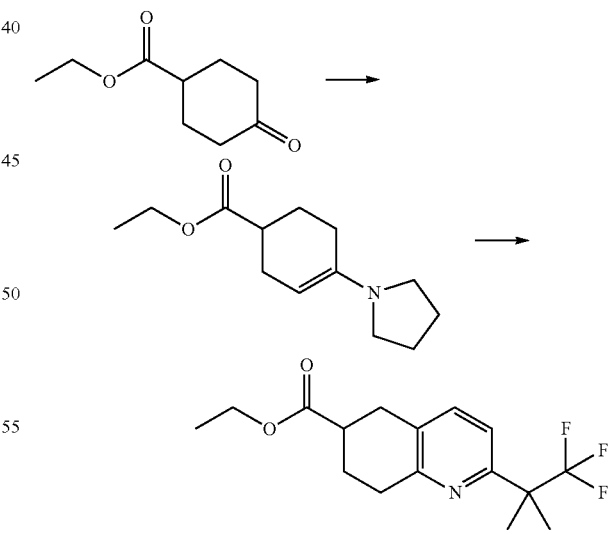

Ethyl 4-(pyrrolidin-1-yl)cyclohex-3-enecarboxylate and ethyl 2-(1,1,1-trifluoro-2-methylpropan-2-yl)-5,6,7,8-tetrahydroquinoline-6-carboxylate A mixture of ethyl 4-oxocyclohexanecarboxylate (2.35 g, 13.8 mmol), pyrrolidine (1.27 mL, 15.2 mmol) and benzene (34 mL) heated under reflux with azeotropic removal of water for 1.5 h, then concentrated in vacuo to afford crude enamine which was used directly in the next step.

The crude enamine (assumed 13.8 mmol) was dissolved in dry 1,4-dioxane (8 mL), and the mixture purged with N₂ and cooled to 6° C. A solution of (E)-1-ethoxy-5,5,5-trifluoro-4,4-dimethylpent-1-en-3-one (2.9 g, 14 mmol) in 1,4-dioxane (6 mL) was added and the mixture was heated at 70° C. for 20 h. Ammonium acetate (2.13 g, 27.6 mmol) was added and the mixture was heated at reflux. After 1 hr additional ammonium acetate (2.13 g, 27.6 mmol) was added and reflux continued for a further 2 h. The mixture was concentrated and the residue dissolved in EtOAc (100 mL), then washed with 1 M NaH₂PO₄ (2×25 mL). The combined aqueous washes were back extracted with EtOAc (25 mL) and the combined organic layers were dried (Na₂SO₄), filtered and evaporated to obtain a bright red oil which was absorbed on silica. Column chromatography on silica (0-20% EtOAc/hexanes) afforded the pyridine as oil (1.88 g, 43%). ¹H NMR (CDCl₃) 7.37 (d, J=8.1 Hz, 1H), 7.25 (d, J=8.1 Hz, 1H), 4.19 (q, J=7.1 Hz, 2H), 2.88-3.08 (m, 4H), 2.70-2.80 (m, 1H), 2.25-2.35 (m, 1H), 1.90-2.03 (m, 1H), 1.58 (s, 6H), 1.29 (t, J=7.1 Hz, 3H). m/z=316.0 (M+H)⁺.

Intermediates 2A and 2B (R)-2-(1,1,1-Trifluoro-2-methylpropan-2-yl)-5,6,7,8-tetrahydroquinoline-6-carboxylic acid, and (S)-2-(1,1,1-trifluoro-2-methylpropan-2-yl)-5,6,7,8-tetrahydroquinoline-6-carboxylic acid

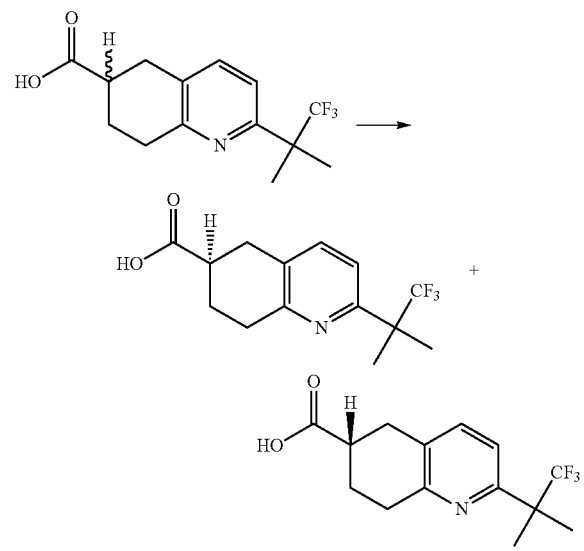

Separation by chiral HPLC: 2-(1,1,1-trifluoro-2-methylpropan-2-yl)-5,6,7,8-tetrahydroquinoline-6-carboxylic acid (0.720 g) was dissolved in 1/1 IPA/hexane (8 mL). 1100 uL injections were separated on a ChiralPak AD-H 5 um 250×20 mm ID at 0° C. eluting with 0.1% TFA in 96/4 hexane/IPA at 20 mL/min. Peaks eluted at 6.3 and 7.9 min, with UV monitoring at 230 nm. The solutions from the chiral separation were concentrated and each solid was separately dissolved in 20/1 DCM/MeOH (40 mL), and washed with 1 M pH 6 phosphate buffer (30 mL). The aqueous layers were back-extracted with DCM (2×15 mL), and the combined organic layers were dried (Na₂SO₄), filtered and concentrated to afford the resolved acids, each as solids (tentatively identified as (R)- (303 mg, 84%) and (S)- (292 mg, 81%) respectively. Analytical determination of ee: ChiralPak AD-H 250×4.6 mm ID, 5 um, 0.1% TFA in 96/4 hexane/IPA at 1 mL/min at ambient temperature, with UV analysis at 240 nm. Enantiomers eluted at 5.7 and 6.4 min, each with >99.5% ee and were assigned (R)- and (S)- respectively, based on an X-ray structure of the 4-bromophenyl anilide derivative of the first-eluting acid.

Intermediates 3A and 3B

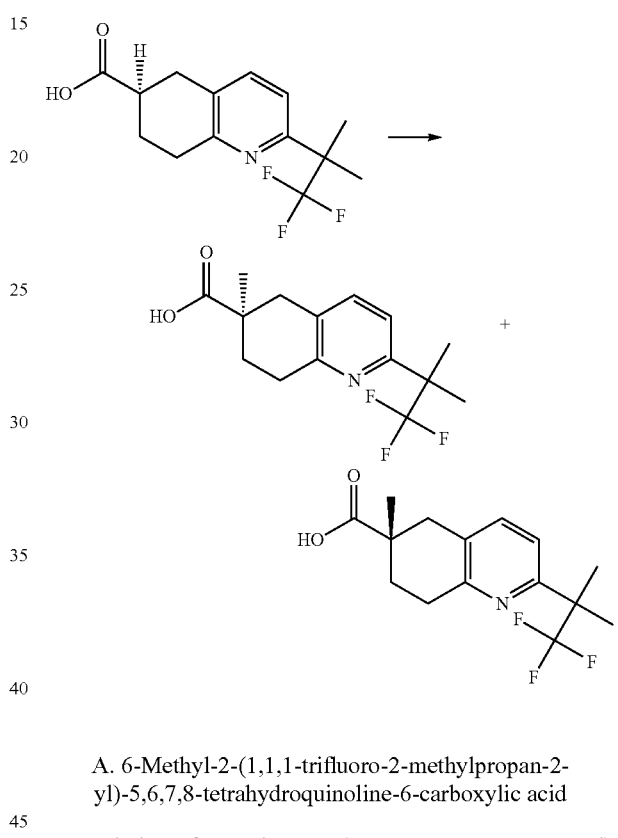

A. 6-Methyl-2-(1,1,1-trifluoro-2-methylpropan-2-yl)-5,6,7,8-tetrahydroquinoline-6-carboxylic acid A solution of LDA in THF (0.64 M, 4 mL, 2.56 mmol), prepared from N,N-diisopropylamine (358 µL, 2.56 mmol), 1.47 M of butyllithium in hexane (1.74 mL, 2.56 mmol) and THF (2 mL) was added dropwise to a 0° C. solution of (S)-2-(1,1,1-trifluoro-2-methylpropan-2-yl)-5,6,7,8-tetrahydroquinoline-6-carboxylic acid (294 mg, 1.02 mmol) in dry THF (4 mL). After 2 min at 0° C., the dark red mixture was warmed to room temperature, and aged for 1 h, before recooling to 0° C. Neat methyl iodide (159 µL, 2.56 mmol) was added, and the mixture rapidly lightened to pale red. After 2 min at 0° C., the mixture was warmed to room temperature. After 1 h, the reaction was quenched by addition of water (5 mL), then partitioned between 1M KH₂PO₄ (30 mL) and DCM (40 mL). The aqueous layer was extracted with DCM (2×20 mL), the combined organic layers were dried (Na₂SO₄), filtered and concentrated to a yellow semi-solid, which was purified by reverse-phase HPLC (40-75% ACN in 0.1% HCO₂H/H₂O). The combined purified fractions were concentrated to remove ACN, and the mixture buffered with 1M pH 6 phosphate buffer (30 mL), and extracted with DCM (3×20 mL). The combined organic layers were dried (Na₂SO₄), filtered and concentrated to afford the acid as a solid (104 mg, 34%). ¹H NMR (400 MHz, CDCl₃) δ 10.76 (br s, 1H), 7.35 (d, J=8.0 Hz, 1H), 7.25 (d, J=8.0 Hz, 1H), 3.25 (d, J=16.6 Hz, 1H), 2.99 (br s with fine str, 2H), 2.66 (d, J=16.6 Hz, 1H), 2.27 (app dt, J=12.7, 5.9 Hz, 1H), 1.90 (app dt, J=13.8, 7.1 Hz, 1H), 1.58 (s, 6JH), 1.36 (s, 3H); m/z=302.1 (M+H)+.

B. (R)-6-Methyl-2-(1,1,1-trifluoro-2-methylpropan-2-yl)-5,6,7,8-tetrahydroquinoline-6-carboxylic acid and (S)-6-methyl-2-(1,1,1-trifluoro-2-methylpropan-2-yl)-5,6,7,8-tetrahydroquinoline-6-carboxylic acid

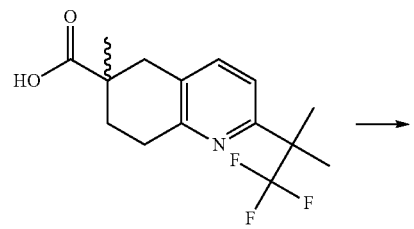

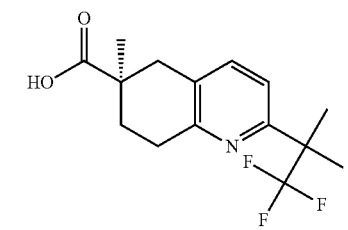

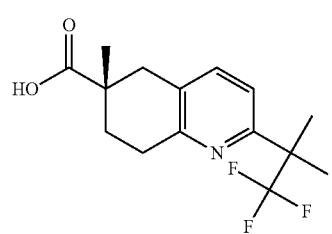

Separation by chiral HPLC: 6-methyl-2-(1,1,1-trifluoro-2-methylpropan-2-yl)-5,6,7,8-tetrahydroquinoline-6-carboxylic acid (96 mg, 0.32 mmol) was dissolved in 1/1 IPA/hexane (4 mL). 1000 uL injections were separated on a ChiralPak AD-H 5 um 250×20 mm ID at 0° C. eluting with 0.1% TFA in 96/4 hexane/IPA at 20 mL/min. Peaks eluted at 7.8 and 10.0 min, with UV monitoring at 254 nm. The solutions from the chiral separation were concentrated, and each residue was separately dissolved in 20/1 DCM/MeOH (30 mL), and washed with 1 M pH 6 phosphate buffer (20 mL). The aqueous layer was back-extracted with DCM (2×20 mL), and the combined organic layers were dried (Na₂SO₄), filtered and concentrated to afford the resolved acids, each as a solid (tentatively assigned as the (R)- (29 mg, 60%) and (S)- (43 mg, 90%) enantiomers respectively).

Intermediate 4A (R)-1-(1H-Indazol-5-yl)ethanamine dihydrochloride

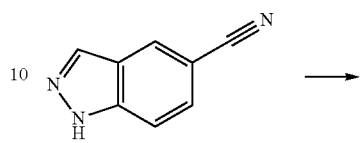

A. 1-(Tetrahydro-2H-pyran-2-yl)-1H-indazole-5-carbonitrile

1H-Indazole-5-carbonitrile (4.29 g, 30.0 mmol), dihydropyran (11 mL) and p-toluenesulfonic acid monohydrate (570 mg, 3.0 mmol) were combined in THF (40 mL) and heated to reflux. After 19 h, the mixture was allowed to cool to room temperature, and concentrated to a brown oil, which was absorbed on silica. Chromatography on silica (0-25% EtOAc/hexanes) afforded impure nitrile as an oil (4.84 g, 71%), which was carried forward to the next step without additional purification. ¹H NMR (400 MHz, CDCl₃) δ 8.14-8.11 (m, 2H), 7.71 (d, J=8.7 Hz, 1H), 7.59 (d, J=8.7 Hz, 1H), 5.76 (dd, J=2.6, 9.2 Hz, 1H), 4.07-4.00 (m, 1H), 3.78-3.72 (m, 1H), 2.59-2.31 (m, 2H), 2.19-2.07 (m, 2H), 1.86-1.55 (m, 2H); m/z=228.4 (M+H)⁺.

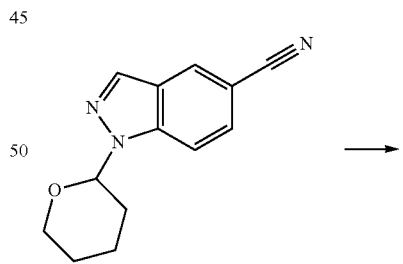

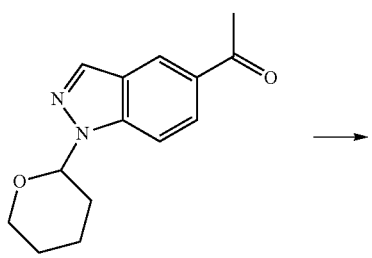

B. 1-(1-(Tetrahydro-2H-pyran-2-yl)-1H-indazol-5-yl)ethanone and 1-(1H-indazol-5-yl)ethanone

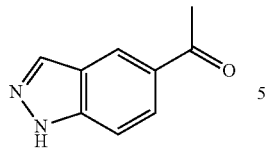

A 250 mL flask charged with 1-(tetrahydro-2H-pyran-2-yl)-1H-indazole-5-carbonitrile (4.84 g, 14.9 mmol) and THF (50 mL) was cooled to 0° C. under nitrogen, and a solution of 3.0 M of methylmagnesium bromide in ether (25 mL, 75 mmol) was added dropwise over 2 min. After addition was complete, the mixture was warmed to room temperature for 5 min, then heated to reflux. The mixture was removed from the heat after 3.5 h, cooled in ice, and water (20 mL) added dropwise, followed by 1M NH$_4$Cl (100 mL). The mixture was extracted with EtOAc (2×50 mL), and the combined organic layers were dried (Na$_2$SO$_4$), filtered and concentrated to afford the intermediate methyl ketone as an oil (crude 5.20 g), which was carried forward without further purification.

Concentrated hydrochloric acid (6 mL) was added dropwise to a solution of the ketone (5.20 g) in methanol (50 mL), which darkened immediately from yellow to dark green. After 3 h 2M HCl (30 mL, 60 mmol) was added, and the mixture placed in an oil bath at 50° C. The mixture was removed from the heat after 5.5 h, and poured into 2M Na$_2$CO$_3$ (80 mL). The cloudy brown suspension (pH 10) was diluted with water (100 mL), and extracted with CHCl$_3$ (3×100 mL). The combined organic layers were dried (Na$_2$SO$_4$), filtered and concentrated to a solid (7.6 g). Trituration with CHCl$_3$ (50 mL) afforded the ketone as a solid (0.73 g, 30%). The filtrate was absorbed on silica. Chromatography on silica (10-100% EtOAc/hexane) afforded additional ketone as a solid (1.29 g, 54%). Net weight recovered (2.02 g, 85%; 42% over 3 steps). $^1$H NMR (400 MHz, CDCl$_3$) δ 8.46 (s, with fine str, 1H), 8.24 (s, 1H), 8.09 (dd, J=1.4, 8.8 Hz, 1H), 7.57 (d, J=8.8 Hz, 1H), 2.70 (s, 3H); m/z=161.1 (M+H)$^+$.

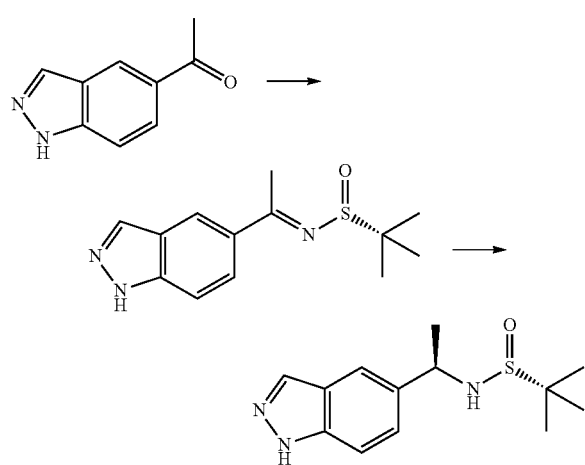

C. (S,E)-N-(1-(1H-indazol-5-yl)ethylidene)-2-methylpropane-2-sulfinamide and (S)—N—((R)-1-(1H-indazol-5-yl)ethyl)-2-methylpropane-2-sulfinamide A 250 mL flask was charged with 1-(1H-indazol-5-yl)ethanone (1.29 g, 8.05 mmol), (R)-2-methylpropane-2-sulfinamide (1.07 g, 8.83 mmol), tetraethoxytitanium (3.3 mL, 16 mmol) and THF (40 mL), and the mixture was heated at reflux overnight. After 17.5 h, additional (R)-2-methylpropane-2-sulfinamide (0.50 g, 0.5 equiv.) and tetraethoxytitanium (3.3 mL, 2.0 equiv) were added, and reflux continued for an additional 30 h. The mixture was cooled to −40° C., then added dropwise via cannula to a suspension of powdered sodium tetrahydroborate (1.5 g, 40 mmol) in THF (20 mL) at −40° C. (MeCN/CO$_2$ slush) over 20 min. The mixture was stirred at −40° C. for at least another 2 h, and allowed to warm to room temperature overnight. After 14 h, the mixture was cooled to 0° C., and methanol (10 mL) was added to quench NaBH$_4$, before the solution was added dropwise to stirred brine (80 mL). The resulting suspension was mixed with Celite, filtered through Celite and the filter cake washed with EtOAc (250 mL). The biphasic filtrate was brought to pH 6 with 1M NaH$_2$PO$_4$ (40 mL), and the mixture washed with brine (200 mL). The organic layer was dried (Na$_2$SO$_4$), filtered and concentrated to a cloudy yellow gum, which was absorbed on silica. Chromatography on silica (20-100% EtOAc/hexane) afforded crude sulfinamide as a gum (1.82 g), which partially solidified on standing. Recrystallization from EtOAc/hexane (10 mL/18 mL) afforded the desired sulfinamide as a solid (0.87 g, 41% over 2 steps, 94% de by $^1$H NMR). $^1$H NMR (400 MHz, DMSO-d$_6$) δ 13.00 (s, 1H), 8.04 (s, 1H), 7.72 (s, 1H), 7.49 (d, J=8.6 Hz, 1H), 7.40 (dd, J=1.5, 8.6 Hz, 1H), 5.60 (d, J=6.7 Hz, 1H), 4.47 (app pentet, J=6.7 Hz, 1H), 1.45 (d, J-6.7 Hz, 3H), 1.12 (s, 9H); m/z=266.2 (M+H)$^+$.

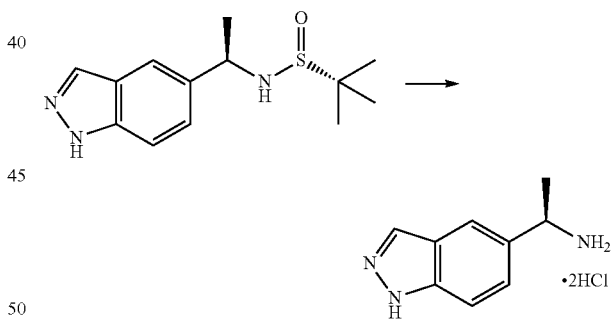

D. (R)-1-(1H-indazol-5-yl)ethanamine dihydrochloride

A 50 mL flask was charged with (S)—N—((R)-1-(1H-indazol-5-yl)ethyl)-2-methylpropane-2-sulfinamide (0.83 g, 3.1 mmol) and methanol (2.4 mL). 4.0 M of hydrogen chloride in 1,4-dioxane (2.4 mL, 9.6 mmol) was added to the resultant solution, which rapidly deposited a thick precipitate. After 20 min, the mixture was diluted with ether (30 mL), filtered and the filter cake washed with ether and dried to afford the amine bis-hydrochloride salt (708 mg, 97%) as a solid. $^1$H NMR (400 MHz, DMSO-d$_6$) δ 8.8 (br s, 1H), 8.59 (br s, 3H), 8.12 (d, J=0.8 Hz, 1H), 7.90 (s, 1H), 7.60 (d, J=8.7

Hz, 1H), 7.53 (dd, J=1.6, 8.7 Hz, 1H), 4.49 (app heptet, J=z6.0 Hz, 1H), 1.58 (d, J=6.7 Hz, 3H); m/z=162.6 (M+H)⁺.

Intermediate 4B

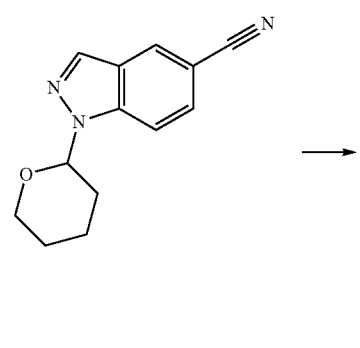

1-(1-(Tetrahydro-2H-pyran-2-yl)-1H-indazol-5-yl)ethanamine

A solution of MeMgBr in Et₂O (15.2 mL; 4 eq) was added dropwise at 0° C. to a stirred solution of 1-(tetrahydro-2H-pyran-2-yl)-1H-indazole-5-carbonitrile (2.59 g, 11.4 mmol) in tetrahydrofuran (170 mL) under nitrogen. After complete addition, the mixture was heated to reflux and was stirred for 2 hr. The mixture was the cooled to 0° C. and methanol (90 mL) was added followed by sodium tetrahydroborate (650 mg, 17 mmol). The mixture was stirred at 0° C. for approximately 2 hours then hydrolysed by addition of solid NH₄Cl (2.5 g) and H₂O (2 mL). The mixture was stirred at room temperature for 1 hour then filtered and the filtrate concentrated under vacuum. The residue was triturated with MeOH and filtered—the filter cake was washed with small amounts of MeOH (filter cake is NH₄Cl). Silica gel was added to the filtrate which was concentrated under vacuum (i.e. compound dry-loaded on to silica) and then purified by column chromatography on silica gel using 0-10% of MeOH—NH₄OH (97:3)/EtOAc as eluent to give the product (1.8 g) which contained ca. 50 mol % of NH₄Cl. The compound was purified further by preparative high performance liquid chromatography to give the product (1.1 g) as an oil. ¹H NMR (400 MHz; CDCl₃) δ 7.99 (s, 1H), 7.66 (s, 1H), 7.55 (d, J=8.8 Hz, 1H), 7.41 (d, J=8.8 Hz, 1H), 5.70 (dd, J=9.2, 2.8 Hz, 1H), 4.23 (q, J=6.7 Hz, 1H), 4.06-4.00 (m, 1H), 3.78-3.71 (m, 1H), 2.62-2.53 (m, 1H), 2.20-2.11 (m, 1H), 2.10-2.03 (m, 1H), 1.81-1.61 (m, 5H), 1.43 (d, J=6.5 Hz, 3H).

Intermediate 5

6-Trifluoromethyl-3,4-dihydro-2H-benzo[1,4]oxazine-2-carboxylic acid

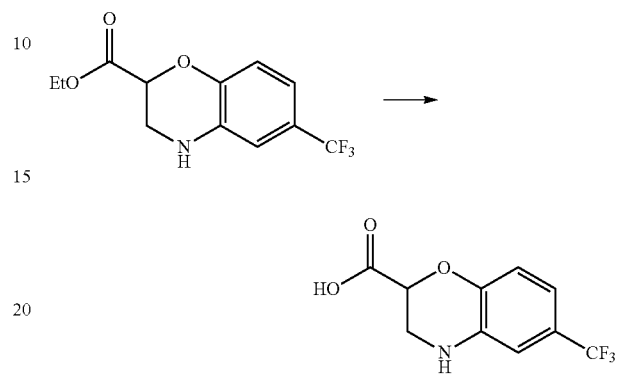

a. 6-Trifluoromethyl-3,4-dihydro-2H-benzo[1,4]oxazine-2-carboxylic acid

6-Trifluoromethyl-3,4-dihydro-2H-benzo[1,4]oxazine-2-carboxylic acid ethyl ester (500 mg, 2 mmol) was dissolved in 1,4-dioxane (20 mL). Sodium hydroxide (109 mg, 2.7 mmol) was added, followed by benzyl chloroformate (311 μL, 2.2 mmol), and the reaction stirred overnight at room temperature. The reaction mixture was acidified with 2N HCl and diluted with water (20 mL), then extracted with EtOAc (3×30 mL). The combined organics were washed with brine (2×40 mL), dried (MgSO₄), filtered and concentrated. Trituration using DCM/hexanes gave the title compound (330 mg, 10%) as a pale brown solid. m/z=245.7 (M−1), r.t.=2.78 mins. ¹H NMR (400 MHz; CDCl₃) δ 7.01 (2H, s), 6.86 (1H, s), 4.94 (1H, t), 3.66 (2H, dd).

Intermediate 6

4-Methyl-6-trifluoromethyl-3,4-dihydro-2H-benzo[1,4]oxazine-2-carboxylic acid a. 4-Methyl-6-trifluoromethyl-3,4-dihydro-2H-benzo[1,4]oxazine-2-carboxylic acid To a solution of 6-trifluoromethyl-3,4-dihydro-2H-benzo[1,4]oxazine-2-carboxylic acid ethyl ester (650 mg, 2.4 mmol) in anhydrous DMF (7 mL) was added K$_2$CO$_3$ (816 mg, 5.9 mmol), followed by iodomethane (294 µL, 4.7 mmol). The reaction was heated in the microwave (300 W, 150° C.) for 1 hour. After cooling, the mixture was poured into water (50 mL), acidified with 2N HCl and extracted with EtOAc (3×50 mL). The combined organics were washed with brine (3×50 mL), dried (MgSO$_4$), filtered and concentrated. Flash chromatography (0 to 12% MeOH in DCM) gave the title compound (90 mg, 10%) as a beige solid. m/z=262.1 (M+1), r.t.=3.28 mins. $^1$H NMR (400 MHz; d$_6$-DMSO) δ 6.93-6.86 (3H, m), 4.85 (1H, s), 3.45-3.36 (2H, m), 2.86 (3H, s).

Intermediate 7

6-Trifluoromethoxy-2H-chromene-3-carboxylic acid

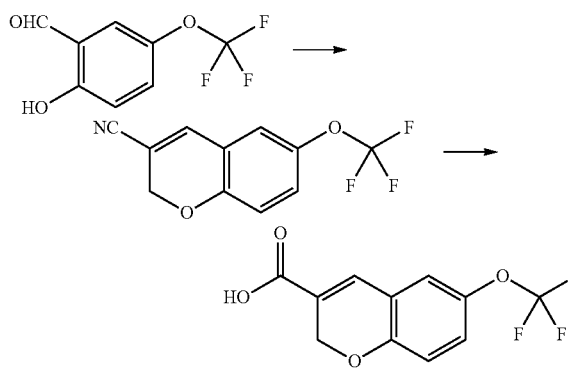

6-Trifluoromethoxy-2H-chromene-3-carbonitrile

To a microwave tube was added 2-hydroxy-5-trifluoromethoxybenzaldehyde (1 g, 5.0 mmol), 2-propenenitrile (1.6 mL, 24.3 mmol) and triethylenediamine (136 mg, 1.2 mmol). The reaction was heated in the microwave at 130° C. for 1 hour. After cooling, the resulting solution was diluted with ether (100 mL) and washed with 1N NaOH (50 mL), 1N HCl (50 mL) and brine (50 mL), dried (MgSO$_4$), filtered and concentrated. Flash chromatography (0 to 15% EtOAc in hexanes over 1 hour) gave the product (600 mg) as a solid. m/z=242.4 (M+1), r.t.=3.72 mins. $^1$H NMR (400 MHz; CDCl$_3$) δ 7.14-7.12 (2H, m), 7.00 (1H, s), 6.89 (1H, d), 4.85 (2H, s).

6-Trifluoromethoxy-2H-chromene-3-carboxylic acid

To a microwave vial was added 6-trifluoromethoxy-2H-chromene-3-carbonitrile (100 mg, 0.4 mmol) and 10 M of sodium hydroxide in water (2 mL, 20 mmol). The reaction mixture was heated at 150° C. for 10 minutes in the microwave. The reaction mixture was acidified with conc. HCl then extracted with EtOAc (3×30 mL). The combined organics were washed with brine (3×30 mL), dried (MgSO$_4$), filtered and concentrated, to give the product (42 mg) as a solid. m/z=258.9 (M−1), r.t.=3.43 mins. $^1$H NMR (400 MHz; CDCl$_3$) δ 7.50 (1H, s), 7.11 (1H, dd), 7.04 (1H, d), 6.84 (1H, d), 5.02 (2H, d).

Intermediate 8

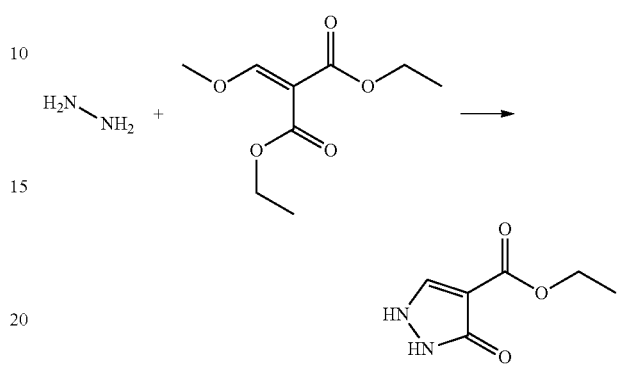

3-Oxo-2,3-dihydro-1H-pyrazole-4-carboxylic acid ethyl ester

To a solution of sodium ethoxide (20.8 g, 0.31 mol) and diethyl ethoxymethylenemalonate (20 mL, 0.10 mol) in ethanol (400 mL), was added hydrazine monohydrate (10.0 mL, 0.20 mol) with cooling in an ice-cold water bath. The mixture was then heated at 80° C. for 3 h. The resulting mixture was diluted with water (200 mL) and neutralized with 10M HCl solution until pH 6. The mixture was extracted several times with chloroform. The aqueous layer was acidified to pH 2 and extracted again with chloroform. The combined organic layers were dried (Na$_2$SO$_4$) and concentrated to a solid which was washed with methanol and ether and dried to give the product (13.2 g, 80%) as a solid. $^1$H NMR (400 MHz, DMSO-d$_6$) δ 7.89 (s, 1H), 4.15 (q, 2H, J=7.12 Hz), 1.23 (t, 3H, J=7.11 Hz).

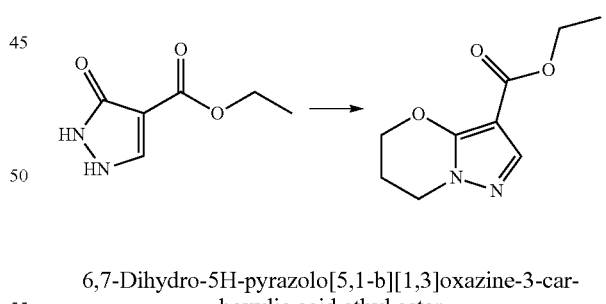

6,7-Dihydro-5H-pyrazolo[5,1-b][1,3]oxazine-3-carboxylic acid ethyl ester

3-Oxo-2,3-dihydro-1H-pyrazole-4-carboxylic acid ethyl ester (13.2 g, 84.5 mmol), potassium carbonate (50 g, 0.3 mol) and N,N-dimethylformamide (500 mL) were combined in a 250 mL round bottom flask, and the mixture was heated to 130° C. 1,2-Dibromo-propane (10.4 mL, 0.10 mol) was added. After 30 minutes, the mixture was partitioned between DCM and water. The aqueous layer was extracted with DCM and the combined organics were washed with brine, dried (Na$_2$SO$_4$), filtered and concentrated in vacuo. The yellow solid was purified by column chromatography (DCM/MeOH) to afford the ester (9.67 g, 58%) as a solid. $^1$H NMR (400 MHz, DMSO-d$_6$) δ7.62 (s, 1H), 4.41-4.38 (m, 2H), 4.13 (q, 2H), 4.08 (t, 2H, J=6.03 Hz), 2.21-2.15 (m, 2H), 1.21 (t, 3H, J=7.09 Hz).

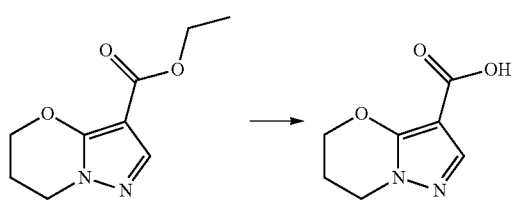

6,7-Dihydro-5H-pyrazolo[5,1-b][1,3]oxazine-3-carboxylic acid

A solution of 6,7-dihydro-5H-pyrazolo[5,1-b][1,3]oxazine-3-carboxylic acid ethyl ester (9.67 g, 49.3 mmol) in tetrahydrofuran (150 mL), ethanol (50 mL) and 1M of lithium hydroxide in water (148 mL, 148 mmol) was stirred at 60° C. for 2 days. After cooling, the volatiles were removed. The residue was transferred to an Erlenmeyer flask and ice was added. The reaction was acidified to pH 2 with 10M HCl. The aqueous layer was extracted several times with 3/1 chloroform/IPA. The combined organic layers were dried (Na$_2$SO$_4$), filtered, concentrated to afford the acid as a solid (8.14 g, 98%). $^1$H NMR (400 MHz, DMSO-d$_6$) δ7.57 (s, 1H), 4.37 (t, 2H, J=5.29 Hz), 4.07 (t, 2H, J=6.11 Hz), 2.20-2.15 (m, 2H).

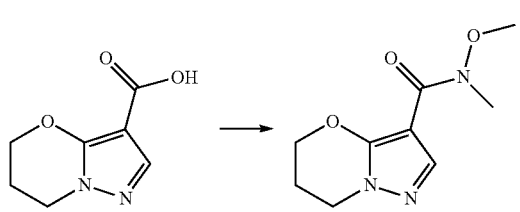

6,7-Dihydro-5H-pyrazolo[5,1-b][1,3]oxazine-3-carboxylic acid methoxy-methyl-amide To a stirred solution of 6,7-dihydro-5H-pyrazolo[5,1-b][1,3]oxazine-3-carboxylic acid (8.14 g, 48.4 mmol), N-(3-dimethylaminopropyl)-N'-ethylcarbodiimide hydrochloride (10.21 g, 53.3 mmol), 1-hydroxybenzotriazole hydrate (8.16 g, 53.3 mmol), 4-dimethylaminopyridine (300 mg, 2 mmol), and DIPEA (16.5 mL, 97 mmol) in anhydrous acetonitrile (200 mL) was added a solution of N,O-dimethylhydroxylamine hydrochloride (9.44 g, 97 mmol) and DIPEA (16.5 mL, 97 mmol) in anhydrous acetonitrile (100 mL). The mixture was stirred for 3 days at room temperature, then poured into saturated NaHCO$_3$ solution (200 mL) and extracted with EtOAc (3×1000 mL). The combined organic layers were washed with brine (200 mL), dried (Na$_2$SO$_4$), filtered and concentrated. Flash chromatography (0 to 5% MeOH in DCM) afforded the amide as a solid (9.02 g, 88%). $^1$H NMR (400 MHz, DMSO-d$_6$) δ7.62 (s, 1H), 4.35 (t, 2H, J=5.24 Hz), 4.08 (t, 2H, J=6.20 Hz), 3.63 (s, 3H), 3.12 (s, 3H), 2.20-2.15 (m, 2H).

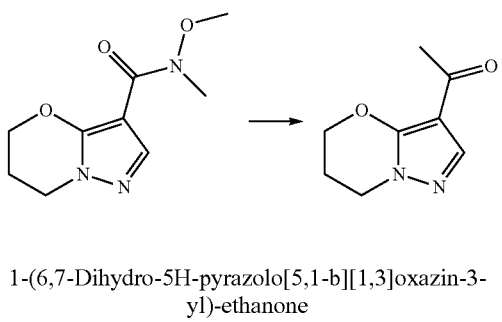

1-(6,7-Dihydro-5H-pyrazolo[5,1-b][1,3]oxazin-3-yl)-ethanone

A solution of 6,7-dihydro-5H-pyrazolo[5,1-b][1,3]oxazine-3-carboxylic acid methoxy-methyl-amide (9.02 g, 42.7 mmol) in tetrahydrofuran (300 mL) was cooled to 0° C. 3 M methylmagnesium bromide in ether (15.3 mL, 43 mmol) was added and the reaction was stirred at 0° C. for 30 minutes, then warmed to room temperature. Additional 3 M methylmagnesium bromide in ether (15.3 mL, 43 mmol) was added after 1 hour, and the mixture was stirred at room temperature overnight, then the volatiles were removed in vacuo. The residue was partitioned between EtOAc (100 mL) and saturated NaHCO$_3$ solution (150 mL). The aqueous layer was extracted with EtOAc (2×100 mL), and the combined organic layers were washed with brine (3×50 mL), dried (Na$_2$SO$_4$), filtered and concentrated. Flash chromatography (0 to 4% MeOH in DCM) afforded the ketone (5.79 g, 82%) as a solid. $^1$H NMR (400 MHz, DMSO-d$_6$) δ7.69 (s, 1H), 4.44 (t, 2H, J=5.25 Hz), 4.09 (t, 2H, J=6.10 Hz), 2.23 (s, 3H), 2.22-2.17 (m, 2H).

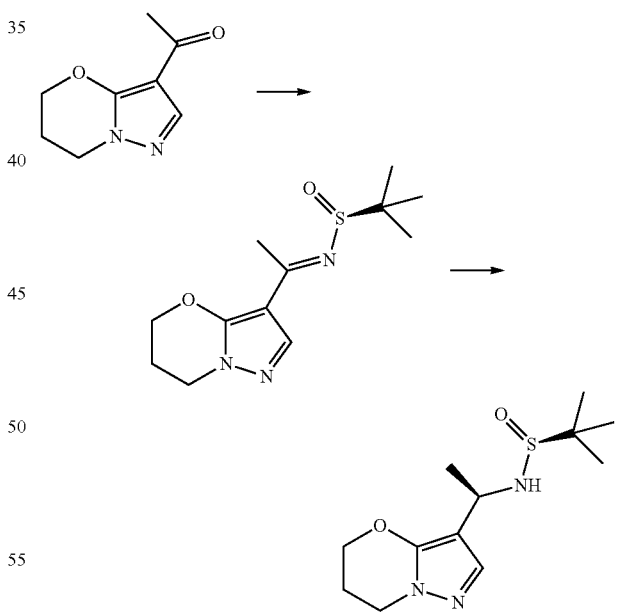

2-Methyl-propane-2-sulfinic acid [1-(6,7-dihydro-5H-pyrazolo[5,1-b][1,3]oxazin-3-yl)-eth-(E)-ylidene]-amide and 2-methyl-propane-2-sulfinic acid [(R)-1-(6,7-dihydro-5H-pyrazolo[5,1-b][1,3]oxazin-3-yl)-ethyl]-amide A 45 mL pressure vessel was charged with 1-(6,7-dihydro-5H-pyrazolo[5,1-b][1,3]oxazin-3-yl)-ethanone (0.148 g, 0.891 mmol), (S)-(−)-2-methylpropane-2-sulfinamide (0.17 g, 1.4 mmol) and tetraethoxytitanium (3.5 mL, 17 mmol), and the mixture placed in an oil bath at 110° C. After 16 h the mixture was diluted with THF (20 mL) and poured slowly into brine (17 mL; 1 mL/mmol Ti). The resulting suspension was filtered through Celite, and the filter cake washed with EtOAc (100 mL). The filtrate was washed with brine (50 mL), dried (Na$_2$SO$_4$), filtered and concentrated to afford the crude ketimine as an oil (306 mg), which solidified on standing. The product was carried forward to the next step without additional purification. m/z=270.5 (M+H)$^+$.

A 50 mL flask was charged with 2-methyl-propane-2-sulfinic acid [1-(6,7-dihydro-5H-pyrazolo[5,1-b][1,3]oxazin-3-yl)-eth-(E)-ylidene]-amide (0.24 g, 0.89 mmol), purged with nitrogen, and tetrahydrofuran (5 mL) added. The resulting solution was cooled to 0° C., and 1.0 M of L-selectride in tetrahydrofuran (1.8 mL, 1.8 mmol) added dropwise over 4 min. After 1 h, water (0.3 mL) was added, and the mixture was concentrated and the residue absorbed on silica (1.5 g). Chromatography on silica (0-25% MeOH/EtOAc) afforded the sulfinamide (151 mg, 62% over 2 steps) as an oil. $^1$H NMR (400 MHz, CDCl$_3$) δ 7.26 (s, 1H), 4.48-4.41 (m, 1H), 4.33-4.23 (m, 2H), 4.16 (t, J=6.2 Hz, 2H), 3.29 (br d, J=5.0 Hz, 1H), 2.29-2.19 (m, 2H), 1.51 (d, J=6.7 Hz, 3H), 1.19 (s, 9H); m/z=272.5 (M+H)$^+$.

(R)-1-(6,7-dihydro-5H-pyrazolo[5,1-b][1,3]oxazin-3-yl)ethanamine dihydrochloride A stirred solution of 2-methyl-propane-2-sulfinic acid [(R)-1-(6,7-dihydro-5H-pyrazolo[5,1-b][1,3]oxazin-3-yl)-ethyl]-amide (151 mg, 0.56 mmol) in 1,4-dioxane (1 mL) and methanol (0.4 mL) was treated with 4.0 M of hydrogen chloride in 1,4-dioxane (0.42 mL, 1.7 mmol). The mixture became briefly cloudy, and then clarified. After 10 min the biphasic mixture was diluted with ether (15 mL), and the mixture sonicated to encourage solidification of the deposited gum. The suspension was stirred for an additional 10 min, whereupon it clarified. The solution was decanted, and the residue was dried under vacuum to afford the amine hydrochloride as a solid foam (158 mg, 118%). The material was carried forward to the next step without additional purification. $^1$H NMR (400 MHz, DMSO-d$_6$) δ 8.21 (br s, 3H), 7.44 (s, 1H), 4.32 (dd, J=4.0, 5.6 Hz, 2H), 4.16 (app pentet, J=6.0 Hz, 1H), 4.07 (t, J=6.2 Hz, 2H), 2.20-2.12 (m, 2H), 1.45 (d, J=6.9 Hz, 3H); m/z=168.3 (M+H)$^+$.

Intermediate 9

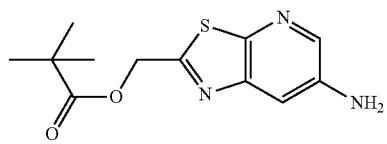

(6-Aminothiazolo[5,4-b]pyridin-2-yl)methyl pivalate

Prepared using procedure documented in WO2007100758.

Intermediates 10 and 11

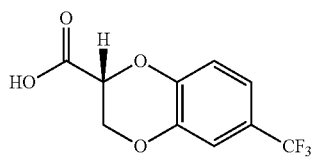

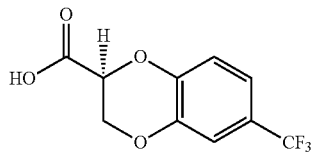

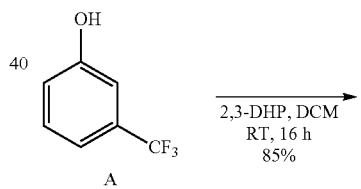

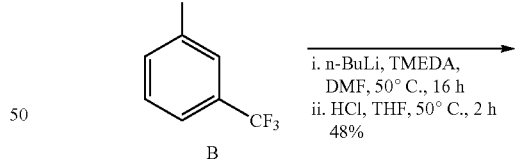

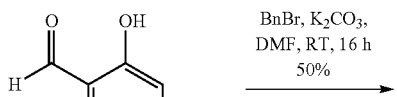

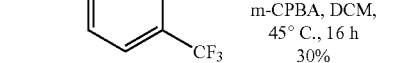

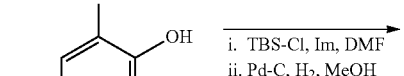

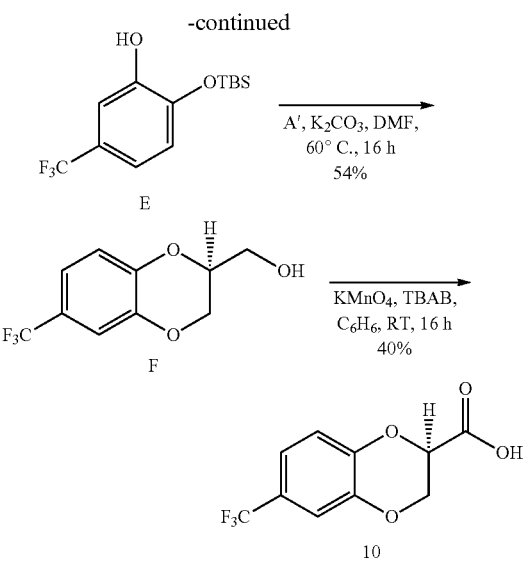

2-(3-Trifluoromethyl-phenoxy)-tetrahydropyran B

To a stirring solution of 3-trifluoromethylphenol A (37.0 g, 228.0 mmol) in dry DCM was added THP (47.96 g, 570 mmol) at RT under nitrogen atmosphere. To the resultant reaction mixture catalytic amount of 4 M HCl in dioxane was added and the reaction mixture was stirred at RT for 16 h. After completion of the reaction (TLC), the reaction mixture was diluted with DCM and washed with NaHCO₃ solution. The organic layer was dried over Na₂SO₄ and concentrated under reduced pressure. Purification by flash chromatography (SiO₂, 60-120 mesh, 2% EtOAc in Petroleum ether) afforded title compound B as a pale yellow liquid (48 g, 85%). $^1$H NMR (CDCl₃; 300 MHz) δ 1.55-1.76 (m, 3H), 1.85-1.89 (m, 2H), 1.92-2.06 (m, 1H), 3.60-3.64 (m, 1H), 3.83-3.91 (m, 1H), 5.44-5.46 (m, 1H), 7.21-7.40 (m, 4H).

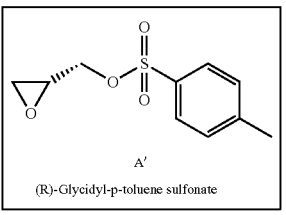

(R)-Glycidyl-p-toluene sulfonate

2-Hydroxy-4-trifluoromethylbenzaldehyde C n-BuLi (40 mL, 1.6 M) was added drop wise at −10° C. under nitrogen atmosphere to TMEDA (11.88 g, 102 mmol) and stirred for 30 min, then compound B was added slowly by maintaining the reaction at −10° C. After 2 h DMF (5 mL) was added and the resultant reaction mixture was stirred at 50° C. for 16 h. After completion of the reaction (TLC), the reaction mixture was diluted with water and extracted with EtOAc (3×). The organic layer was dried over anhy. Na₂SO₄ and concentrated under reduced pressure. The obtained residue was dissolved in THF (100 mL) and dil HCl (32 mL in 21 mL of water) was added. The resultant mixture was stirred for 2 h at 50° C. After that the reaction mixture was extracted with EtOAc (3×) and the combined organic layers were washed with brine and dried over Na₂SO₄ and concentrated under reduced pressure. Purification by flash chromatography (SiO₂, 60-120 mesh, 2% EtOAc in Petroleum ether) afforded title compound C as a pale yellow liquid (6.7 g, 48%). $^1$H NMR (CDCl₃; 300 MHz) δ 7.20-7.30 (m, 1H), 7.69-7.73 (m, 2H), 9.99 (s, 1H), 11.0 (s, 1H); MS: [M−1]⁺=189.

2-Benzyloxy-4-trifluoromethyl-phenol D

Step 1: 2-Benzyloxy-4-trifluoromethyl-benzaldehyde

To a stirring solution of compound C (10.0 g, 52 mmol) in dry DCM (60 mL) were added K₂CO₃ (8.84 g, 63 mmol) and benzylbromide (7.45 mL, 63.0 mmol) at RT and the resultant reaction mixture was stirred at RT for 16 h. After completion of the reaction (TLC), the reaction mixture was diluted with EtOAc, washed with water and brine solution. The EtOAc layer was dried over anhy. Na₂SO₄ and concentrated under reduced pressure. Purification by flash chromatography (SiO₂, 60-120 mesh, 1% EtOAc in Petroleum ether) afforded the title compound as a solid (7.3 g, 50%). $^1$H NMR (CDCl₃; 300 MHz) δ 5.23 (s, 2H), 7.25-7.37 (m, 2H), 7.40-7.46 (m, 5H), 7.95 (d, 1H, J=8.3 Hz), 10.55 (s, 1H).

Step 2: 2-Benzyloxy-4-trifluoromethyl-phenol D

To a stirring solution of 2-benzyloxy-4-trifluoromethyl-benzaldehyde (40 g, 142 mmol) in dry DCM (600 mL) was added m-CPBA (60%, 98.2 g, 571 mmol) portion wise at RT under nitrogen atmosphere and the reaction mixture was heated to reflux for 16 h. After completion of the reaction, the reaction mixture was diluted with DCM and washed with sat NaHCO₃ solution. The DCM layer was dried over Na₂SO₄ and concentrated under reduced pressure. Purification by flash chromatography (SiO₂, 60-120 mesh, 5% EtOAc in Petroleum ether) afforded the title compound D as a solid (11.40 g, 30%). $^1$H NMR (CDCl₃; 300 MHz) δ 5.13 (s, 2H), 5.91 (s, 1H), 6.99 (d, 1H; J=8.3 Hz), 7.17-7.28 (m, 2H), 7.38-7.47 (m, 5H); MS: [M−1]⁺=267.

2-(tert-Butyldimethylsilyloxy)-5-trifluoromethylphenol E

To a stirring solution of compound D (15.0 g, 55.9 mmol) in dry DMF (100 mL) at RT was added imidazole (11.4 g, 167.0 mmol) and after 30 min TBDMS-Cl (25.3 g, 167.0 mmol) was added and the resultant reaction mixture was heated to 60° C. for 16 h. After completion of the reaction (TLC), the reaction mixture was diluted with EtOAc and washed with water and sat. NaHCO₃ solution. The combined EtOAc layers were dried over Na₂SO₄ and concentrated under reduced pressure to afford 13.5 g of crude product. To a solution of the above crude product in MeOH (100 mL) was added Pd—C (1.35 g) and the resultant reaction mixture was stirred under hydrogen atmosphere for 1 h at RT. After completion of the reaction (TLC), the reaction mixture was filtered through celite bed and the filtrate was concentrated under reduced pressure to afford compound E as a solid (6.7 g, 41% yield). $^1$H NMR (CDCl₃; 300 MHz) δ 0.17 (s, 6H), 0.96 (s, 9H), 6.92-7.20 (m, 3H-1).

(S)-(6-(trifluoromethyl)-2,3-dihydrobenzo[b][1,4]dioxin-2-yl)methanol F

To a stirring solution of compound E (5.0 g, 17.0 mmol) in DMF (15 mL) were added K₂CO₃ (11.98 g, 85 mmol) and (R)-Glycidyl-p-toluene sulfonate (A') (3.9 g, 17 mmol) (2.5 g, 11.0 mmol) and the resulting reaction mixture was heated to 60° C. for 16 h. After completion of reaction (TLC), the reaction mixture was cooled to RT, diluted with water (50 mL) and extracted with EtOAc (3×). The combined EtOAc layers were washed with brine, dried over anhy. Na$_2$SO$_4$ and concentrated under reduced pressure. Purification by flash chromatography (SiO$_2$, 60-120 mesh, 3% EtOAc in Petroleum ether) afforded compound F as a solid (2.1 g, 54%). $^1$H NMR (CDCl$_3$; 300 MHz) δ 1.89 (t, 1H; J=6.3 MHz), 3.86-3.94 (m, 2H), 4.13-4.19 (m, 1H), 4.28-4.39 (m, 2H), 6.95-6.99 (m, 1H), 7.11-7.18 (m, 2H).

(R)-6-(trifluoromethyl)-2,3-dihydrobenzo[b][1,4]dioxine-2-carboxylic acid 10

To a stirring solution of compound F (2.5 g, 10.0 mmol) in benzene (17 mL) at 10° C. were added aq KMnO$_4$ (3.37 g, 21 mmol) and TBAB (343 mg, 1 mmol) and the resultant reaction mixture was stirred at RT for 16 h. After completion of the reaction (TLC), the reaction mixture was filtered through celite and washed with EtOAc. The pH of the filtrate was adjusted to 2 with conc. HCl. The aqueous layer was extracted with EtOAc (3×), the combined EtOAc layer were dried over anhy. Na$_2$SO$_4$ and concentrated under reduced pressure to afford the title compound 10 as a solid (1.1 g, 40%). $^1$H NMR (d$_6$-DMSO; 300 MHz) δ 4.31-4.37 (m, 1H), 4.51-4.56 (m, 1H), 5.17-5.20 (m, 1H), 7.04-7.29 (m, 3H), 13.51 (s, 1H).

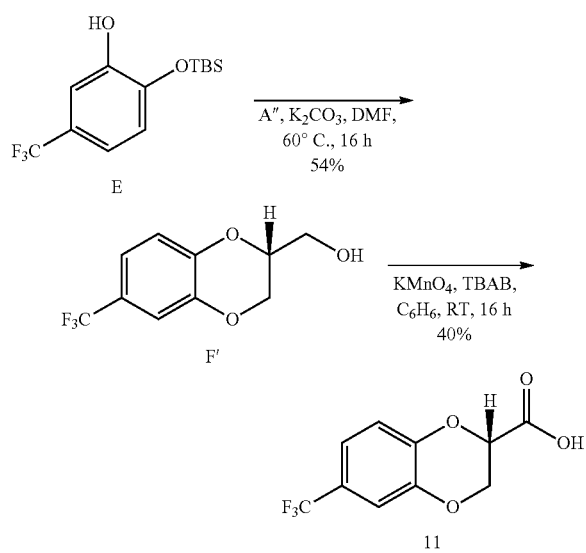

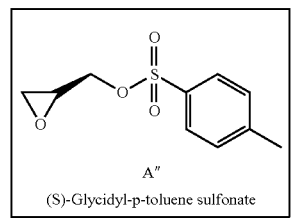

(R)-(6-(trifluoromethyl)-2,3-dihydrobenzo[b][1,4]dioxin-2-yl)methanol 11

The title compound was prepared from compound E and (S)-glycidyl-p-toluene sulfonate A" employing the procedure used for the preparation of compound F (above). NMR (CDCl$_3$; 300 MHz) δ 1.91 (t, 2H; J=6 MHz), 3.83-3.98 (m, 2H), 4.10-4.18 (m, 1H), 4.20-4.39 (m, 2H), 6.95-6.99 (m, H), 7.12-7.18 (m, 2H).

(S)-6-(trifluoromethyl)-2,3-dihydrobenzo[b][1,4]dioxine-2-carboxylic acid 11

The title compound was prepared from compound F' employing the procedure used for the preparation of compound 10 above. $^1$H NMR (d$_6$-DMSO; 300 MHz) δ 4.31-4.37 (m, 1H), 4.51-4.56 (m, 1H), 5.17-5.20 (m, 1H), 7.04-7.29 (m, 3H), 13.51 (s, 1H).

General Method for Preparation of Amides of the Invention

The amides of the invention can be prepared using the following synthetic method.

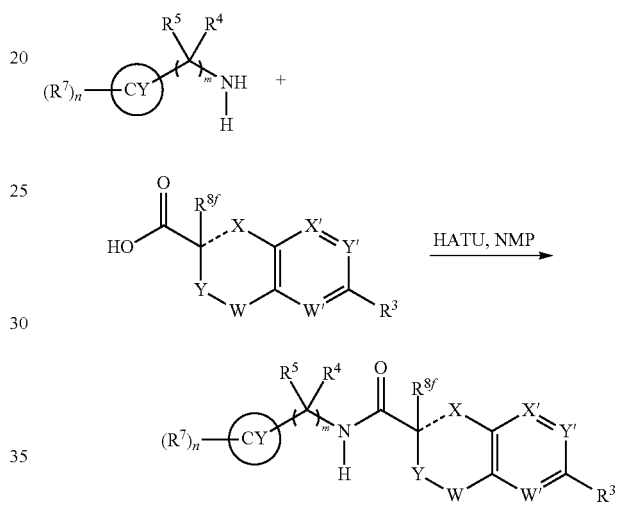

wherein n, CY, W, X, Y, W', X', Y', R$^3$, R$^4$, R$^5$, R$^7$, and R$^{8f}$ are as described herein and the dotted bond is a single or a double bond.

A suitable vial or round-bottom flask is charged sequentially with a solution of the amine, amine hydrochloride or amine dihydrochloride (0.15 mmol) in NMP (0.2 mL), a solution of the acid (0.13 mmol) and N,N-diisopropylethylamine (0.53 mmol) in NMP (0.1 mL). A solution of N,N,N',N'-tetramethyl-O-(7-azabenzotriazol-1-yl)uronium hexafluorophosphate (HATU, 0.16 mmol) in NMP (0.3 mL) is added. The resulting mixture is stirred at room temperature for 30 min to 15 h. The mixture is then filtered and purified by chromatography to afford the amide as a solid.

In one embodiment, NMP is replaced with DMF. In another embodiment, NMP is replaced with CH$_2$Cl$_2$. In yet another embodiment, NMP is replaced with THF.

In one embodiment, the reaction mixture is stirred for 30 min. In another embodiment, the reaction mixture is stirred for 15 h.

In one embodiment, the reaction mixture is carried out at room temperature. In another embodiment, the reaction is carried out at 50° C.

In one embodiment, the reaction mixture is purified using flash chromatography. In another embodiment, the reaction mixture is purified using HPLC. In yet another embodiment, the reaction mixture is purified using reverse phase HPLC.

Compound 1

Preparation of 6-tert-butyl-N-(quinolin-4-ylmethyl)-2,3-dihydrobenzo[b][1,4]dioxine-2-carboxamide

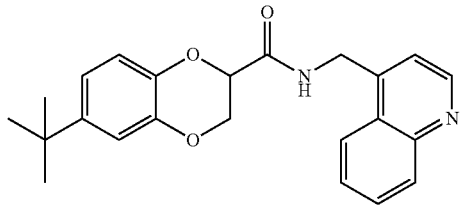

To a solution of 6-tert-Butyl-2,3-dihydro-benzo[1,4]dioxine-2-carboxylic acid (27 mg, 0.11 mmol), quinolin-4-yl-methanamine (15 mg, 0.09 mmol), and N,N,N',N'-tetramethyl-O-(7-azabenzotriazol-1-yl)uronium hexafluorophosphate (43 mg, 0.11 mmol) in DMF (0.4 mL) was added N,N-diisopropylethylamine (82 µL, 0.47 mmol). Tetrahydrofuran (0.8 mL) was added to dilute the solution. The reaction was left to stir overnight then concentrated and attempted purification by HPLC using 20-80% acetonitrile/water. Product isolated was less than 95% pure. It was purified again using 30-60% acetonitrile/water to obtain the product (23 mg, 64%) as a solid. m/z=376.8 (M+1)$^+$. $^1$H-NMR (400 MHz, DMSO-$d_6$) δ 8.89-8.81 (m, 1H), 8.76-8.72 (m, 1H), 8.16-8.13 (m, 1H), 8.04-8.02 (m, 1H), 7.80-7.75 (m, 1H), 7.66-7.61 (m, 1H), 7.11 (t, 1H, J=4.63 Hz), 6.93-6.89 (m, 2H), 4.99-4.95 (m, 1H), 4.93-4.73 (m, 2H), 4.41-4.28 (m, 2H), 1.24 (d, 9H, J=1.94 Hz).

Compound 2

6-Chloro-2H-chromene-3-carboxylic acid (Quinolin-4-ylmethyl)-amide

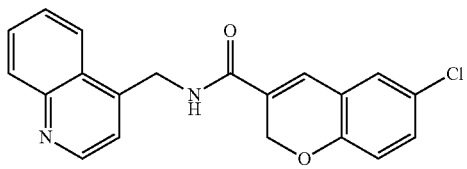

To a vial containing 6-chloro-2H-chromene-3-carboxylic acid (43.74 mg, 0.21 mmol) was added a solution containing N,N,N',N'-tetramethyl-O-(7-azabenzotriazol-1-yl)uronium hexafluorophosphate (79 mg, 0.21 mmol), DIPEA (2.4 eq), and 4-dimethylaminopyridine (2.1 mg, 0.017 mmol) in anhydrous DMF (3 mL). After stirring for 5 minutes, a solution of quinolin-4-yl-methylamine dihydrochloride (40 mg, 0.2 mmol) and DIPEA (2.4 eq) in anhydrous DMF (2 mL) was added. The reaction was stirred overnight at room temperature. The reaction mixture was poured into saturated NaHCO3 solution (50 mL) and extracted with EtOAc (3×50 mL). The combined organics were washed with brine (3×50 mL), dried (MgSO$_4$), filtered and concentrated. Flash chromatography (0 to 4% MeOH in DCM over 30 minutes) gave the product (26.4 mg) as a solid. m/z=350.8 (M+1), r.t.=2.26 mins. $^1$H NMR (400 MHz; DMSO-$d_6$) δ 8.99 (1H, t), 8.86 (1H, d), 8.20 (1H, dd), 8.06 (1H, dd), 7.79 (1H, t), 7.67 (1H, t), 7.42 (1H, d), 7.34 (2H, d), 7.27 (1H, dd), 6.90 (1H, d), 5.00 (2H, s), 4.90 (2H, d).

Compound 4

6-Trifluoromethoxy-2H-chromene-3-carboxylic acid (quinolin-4-ylmethyl)-amide

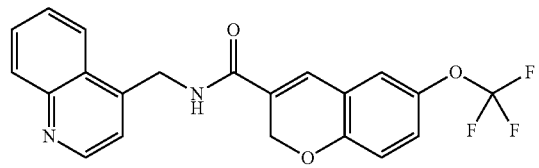

To a vial containing 6-trifluoromethoxy-2H-chromene-3-carboxylic acid (42 mg, 0.16 mmol) was added a solution containing N,N,N',N'-tetramethyl-O-(7-azabenzotriazol-1-yl)uronium hexafluorophosphate (67.5 mg, 0.18 mmol), DIPEA (2.4 eq), and 4-dimethylaminopyridine (1.97 mg, 0.016 mmol) in anhydrous MeCN (3 mL). After stirring for 5 minutes, a solution of quinolin-4-yl-methylamine dihydrochloride (41 mg, 0.18 mmol) and DIPEA (2.4 eq) in anhydrous MeCN (2 mL) was added. The reaction was stirred overnight at room temperature. The reaction mixture was poured into saturated NaHCO3 solution (50 mL) and extracted with EtOAc (3×50 mL). The combined organics were washed with brine (3×50 mL), dried (MgSO4), filtered and concentrated. Flash chromatography (0 to 3% MeOH in DCM over 40 minutes) gave the product (6.3 mg) as a solid. m/z=401.4 (M+1), r.t.=2.76 mins. $^1$H NMR (400 MHz; DMSO-$d_6$) δ 9.00 (1H, t), 8.86 (1H, d), 8.21 (1H, d), 8.06 (1H, d), 7.79 (1H, t), 7.67 (1H, t), 7.43 (1H, d), 7.37 (1H, s), 7.32 (1H, s), 7.25 (1H, d), 6.97 (1H, d), 5.03 (2H, s), 4.90 (2H, d).

Compound 5

6-Chloro-2H-chromene-3-carboxylic acid [1-(1H-indazol-5-yl)-ethyl]-amide

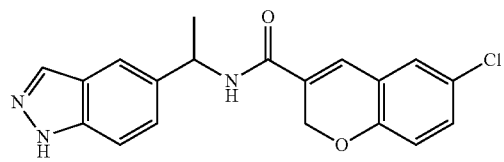

Step 1: Oxalyl chloride (69 µL, 0.8 mmol) was added in one portion to a stirred suspension of 6-chloro-2H-chromene-3-carboxylic acid (90.1 mg, 0.4 mmol) in DCM (5 mL) containing 2-3 drops of DMF at 0° C. under nitrogen. After stirring for 15 mins at 0° C. the mixture was allowed to warm to room temperature and stirred for 90 mins. TLC indicate a slight amount of acid left (used MeOH quench on TLC scale), so further oxalyl chloride (35 µL) was added at room temperature and the mixture was stirred for a further 90 mins. TLC indicated complete acid chloride formation so the mixture was concentrated under vacuum to leave a crude solid. The solid was dissolved in tetrahydrofuran (5 mL) and cooled to 0° C. under nitrogen. Triethylamine (114 µL, 0.8 mmol) was added followed by a solution of 1-(1-(tetrahydro-2H- pyran-2-yl)-1H-indazol-5-yl)ethanamine (100 mg, 0.4 mmol) in THF (2 mL). The mixture was stirred at 0° C. for 30 min then allowed to warm to room temperature and stirred overnight. The mixture was then concentrated under vacuum and the residue partitioned between EtOAc (30 mL) and H₂O (30 mL). The organic layer was washed with sat'd NaHCO₃ (1×20 mL) and brine (1×20 mL), then dried (MgSO₄), filtered and the solvent removed under vacuum to leave a solid. The solid was used directly in the next step without further purification. Yield assumed quantitative=178 mg.

Step 2: Concentrated hydrochloric acid (1 mL) was added to a stirred solution of 6-chloro-N-(1-(1-(tetrahydro-2H-pyran-2-yl)-1H-indazol-5-yl)ethyl)-2H-chromene-3-carboxamide (178 mg, 0.4 mmol) in methanol (5 mL, 0.1 mol) at room temperature. The mixture was heated to 50° C. and stirred for 1 hour. TLC indicated complete reaction, so after allowing to cool, the mixture was concentrated under vacuum and the residue partitioned between sat'd NaHCO₃ (30 mL—care: initial evolution of gas as reaction with excess acid ensues) and EtOAc (50 mL). The organic layer was washed with brine (1×20 mL), dried (MgSO₄), filtered and the solvent removed under vacuum to leave a crude solid. The solid was triturated with EtOAc (10 mL) and filtered. The filter cake was washed with EtOAc (2×3 mL) to give the product (35 mg). m/z=354.3 (M+1)⁺. ¹H NMR (400 MHz; DMSO-d₆) δ 13.00 (s, 1H), 8.64 (d, J=8.0 Hz, 1H), 8.04 (s, 1H), 7.70 (s, 1H), 7.48 (d, J=8.0 Hz, 1H), 7.39 (m, 1H), 7.32-7.24 (m, 3H), 6.86 (d, J=8.4 Hz, 1H), 5.21-5.13 (m, 1H), 4.97-4.88 (m, 2H), 1.48 (d, J=7.0 Hz, 3H).

Compounds 6 and 7

Preparation of (2S)—N-(1-(1H-indazol-5-yl)ethyl)-6-tert-butyl-2,3-dihydrobenzo[b][1,4]dioxine-2-carboxamide and (2R)—N-(1-(1H-indazol-5-yl)ethyl)-6-tert-butyl-2,3-dihydrobenzo[b][1,4]dioxine-2-carboxamide

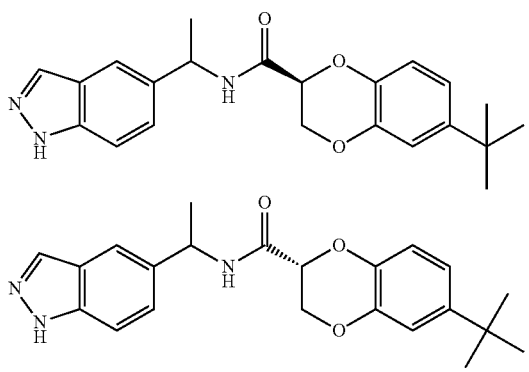

In a 20 ml vial, 1-(1-(tetrahydro-2H-pyran-2-yl)-1H-indazol-5-yl)ethanamine (80 mg, 0.3 mmol), 6-tert-butyl-2,3-dihydro-benzo[1,4]dioxine-2-carboxylic acid (120 mg, 0.49 mmol) and N,N,N',N'-tetramethyl-O-(7-azabenzotriazol-1-yl)uronium hexafluorophosphate (310 mg, 0.82 mmol) were dissolved in DCM (6 mL). N,N-Diisopropylethylamine (300 μL, 2.0 mmol) was added while stirring. The reaction was heated for 1 hour at 50° C. Saturated NaHCO₃ solution (20 mL) was poured into the vial and extracted with EtOAc (3×30 mL). The combined organics was washed once with brine (40 mL), dried over NaSO₄, filtered and concentrated to produce a brown oil. The oil was dissolved in Methanol (8 mL) and HCl (0.8 mL, 3.0 mol) was added. The reaction was heated at 50° C. for 1 hour. The solvent was removed under reduced pressure and the residue was purified by HPLC. Two diastereomers (26 mg, 20%; 48 mg, 40%) were isolated. m/z=379.7 and 380.2 (M+1)⁺. ¹H-NMR (400 MHz, DMSO-d₆) δ 12.96 (s, 1H), 8.51-8.48 (m, 1H), 7.95 (t, 1H, J=1.13 Hz), 7.51 (d, 1H, J=21.80 Hz), 7.42-7.39 (m, 1H), 7.24-7.19 (m, 1H), 7.01 (d, 1H, J=2.31 Hz), 6.90 (t, 1H, J=2.22 Hz), 6.86 (dd, 1H, J=17.78 Hz), 6.77 (d, 1H, J=8.49 Hz), 5.13-5.06 (m, 1H), 4.80-4.78 (m, 1H), 4.34-4.29 (m, 1H), 4.24-4.13 (m, 1H), 1.46 (dd, 3H, J=7.01 Hz), 1.23 (d, 9H, J=3.84 Hz). ¹H-NMR (400 MHz, DMSO-d₆) δ 13.00 (s, 1H), 8.55 (d, 1H, J=8.37 Hz), 8.04 (d, 1H, J=1.06 Hz), 7.69 (d, 1H, J=3.15 Hz), 7.50 (d, 1H, J=8.82 Hz), 7.38-7.35 (m, 1H), 6.98 (d, 1H, J=2.26 Hz), 6.91-6.84 (m, 2H), 6.78 (d, 1H, J=8.52 Hz), 5.13-5.04 (m, 1H), 4.74-4.71 (m, 1H), 4.36 (dt, 1H, J=10.88 Hz), 4.18-4.07 (m, 1H), 1.45-1.42 (m, 3H), 1.22 (d, 9H, J=6.67 Hz).

Compound 8

7-tert-Butyl-2,3-dihydro-benzo[1,4]dioxine-2-carboxylic acid (2-hydroxymethyl-thiazolo[5,4-b]pyridin-6-yl)-amide

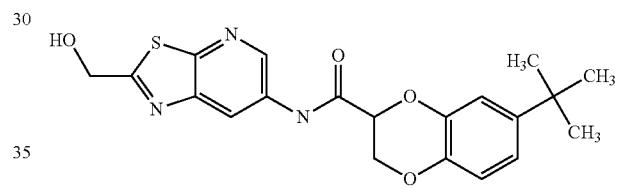

The compound is prepared using the method outlined for Compound 15 and starting from 7-tert-butyl-2,3-dihydro-benzo[1,4]dioxin-2-carboxylic acid. m/z=400.5 (M+1)⁺. HPLC: 9.916 min. ¹H NMR (400 MHz; d₆-DMSO) δ 10.58 (s, 1H), 8.80 (d, 1H, J=2.3 Hz), 8.62 (d, 1H, J=2.3 Hz), 6.98 (d, 1H, J=8.3 Hz), 6.93 (dd, 1H, J=8.3, 2.3 Hz), 6.88 (d, 1H, J=8.5 Hz), 6.37 (t, 1H, J=8.1 Hz), 5.05 (dd, 1H, J=5.8, 2.6 Hz), 4.86 (d, 2H J=5.8 Hz), 4.46 (dd, 1H, J=11.6, 2.6 Hz), 4.40 (dd, 1H, J=11.6, 5.8 Hz), 1.23 (s, 9H).

Compound 9

4-Methyl-6-trifluoromethyl-3,4-dihydro-2H-benzo[1,4]oxazine-2-carboxylic acid [1-(1H-indazol-5-yl)ethyl]amide

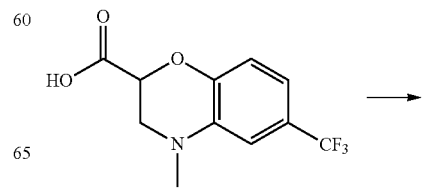

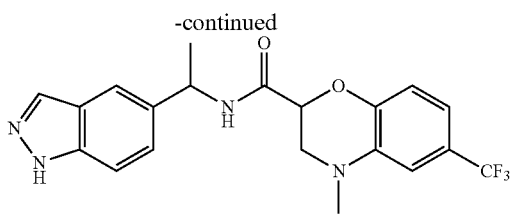

A stirred solution of 4-methyl-6-trifluoromethyl-3,4-dihydro-2H-benzo[1,4]oxazine-2-carboxylic acid (50 mg, 0.2 mmol), HBTU (73 mg, 0.2 mmol) and DIPEA (67 µL, 1.5 mmol) in anhydrous DMF (2 mL) was added to a solution of 1-(1-(tetrahydro-2H-pyran-2-yl)-1H-indazol-5-yl)ethanamine (43 mg, 0.17 mmol) in anhydrous DMF (0.5 mL). The reaction was stirred overnight at room temperature, then poured into saturated NaHCO$_3$ solution (30 mL) and extracted with EtOAc (3×30 mL). The combined organics were washed with brine (3×30 mL), dried (MgSO$_4$), filtered and concentrated. The resulting product was redissolved in MeOH (10 mL), and 2N HCl (1 mL) was added. After stirring overnight at 50° C., the methanol was removed by evaporation, and the aqueous residue poured into saturated NaHCO$_3$ solution (30 mL) and extracted with EtOAc (3×30 mL). The combined organics were washed with brine (3×30 mL), dried (MgSO$_4$), filtered and concentrated. Flash chromatography (0 to 3.5% MeOH in DCM) gave the title compound (22 mg, 31%) as a solid, containing a mixture of diastereomers. m/z=405.5 (M+1), r.t.=3.36, 3.42 mins. $^1$H NMR (400 MHz; d$_6$-DMSO) δ 13.00 (1H, s), 12.98 (1H, s), 8.51 (1H, d), 8.44 (1H, d), 8.04 (1H, s), 7.95 (1H, s), 7.68 (1H, s), 7.54-7.51 (2H, m), 7.42 (1H, d), 7.36 (1H, d), 7.25 (1H, d), 7.03-6.89 (6H, m), 5.12-5.04 (2H, m), 4.87-4.81 (2H, m), 3.48-3.43 (2H, m), 3.34-3.30 (2H, m), 2.88 (6H, d), 1.47-1.43 (6H, m).

Compound 11

N—((R)-1-(1H-indazol-5-yl)ethyl)-2-(1,1,1-trifluoro-2-methylpropan-2-yl)-5,6,7,8-tetrahydroquinoline-6-carboxamide

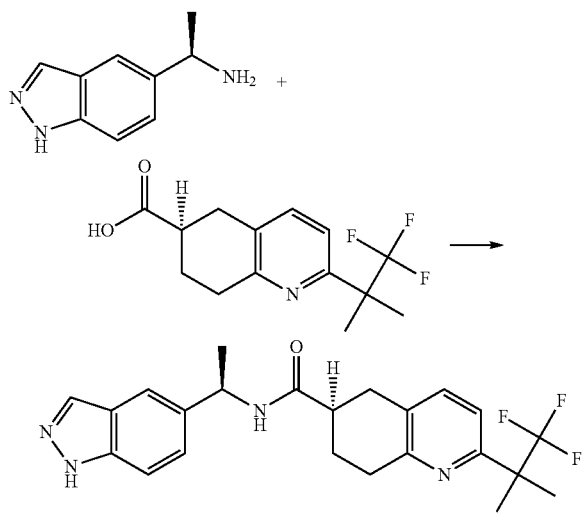

A 2 mL vial was charged sequentially with a solution of (R)-1-(1H-indazol-5-yl)ethanamine dihydrochloride (34 mg, 0.15 mmol) in NMP (0.2 mL, 2 mmol), a solution of (R)-2-(1,1,1-trifluoro-2-methylpropan-2-yl)-5,6,7,8-tetrahydroquinoline-6-carboxylic acid (38 mg, 0.13 mmol) and N,N-diisopropylethylamine (93 µL, 0.53 mmol) in NMP (0.1 mL). A solution of N,N,N',N'-tetramethyl-O-(7-azabenzotriazol-1-yl)uronium hexafluorophosphate (61 mg, 0.16 mmol) in NMP (0.3 mL) was added to the resulting mixture and the solution stirred at room temperature. After 30 min the mixture was filtered and purified by reverse-phase HPLC (20-75% MeCN in 10 mM Et$_2$NH/H$_2$O) to afford the amide as a solid (44 mg, 76%). $^1$H NMR (400 MHz, DMSO-d$_6$) δ 12.98 (br s, 1H), 8.38 (d, J=8.1 Hz, 1H), 8.04 (d, J=0.4 Hz, 1H), 7.66 (s, 1H), 7.50 (t, J=8.1 Hz, 1H), 7.34 (d, J=8.1 Hz, 1H), 5.06 (app pentet, J=7.3 Hz, 1H), 2.94-2.76 (m, 4H), 2.68-2.57 (m, 1H), 2.11-2.03 (m, 1H), 1.90-1.78 (m, 1H), 1.54 (s, 6H), 1.43 (d, J=7.0 Hz, 3H); m/z=431.3 (M+1)$^+$.

Compound 12

N—((R)-1-(1H-indazol-5-yl)ethyl)-2-(1,1,1-trifluoro-2-methylpropan-2-yl)-5,6,7,8-tetrahydroquinoline-6-carboxamide

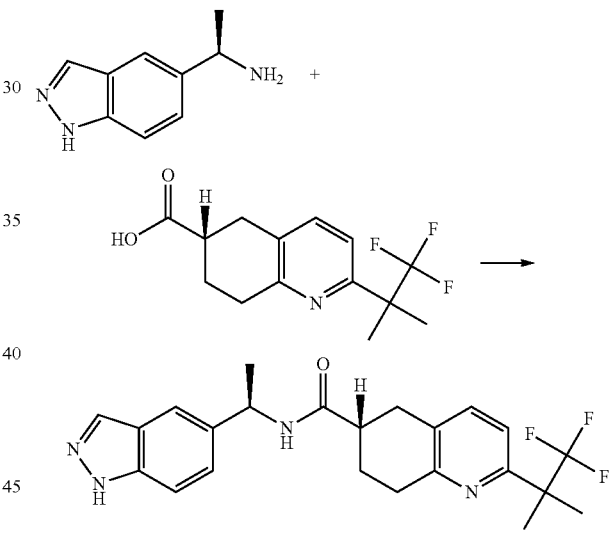

A 2 mL vial was charged sequentially with a solution of (R)-1-(1H-indazol-5-yl)ethanamine dihydrochloride (34 mg, 0.15 mmol) in NMP (0.2 mL), a solution of (S)-2-(1,1,1-trifluoro-2-methylpropan-2-yl)-5,6,7,8-tetrahydroquinoline-6-carboxylic acid (38 mg, 0.13 mmol) and N,N-diisopropylethylamine (93 µL, 0.53 mmol) in NMP (0.1 mL). A solution of N,N,N',N'-tetramethyl-O-(7-azabenzotriazol-1-yl)uronium hexafluorophosphate (61 mg, 0.16 mmol) in NMP (0.3 mL) was added to the resulting mixture and the solution stirred at room temperature. After 30 min the mixture was filtered and purified by reverse-phase HPLC (20-75% MeCN in 10 mM Et$_2$NH/H$_2$O) to afford the amide as a solid (41 mg, 71%). $^1$H NMR (400 MHz, DMSO-d$_6$) δ 12.99 (br s, 1H), 8.42 (d, J=8.0 Hz, 1H), 8.04 (s, 1H), 7.66 (s, 1H), 7.54 (d, J=8.1 Hz, 1H), 7.50 (d, J=8.6 Hz, 1H), 7.38-7.32 (m, 2H), 5.05 (app pentet, J=7.0 Hz, 1H), 2.96-2.78 (m, 4H), 2.68-2.60 (m, 1H), 2.05-1.97 (m, 1H), 1.82-1.69 (m, 1H), 1.53 (s, 6H), 1.42 (d, J=7.0 Hz, 3H); m/z=431.2 (M+1)$^+$.

Compound 13

(R)-6-Trifluoromethyl-2,3-dihydro-benzo[1,4]dioxine-2-carboxylic acid [1-(1H-indazol-5-yl)-ethyl]-amide

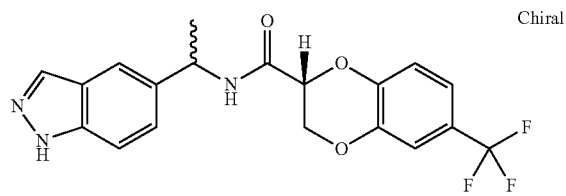

To a solution of 1-(1-(tetrahydro-2H-pyran-2-yl)-1H-indazol-5-yl)ethanamine (66 mg, 0.27 mmol), (R)-6-trifluoromethyl-2,3-dihydrobenzo[1,4]dioxine-2-carboxylic acid (60.6 mg, 0.25 mmol), 4-dimethylaminopyridine (2.5 mg, 0.02 mmol) and N,N-diisopropylethylamine (153 µL, 0.88 mmol) in anhydrous DMF (4 mL) was added N,N,N',N'-tetramethyl-O-(7-azabenzotriazol-1-yl)uronium hexafluorophosphate (102 mg, 0.27 mmol). The reaction was stirred at room temperature overnight. The reaction mixture was poured into saturated NaHCO$_3$ solution (30 mL) and extracted with EtOAc (3×30 mL). The combined organics were washed with brine (3×30 mL), dried (MgSO$_4$), filtered and concentrated. The residue was dissolved in Methanol (20 mL) and 2N HCl (5 mL) was added. The reaction mixture was heated at 60° C. for 2 hours, then cooled and the methanol removed under vacuum. The remaining aqueous product was poured into saturated NaHCO$_3$ solution (30 mL) and extracted with EtOAc (3×30 mL). The combined organics were washed with brine (3×30 mL), dried (MgSO$_4$), filtered and concentrated. Flash chromatography (0 to 3% MeOH in DCM over 30 minutes) gave the product (43 mg) as a solid. m/z=391.8 (M+1), r.t.=2.96 and 3.04 mins. $^1$H NMR (400 MHz; DMSO-d$_6$) δ 12.99 (1H, d), 8.68-8.60 (1H, m), 8.04 (0.5H, s), 7.94-7.87 (0.5H, m), 7.69 (0.5H, s), 7.53-7.16 (5H, m), 7.08-7.04 (0.5H, m), 5.12-4.90 (2H, m), 4.47-4.30 (2H, m), 1.46-1.41 (3H, m).

Compound 14

(S)-6-Trifluoromethyl-2,3-dihydro-benzo[1,4]dioxine-2-carboxylic acid [1-(1H-indazol-5-yl)-ethyl]-amide

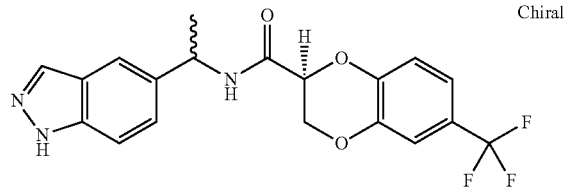

To a solution of 1-(1-(tetrahydro-2H-pyran-2-yl)-1H-indazol-5-yl)ethanamine (66 mg, 0.27 mmol), (S)-6-trifluoromethyl-2,3-dihydrobenzo[1,4]dioxine-2-carboxylic acid (60.6 mg, 0.25 mmol), 4-dimethylaminopyridine (2.5 mg, 0.02 mmol) and N,N-diisopropylethylamine (153 µL, 0.88 mmol) in anhydrous DMF (4 mL) was added N,N,N',N'-tetramethyl-O-(7-azabenzotriazol-1-yl)uronium hexafluorophosphate (102 mg, 0.27 mmol). The reaction was stirred at room temperature overnight. The reaction mixture was poured into saturated NaHCO$_3$ solution (30 mL) and extracted with EtOAc (3×30 mL). The combined organics were washed with brine (3×30 mL), dried (MgSO$_4$), filtered and concentrated. The residue was dissolved in methanol (20 mL) and 2N HCl (5 mL) was added. The reaction mixture was heated at 60° C. for 2 hours, then cooled and the methanol removed under vacuum. The remaining aqueous product was poured into saturated NaHCO$_3$ solution (30 mL) and extracted with EtOAc (3×30 mL). The combined organics were washed with brine (3×30 mL), dried (MgSO$_4$), filtered and concentrated. Flash chromatography (0 to 3% MeOH in DCM over 30 minutes) gave the product (23 mg) as a solid.

m/z=392.3 (M+1), r.t.=2.96 and 3.05 mins. $^1$H NMR (400 MHz; DMSO-d$_6$) δ 12.99 (1H, d), 8.68-8.60 (1H, m), 8.04 (0.5H, s), 7.93-7.91 (0.5H, m), 7.69 (0.5H, s), 7.51-7.17 (5H, m), 7.08-7.04 (0.5H, m), 5.12-4.91 (2H, m), 4.47-4.31 (2H, m), 1.46-1.41 (3H, m).

Compound 15

2-(2,2,2-Trifluoro-1,1-dimethyl-ethyl)-5,6,7,8-tetrahydro-quinoline-6-carboxylic acid (2-hydroxymethyl-thiazolo[5,4-b]pyridin-6-yl)-amide

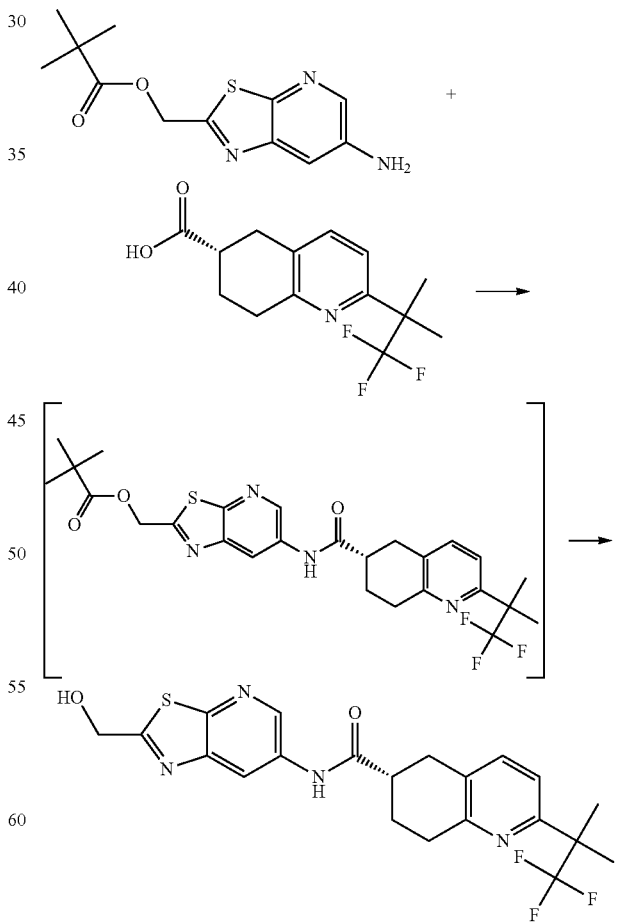

To a mixture of (6-aminothiazolo[5,4-b]pyridin-2-yl)methyl pivalate (60 mg, 0.20 mmol), (R)-2-(1,1,1-trifluoro-2- methylpropan-2-yl)-5,6,7,8-tetrahydroquinoline-6-carboxylic acid (45 mg, 0.16 mmol) and HATU (89 mg, 0.23 mmol) in N,N-dimethylformamide (3 mL), N,N-diisopropylethylamine (82 μL, 0.47 mmol) was added. After 6 h, the temperature was raised to 60° C., and the mixture was heated overnight. After 25 h, the reaction mixture was diluted with EtOAc (50 mL), washed with brine (4×20 mL), 2M Na$_2$CO$_3$ (20 mL), dried (MgSO$_4$), filtered and concentrated to a brown oil that was used without further purification in the next step.

Sodium (23 mg, 1.0 mmol) was added to methanol (1.0 mL) at room temperature. After complete dissolution of the sodium, the pivalate (assumed 0.16 mmol) dissolved in methanol (3 mL) was added. After 20 min, the mixture was partitioned between EtOAc (50 mL) and brine (50 mL). The aqueous layer was extracted with EtOAc (15 mL), and the combined organic layers were dried (Na$_2$SO$_4$), filtered, concentrated and the residue absorbed on silica. Chromatography on silica (20-100% EtOAc/hexanes as eluent) followed by further purification by reverse-phase HPLC (20-80% ACN in 10 mM Et$_2$NH/H$_2$O) afforded the amide (36 mg, 51%) as a solid. $^1$H NMR (400 MHz, DMSO-d$_6$) δ 10.53 (s, 1H), 8.75 (d, J=2.3 Hz, 1H), 8.66 (d, J=2.3 Hz, 1H), 7.59 (d, J=8.1 Hz, 1H), 7.40 (d, J=8.1 Hz, 1H), 6.37 (t, J=5.9 Hz, 1H), 4.86 (d, J=5.9 Hz, 2H), 3.07-2.84 (m, 5H), 2.27-2.17 (m, 1H), 2.02-1.88 (m, 1H), 1.56 (s, 6H); m/z=451.0 (M+1)$^+$.

Compound 16

Preparation of (R)-6-Trifluoromethyl-2,3-dihydrobenzo[1,4]dioxine-2-carboxylic acid (2-hydroxymethylthiazolo[4,5-b]pyridin-6-yl)amide

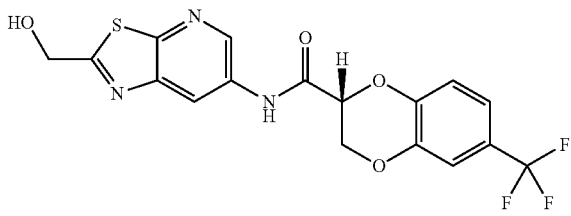

To a solution of 6-aminothiazolo[5,4-b]pyridine-2-yl)methyl pivalate (70 mg, 0.26 mmol), (R)-6-trifluoromethyl-2,3-dihydrobenzo[1,4]dioxine-2-carboxylic acid (60 mg, 0.2 mmol), 4-dimethylaminopyridine (2.4 mg, 0.02 mmol) and N,N-diisopropylethylamine (151 μL, 0.87 mmol) in anhydrous N,N-dimethylformamide (4 mL) was added HATU (101 mg, 0.26 mmol). The reaction was stirred overnight at room temperature, then poured into saturated NaHCO$_3$ solution (30 mL) and extracted with EtOAc (3×30 mL). The combined organics were washed with brine (3×30 mL), dried (MgSO$_4$), filtered and concentrated. The residue was dissolved in methanol (2 mL), and a solution of sodium (37 mg, 1.5 mmol) in methanol (4 mL) was added. After stirring for 10 minutes at room temperature, saturated NH$_4$Cl (4 mL) was added, and the methanol removed by evaporation. The reaction mixture was poured into water (50 mL) and extracted with EtOAc (3×30 mL). The combined organics were washed with brine (3×30 mL), dried (MgSO$_4$), filtered and concentrated. Flash chromatography (0 to 4% MeOH in DCM) gave the title compound (36 mg, 30%) as a solid. m/z=412.3 (M+1), r.t.=2.88 mins. $^1$H NMR (400 MHz; d$_6$-DMSO) δ10.65 (1H, s), 8.77 (1H, t), 8.60 (1H, d), 7.40-7.11 (3H, m), 6.38 (1H, t), 5.24-5.20 (1H, m), 4.86 (2H, d), 4.60-4.55 (2H, s).

Compound 17

(R)-6-Trifluoromethyl-2,3-dihydro-benzo[1,4]dioxine-2-carboxylic acid (7,8-dihydro-5H-pyrano[4,3-b]pyridin-3-yl)-amide

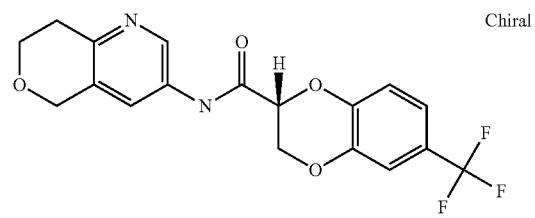

The compound is prepared in a similar manner as Compound 18 by condensing (R)-6-(trifluoromethyl)-2,3-dihydrobenzo[1,4]dioxine-2-carboxylic acid (38 mg, 0.15 mmol) with 7,8-dihydro-5H-pyrano[4,3-b]pyridin-3-ylamine (42 mg, 0.28 mmol) for 16 hours and purified by semi-preparative HPLC (55-75 gradient) to give the titled amide (52 mg, 89%). m/z=381.1 (M+1)$^+$. HPLC: 9.62 min. $^1$H NMR (400 MHz; d$_6$-DMSO) δ 10.38 (m, 1H), 8.52 (d, 1H, J=2.3 Hz), 7.77 (d, 1H, J=2.3 Hz), 7.36 (d, 1H, J=2.0 Hz), 7.26-7.22 (m, 2H), 7.09 (d, 1H, J=7.7 Hz), 5.17-5.14 (m, 1H), 4.52-4.49 (m, 2H), 3.95 (t, 2H, J=5.7 Hz), 2.82 (t, 2H, J=5.7 Hz).

Compound 18

2-(2,2,2-Trifluoro-1,1-dimethyl-ethyl)-5,6,7,8-tetrahydro-quinoline-6-carboxylic acid (7,8-dihydro-5H-pyrano[4,3-b]pyridin-3-yl)-amide

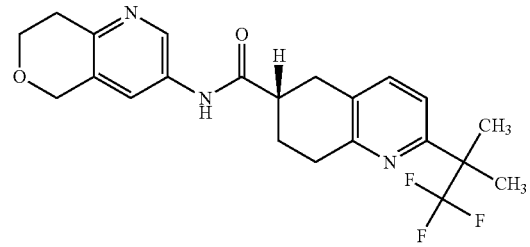

To a mixture of 7,8-Dihydro-5H-pyrano[4,3-b]pyridin-3-ylamine (36 mg, 0.24 mmol) [Takada, Susumu; Sasatani, Takashi; Chomei, Nobuo; Adachi, Makoto; Fujishita, Toshio; Eigyo, Masami; Murata, Shunji; Kawasaki, Kazuo; Matsushita, Akira. *Journal of Medicinal Chemistry* 1996, 39, 2844-2851], (R)-2-(1,1,1-trifluoro-2-methylpropan-2-yl)-5,6,7,8-tetrahydroquinoline-6-carboxylic acid (38 mg, 0.13 mmol) and N,N,N',N'-tetramethyl-O-(7-azabenzotriazol-1-yl)uronium hexafluorophosphate (136 mg, 0.36 mmol) in N,N-dimethylformamide (2 mL), N,N-diisopropylethylamine (0.1 mL, 0.6 mmol) was added and the reaction was heated at 60° C. overnight. LCMS shows mainly SM.

More 7,8-dihydro-5H-pyrano[4,3-b]pyridin-3-ylamine (12 mg, 0.08 mmol), more N,N,N',N'-tetramethyl-O-(7-azabenzotriazol-1-yl)uronium hexafluorophosphate (54 mg, 0.14 mmol) and more N,N-diisopropylethylamine (50 pt, 0.3 mmol) were added and the reaction was stirred at 60° C. 16 h. The crude was purified by semi-preparative HPLC (55-75 gradient) to yield the amide (30 mg, 50%) as a solid.

m/z=420.1 (M+HPLC: 10.29 min. $^1$H NMR (400 MHz; d$_6$-DMSO) δ 10.21 (s, 1H), 8.51 (d, 1H, J=2.5 Hz), 7.82 (d, 1H, J=2.3 Hz), 7.56 (d, 1H, J=8.1 Hz), 7.37 (d, 1H, J=8.1 Hz), 4.68 (s, 2H), 3.95 (t, 2H, J=5.9 Hz), 2.97-2.80 (m, 7H), 2.19-2.14 (m, 1H), 1.95-1.85 (m, 1H).

Compound 19

2-(2,2,2-Trifluoro-1,1-dimethyl-ethyl)-5,6,7,8-tetrahydro-Quinoline-6-carboxylic acid (7,8-dihydro-5H-pyrano[4,3-b]pyridin-3-yl)-amide

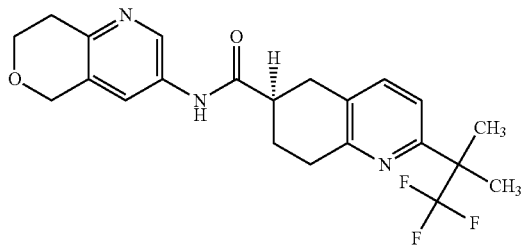

To a mixture of 7,8-dihydro-5H-pyrano[4,3-b]pyridin-3-ylamine (36 mg, 0.24 mmol), (S)-2-(1,1,1-trifluoro-2-methylpropan-2-yl)-5,6,7,8-tetrahydroquinoline-6-carboxylic acid (38 mg, 0.13 mmol) and N,N,N',N'-tetramethyl-O-(7-azabenzotriazol-1-yl)uronium hexafluorophosphate (136 mg, 0.36 mmol) in DMF (1 mL), N,N-diisopropylethylamine (0.1 mL, 0.6 mmol) was added and the reaction was heated at 60° C. for 16 hours. The crude was purified by semi-preparative HPLC (55-75 gradient) to give the titled amide (41 mg, 74%). m/z=420.2 (M+1)$^+$. HPLC: 10.31 min. NMR (400 MHz; d$_6$-DMSO) δ 10.21 (s, 1H), 8.51 (d, 1H, J=2.5 Hz), 7.82 (d, 1H, J=2.3 Hz), 7.56 (d, 1H, J=8.1 Hz), 7.37 (d, 1H, J=8.1 Hz), 4.68 (s, 2H), 3.95 (t, 2H, J=5.9 Hz), 2.97-2.80 (m, 7H), 2.19-2.14 (m, 1H), 1.95-1.85 (m, 1H).

Compound 20

(R)—N—((R)-1-(6,7-dihydro-5H-pyrazolo[1,1-b][1,3]oxazin-3-yl)ethyl)-6-methyl-2-(1,1,1-trifluoro-2-methylpropan-2-yl)-5,6,7,8-tetrahydroquinoline-6-carboxamide

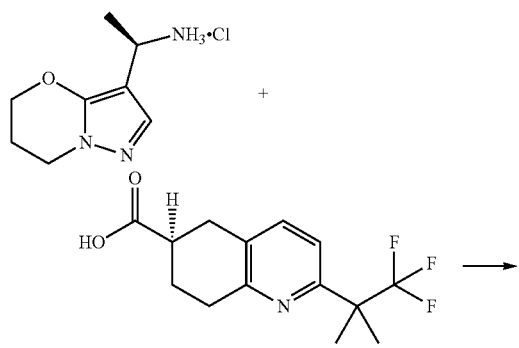

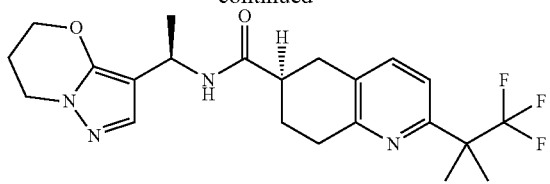

A 2 mL vial was charged with (R)-1-(6,7-dihydro-5H-pyrazolo[5,1-b][1,3]oxazin-3-yl)ethanamine dihydrochloride (35 mg, 0.15 mmol), (R)-2-(1,1,1-trifluoro-2-methylpropan-2-yl)-5,6,7,8-tetrahydroquinoline-6-carboxylic acid (38 mg, 0.13 mmol), N,N-diisopropylethylamine (93 μL, 0.53 mmol) and N-methylpyrrolidinone (0.2 mL). A solution of N,N,N',N'-tetramethyl-O-(7-azabenzotriazol-1-yl)uronium hexafluorophosphate (61 mg, 0.16 mmol) in N-methylpyrrolidinone (0.3 mL) was added and the solution stirred at room temperature. After 30 min the mixture was filtered and purified by reverse-phase HPLC (20-75% MeCN in 10 mM Et$_2$NH/H$_2$O; then 20-75% MeCN in 0.1% HCO$_2$H/H$_2$O) afforded the amide, after neutralization with MP-carbonate resin, as a glass (29.5 mg, 51%). $^1$H NMR (400 MHz, DMSO-d$_6$) δ 8.02 (d, J=7.9 Hz, 21H), 7.53 (d, J=8.1 Hz, 1H), 7.35 (d, J=8.1 Hz, 1H), 7.21 (s, 1H), 4.78 (app pentet, J=7.0 Hz, 1H), 4.27 (t, J=5.2 Hz, 2H), 4.04 (t, J=6.2 Hz, 2H), 2.91-2.74 (m, 4H), 2.59-2.50 (m, 1H), 2.15 (app pentet, J=5.7 Hz, 2H), 2.05-1.95 (m, 1H), 1.86-1.74 (m, 1H), 1.54 (s, 6H), 1.29 (d, J=6.9 Hz, 3H); m/z=437.1 (M+1)$^+$.

Compound 21

(R)-2-(2,2,2-Trifluoro-1,1-dimethyl-ethyl)-5,6,7,8-tetrahydro-quinoline-6-carboxylic acid quinolin-3-ylamide

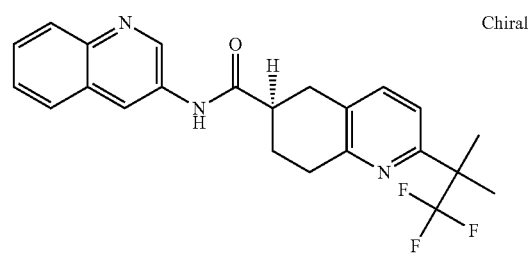

To a mixture of 3-quinolinamine (26 mg, 0.18 mmol), (R)-2-(1,1,1-trifluoro-2-methylpropan-2-yl)-5,6,7,8-tetrahydroquinoline-6-carboxylic acid (40 mg, 0.14) and N,N,N',N'-tetramethyl-O-(7-azabenzotriazol-1-yl)uronium hexafluorophosphate (79 mg, 0.21 mmol) in N-methylpyrrolidinone (0.7 mL), followed by N,N-diisopropylethylamine (73 μL, 0.42 mmol) was added. Aliquot after 2 min: LCMS showed formation of the HOAt and Me ester, and some amide. After 1.3 h, the reaction was heated at 60° C. Aliquot after 25 h: LCMS showed the reaction was complete—all HOAt ester had been consumed. The material was filtered and purified by reverse-phase HPLC (20-80% ACN in 10 mM Et$_2$NH/H$_2$O; 3 injections of 400 μL, each) to afford the amide (43 mg, 75%) as a solid. $^1$H NMR (400 MHz, DMSO-d$_6$) δ 10.56 (s, 1H), 8.95 (d, J=2.4 Hz, 1H), 8.76 (d, J=2.4 Hz, 1H), 7.96 (d, J=8.4 Hz, 1H), 7.92 (dd, J=1.1, 8.0 Hz, 1H), 7.68-7.54

(m, 3H), 7.40 (d, J=8.0 Hz, 1H), 3.08-3.00 (m, 2H), 2.99-2.87 (m, 3H), 2.29-2.20 (m, 1H), 2.03-1.91 (m, 1H), 1.56 (s, 6H); m/z=414.1 (M+1)+.

Compound 22

(S)—N—((R)-1-(6,7-dihydro-5H-pyrazolo[5,1-b][1,3]oxazin-3-yl)ethyl)-2-(1,1,1-trifluoro-2-methylpropan-2-yl)-5,6,7,8-tetrahydroquinoline-6-carboxamide

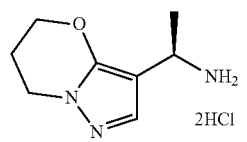

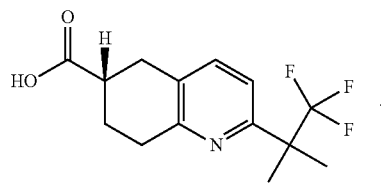

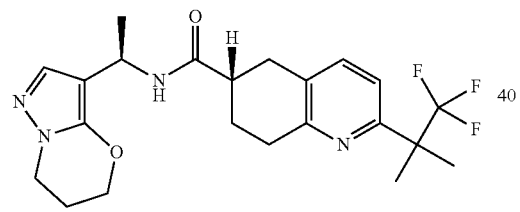

A 2 mL vial was charged with (R)-1-(6,7-dihydro-5H-pyrazolo[5,1-b][1,3]oxazin-3-yl)ethanamine dihydrochloride (35 mg, 0.15 mmol), (S)-2-(1,1,1-trifluoro-2-methylpropan-2-yl)-5,6,7,8-tetrahydroquinoline-6-carboxylic acid (38 mg, 0.13 mmol), N-methylpyrrolidinone (200 μL) and N,N-diisopropylethylamine (93 μL, 0.53 mmol). A solution of N,N,N',N'-tetramethyl-O-(7-azabenzotriazol-1-yl)uronium hexafluorophosphate (61 mg, 0.16 mmol) in N-methylpyrrolidinone (300 μL) was added and the resulting mixture was stirred at room temperature for 2 hours. The mixture was filtered and purified by reverse-phase HPLC (20-75% MeCN in 10 mM Et$_2$NH/H$_2$O) to afford the product as a foam (31.0 mg, 53%). $^1$H NMR (400 MHz, DMSO-d$_6$) δ 8.04 (d, J=7.9 Hz, 1H), 7.53 (d, J=8.1 Hz, 1H), 7.35 (d, J=8.1 Hz, 1H), 7.20 (s, 1H), 4.78 (app pentet, J=7.3 Hz, 1H), 4.27 (app t, J=5.2 Hz, 2H), 4.04 (t, J=6.2 Hz, 2H), 2.93-2.73 (m, 4H), 2.61-2.52 (m, 1H), 2.19-2.10 (m, 2H), 2.03-1.94 (m, 1H), 1.85-1.72 (m, 1H), 1.54 (s, 6H), 1.29 (d, J=6.9 Hz, 3H); m/z=437.4 (M+1)+.

Compound 23

2-(2,2,2-Trifluoro-1,1-dimethyl-ethyl)-5,6,7,8-tetrahydro-quinoline-6-carboxylic acid (1-acetyl-2,3-dihydro-1H-indol-6-yl)-amide

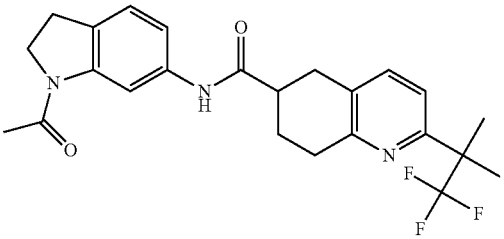

To a mixture of 1-acetyl-6-amino-indoline (32 mg, 0.18 mmol), (R)-2-(1,1,1-trifluoro-2-methylpropan-2-yl)-5,6,7,8-tetrahydroquinoline-6-carboxylic acid (40 mg, 0.14 mmol) was added HATU (79 mg, 0.21 mmol) in NMP (0.7 mL), followed by N,N-diisopropylethylamine (73 μL, 0.42 mmol). After 1.3 h, the reaction was heated to 60° C. After 25 h, the material was filtered and purified by reverse-phase HPLC (40-75% ACN in 0.1% HCO$_2$H/H$_2$O). The fractions were stirred with MP-carbonate resin (1.0 g, 3.0 mmol/g) overnight, filtered and concentrated to afford the amide (40 mg, 64%) as a solid foam. $^1$H NMR (400 MHz, DMSO-d$_6$) δ 10.03 (s, 1H), 8.21 (d, J=1.8 Hz, 1H), 7.57 (d, J=8.1 Hz, 1H), 7.51 (d, J=8.1 Hz, 1H), 7.38 (dd, J=1.8, 8.1 Hz, 1H), 7.13 (d, J=8.1 Hz, 1H), 4.09 (t, J=8.5 Hz, 2H), 3.08 (t, J=8.5 Hz, 2H), 3.02-2.85 (m, 4H), 2.85-2.74 (m, 1H), 2.18-2.12 (m, 1H), 2.16 (s, 3H), 1.93-1.82 (m, 1H), 1.55 (s, 6H); m/z=446.5 (M+1)+.

Compound 24

6-Methyl-2-(2,2,2-trifluoro-1,1-dimethyl-ethyl)-5,6,7,8-tetrahydro-quinoline-6-carboxylic acid (2-hydroxymethyl-thiazolo[5,4-b]pyridin-6-yl)-amide

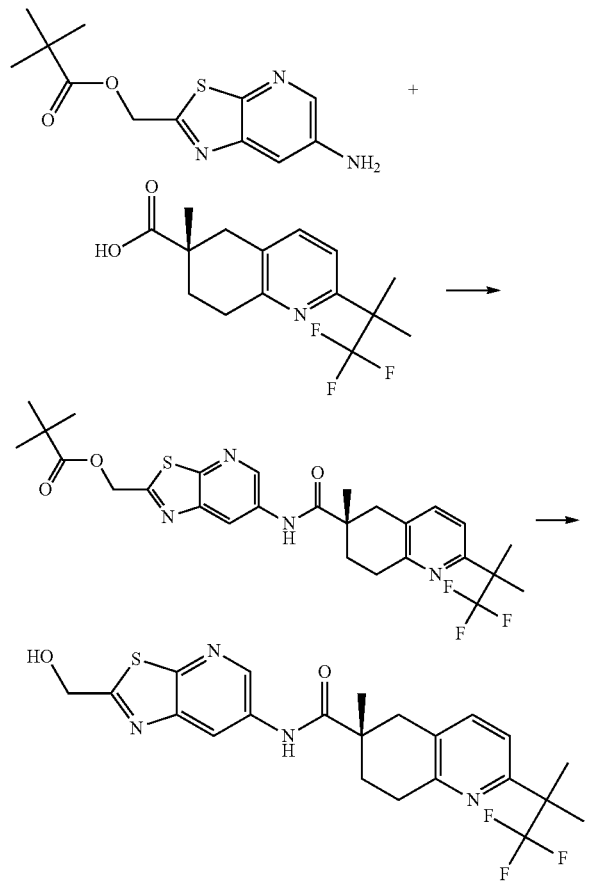

A solution of oxalyl chloride (5.6 μL, 0.066 mmol), and DMF (1 μL) in DCM (3 mL) was added to (S)-6-methyl-2-(1,1,1-trifluoro-2-methylpropan-2-yl)-5,6,7,8-tetrahydro-quinoline-6-carboxylic acid (4 mg, 0.01 mmol), and the mixture stirred at room temperature. After 2.7 h, the mixture was concentrated to dryness, and the residue re-dissolved in DCM (2 mL). A solution of (6-aminothiazolo[5,4-b]pyridin-2-yl) methyl pivalate (7.0 mg, 0.026 mmol), N,N-diisopropylethylamine (12 μL, 0.066 mmol) and 4-dimethylaminopyridine (0.1 mg, 0.8 μmol) in DCM (0.1 mL) was added, and the mixture stirred at room temperature. After 2.5 h, the reaction was quenched with methanol (0.1 mL), concentrated in vacuo, and used directly in the next step.

A solution of the crude pivalate in methanol (0.5 mL) was treated with 4.4 M of sodium methoxide in methanol (50 μL, 0.22 mmol), and the mixture aged at room temperature. After 15 min, the mixture was partitioned between EtOAc (10 mL) and sat NaHCO$_3$ (5 mL). The organic layer was dried (Na$_2$SO$_4$), filtered, concentrated and purified by reverse-phase HPLC (40-75% ACN in 10 mM Et$_2$NH/H$_2$O) to afford the amide (2.6 mg, 40%) as a solid. $^1$H NMR (400 MHz, CD$_3$OD) δ 8.70 (d, J=2.3 Hz, 1H), 8.57 (d, J=2.3 Hz, 1H), 7.52 (d, J=8.1 Hz, 1H), 7.35 (d, J=8.1 Hz, 1H), 4.93 (s, 2H), 4.92 (s, 2H, obscured by CD$_3$OH signal), 3.40 (d, J=16.6H, 1H), 3.07-2.94 (m, 2H), 2.78 (d, J=16.6 Hz, 1H), 2.48-2.40 (m, 1H), 2.11-2.03 (m, 1H), 1.57 (s, 6H), 1.46 (s, 3H); m/z=465.0 (M+1)$^+$.

Compound 25

(S)-6-Trifluoromethyl-2,3-dihydro-benzo[1,4]dioxine-2-carboxylic acid 1[(R)-1-(1H-indazol-5-yl)-ethyl]-amide

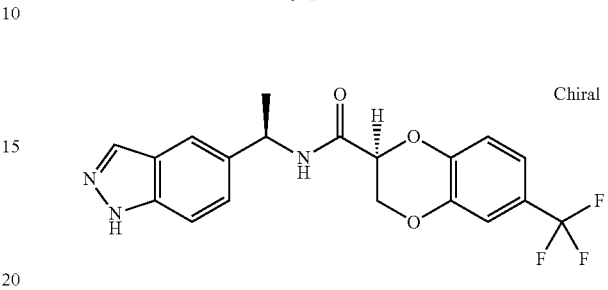

A stirred solution of (S)-6-(trifluoromethyl)-2,3-dihydrobenzo[b][1,4]dioxine-2-carboxylic acid (55 mg, 0.22 mmol) in anhydrous DCM (6 mL) was cooled to 0° C. DMF (1 drop) was added, followed by oxalyl chloride (26 μL, 0.3 mmol). The reaction was allowed to warm to room temperature and stirred for 30 minutes, then evaporated to dryness. A solution of (R)-1-(1H-Indazol-5-yl)ethylamine hydrochloride (40 mg, 0.2 mmol) in acetonitrile (6 mL) was added, followed by N,N-diisopropylethylamine (53 μL, 0.3 mmol), and the reaction was stirred at room temperature for 1 hour. The reaction mixture was poured into saturated NaHCO$_3$ solution (5 mL) and extracted with EtOAc (3×10 mL). The combined organics were washed with brine (2×5 mL), dried (MgSO$_4$), filtered and evaporated to dryness. Flash chromatography (0 to 4% MeOH in DCM over 30 minutes) the product (33 mg) as a solid. $^1$H NMR (400 MHz; DMSO-d$_6$) 13.01 (1H, s), 8.62 (1H, t), 7.92 (1H, d), 7.47-7.36 (3H, m), 7.26-7.18 (3H, m), 7.05 (1H, d), 5.10-5.05 (1H, m), 4.99 (1H, t), 4.41-4.38 (2H, m), 1.45 (3H, d).

Compound 26

(R)-6-Trifluoromethyl-2,3-dihydro-benzo[1,4]dioxine-2-carboxylic acid [(R)-1-(1H-indazol-5-yl)-ethyl]-amide

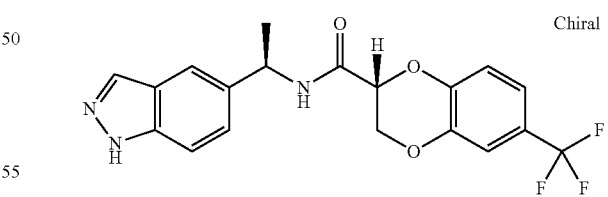

A stirred solution of (R)-6-(trifluoromethyl)-2,3-dihydrobenzo[b][1,4]dioxine-2-carboxylic acid (55 mg, 0.22 mmol) in anhydrous DCM (6 mL) was cooled to 0° C. DMF (1 drop) was added, followed by oxalyl chloride (26 μL, 0.3 mmol). The reaction was allowed to warm to room temperature and stirred for 30 minutes, then evaporated to dryness. A solution of (R)-1-(1H-Indazol-5-yl)ethylamine hydrochloride (40 mg, 0.2 mmol) in acetonitrile (6 mL) was added, followed by N,N-diisopropylethylamine (53 μL, 0.3 mmol), and the reaction was stirred at room temperature for 1 hour.

The reaction mixture was poured into saturated NaHCO$_3$ solution (5 mL) and extracted with EtOAc (3×5 mL). The combined organics were washed with brine (2×5 mL), dried (MgSO$_4$), filtered and evaporated to dryness. Flash chromatography (0 to 4% MeOH in DCM over 30 minutes) gave the product (35 mg) as a solid. $^1$H NMR (400 MHz; DMSO-d$_6$) 13.0 (1H, s), 8.63 (1H, dd), 8.04 (1H, s), 7.69 (1H, s), 7.50 (1H, d), 7.37-7.33 (2H, m), 7.23-7.18 (2H, m), 7.07 (1H, d), 5.09-5.05 (1H, m), 4.93-4.90 (1H, m), 4.47-4.43 (1H, m), 4.35-4.32 (1H, m), 1.43 (3H, d).

General Method for Automated Parallel LC-MS Purification of Libraries

The libraries were purified using a Perkin Elmer API100 mass spectrometer coupled to Shimadzu LC pumps. The chromatographic method employed was 10-100% gradient of acetonitrile to water over 8 minutes at a flow rate of 6 ml per minute. The column used was a 10×50 mm YMC C18 and the compounds were collected using a Gilson 204 fraction collector.

Following the methods described above and the appropriate reagents, starting materials and purification methods known to those skilled in the art, the amide compounds of this invention were or can be prepared.

The synthetic and biological examples presented herein are offered to illustrate this invention and are not to be construed in any way as limiting the scope of this invention. In the examples below, all temperatures are in degrees Celsius (unless otherwise indicated).

The compounds that have been prepared in accordance with the invention are presented in Table 1, below. The syntheses of these representative compounds were carried out in accordance with the methods set forth above, and activity of the compounds was measured by percent inhibition in a calcium uptake assay, the details of which are described below.

Calcium Uptake Assay.

Functional activity of compounds against the VR1 receptor was determined by measuring changes in intracellular calcium in HEK 293 cells expressing hVR1. Compounds were examined for their ability to inhibit agonist-induced calcium influx. Relative levels of [Ca$^{2+}$] were monitored in a 96-well format using a calcium-sensitive fluorescence dye and a FLIPR TETRA, Molecular Devices.

Cell Line and Culture Conditions:

Cells that express high levels of VR1 were obtained by generation of a cell line from human keratinocytes with heterologous expression of VR1 under control of an inducible promoter. Specifically, cells expressing human VR1 under the control of the human cytomegalovirus immediate-early (CMV) promoter and two tetracycline operator 2 (TetO2) sites were made using the T-REx System (Invitrogen, Carlsbad, Calif., USA). Details and methods concerning this system are published (Hum. Gene Ther. 9, pp. 1939-1950, 1998; Annu. Rev. Microbiol. 48, pp. 345-369, 1994; Mol. Biol. 169, pp. 707-'721, 1983). Human VR1 was subcloned into the T-REx System pcDNA5/TO vector (Invitrogen Cat# V1033-20) which was transfected into the T-REx System human keratinocyte cell line (Invitrogen Cat# R710-07) from which a stable cell line was established which expresses VR1 after induction by exposure to tetracycline or doxycycline (Hum. Gene Ther. 9, pp. 1939-1950, 1998; instructions that come with purchase of products noted above). Cells were maintained in a CO$_2$ incubator (5% CO$_2$) at 37° C. in culture medium containing DMEM with phenol red (Mediatech Cat #: 15-017-CV) supplemented with 10% heat-inactivated Fetal Bovine Serum, 5% Penicillin-streptomycin (Mediatech Cat #: 30-002-CI), 5% Glutamax® (L-Alanyl-L-Glutamine, Mediatech Cat #: 25-015-CI), 200 µg/ml hygromycin (Mediatech #:30-240-CR), 0.5 µg/ml blasticidin (Invitrogen #46-1120)).

Determination of IC$_{50}$ Values Against Agonist Stimulation

For assay preparation, cells expressing human VR1 as described above were plated in 96-well plates (Becton Dickinson [BD] poly-D-lysine coated 96-well plates, cat #356692) at 55,000 cells per well in culture media (described above) that also contained 1 ug/ml doxycycline. Plated cells were then placed in an incubator (5% CO$_2$) and incubated for 20-26 hours at 37° C., until the cells had grown to near confluency. Media was then aspirated from cells and 50 uL of dye-containing buffer (from Molecular Devices FLIPR Calcium 4 Assay kit, cat# R8141) was added to each well. Cells were then left in the dark at room temperature for 1.5-2 hours. Cell plates were then placed in the FLIPR TETRA (Molecular Devices, CA, USA). Test compounds and agonists were added to wells using the liquid handling capability of the FLIPR TETRA. Calcium responses of the cells were monitored by fluorescence readout of dye signal. Test compounds in saline (130 mM NaCl, 17 g/L sucrose, 1.8 g/L glucose, 8.8 mM HEPES, 3 mM KCl, 0.60 mM MgCl, 1.0 mM CaCl$_2$; adjust to pH 7.4 using NaOH; 0.03% BSA added on the day of the experiment), or vehicle control in saline, were pre-incubated at the desired final concentrations in the dark at room temperature for 2 or 30 minutes with cells already containing the above mentioned dye buffer (dye solution was diluted 1:1 in culture wells with saline containing 2× the final concentration of test compound). Compound IC$_{50}$ experiments were run using an agonist concentration at or near the EC$_{50}$ of the agonist. One agonist used was capsaicin at a final concentration of either 10 nM or the EC$_{50}$ of capsaicin as determined by running a dose response curve of capsaicin on the day of the experiment (which yielded EC$_{50}$ values ranging between 2.5 nM and 11 nM depending on the day). Another agonist was protons via a low pH solution (saline solution described above plus 10 mM citric acid buffered to pH 5.7 with HCl instead of buffering to a neutral pH with NaOH as done for normal saline). Compounds were tested at various concentration ranges, depending upon potency of compound. After the 2 minute or 30 minute compound pre-treatment, treatment solution was then added to cells by adding a volume of treatment solution equal to the pretreatment solution already on the cells. The treatment solution consisted of the test compound at the same target concentration as in pre-treatment in addition to agonist: either capsaicin at 2× the final desired concentration in saline to yield 1× final when diluted with the solution already in the wells or treatment solution was made without capsaicin and instead compound was appropriately diluted into the saline buffer described above for low pH agonism. Recordings were made to measure the fluorescence signal (λex=470-495 nm, λem=515-575 nm) for at least 2 minutes after agonist addition (enough time for the fluorescence response to reach and then decline from the absolute maximum, agonist-induced signal attained). The percent inhibition value of the test compound at a given concentration tested was calculated as:

$$\% \text{ inhibition} = 100 \times \left[1 - \frac{\left(\frac{\text{Response of Agonist with Compound}-}{\text{Response of Vehicle alone}}\right)}{\left(\frac{\text{Response of Agonist with Vehicle}-}{\text{Response of Vehicle alone}}\right)}\right]$$

Where, response was calculated as the difference between the maximum fluorescence signal obtained after agonist addition and the signal seen at baseline before agonist, but after antagonist, addition (the absolute minimum level of fluorescence signal observed in the 10 seconds prior to agonist addition). $IC_{50}$ values were calculated by curve fitting estimation. Percent inhibition data across the compound concentrations tested were used to create a dose-response curve of the test compound against the agonist. These data were then fit to a 4-parameter sigmoidal curve (variable slope) equation using Graphpad Prism software (by Graphpad Software, San Diego, Calif.): y=Bottom+(Top-Bottom)/(1−10^((log $IC_{50}$−x)*Hillslope), where x=log(concentration). The results obtained with representative compounds of the invention, prepared according to the methods described herein or some modification thereof, are set forth in Table 1, below.

In addition to the compounds exemplified above, various other amide compounds of this invention have been prepared using the procedure and synthetic methods described above, or via routine modification of the methods described here, and the corresponding starting materials, appropriate reagents, and purification methods known to those skilled in the art. Accordingly, the compounds prepared along with their analytical data, are listed in Table 1, below.

TABLE 1

| ID | Structure* | | MW (Calcd) | MW (Obs) | $IC_{50}$ (nM) Capsaicin | $IC_{50}$ (nM) Low pH | pA2 Value |
|---|---|---|---|---|---|---|---|
| 1 | 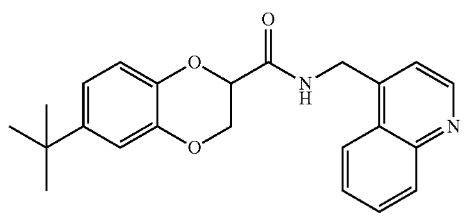 | | 376.45 | 376.6 | 36 | | 240 |
| 2 | 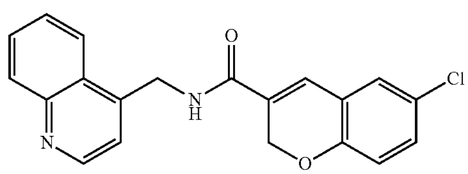 | | 350.8 | 350.8 | 143 | | |
| 3 | 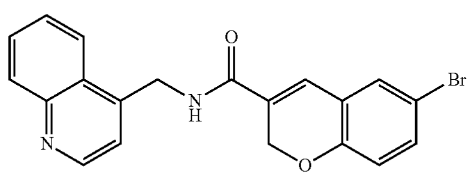 | | 395.25 | 395.3 | 128 | | |
| 4 | 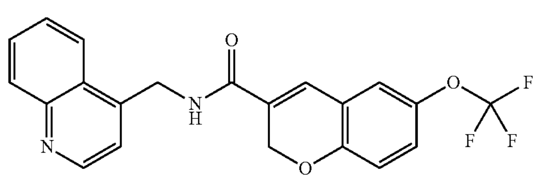 | | 400.35 | 401.4 | 108 | | |
| 5 | 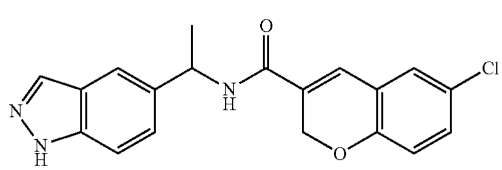 | | 353.81 | 354.3 | | | |
| 6 | 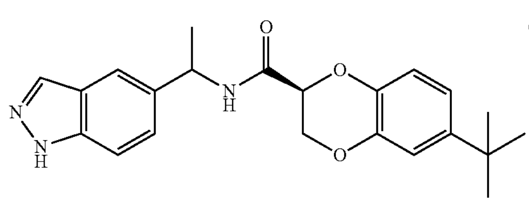 | Chiral | 379.46 | 379.7 | 103 | | |

TABLE 1-continued

AMIDE COMPOUNDS

| ID | Structure* | | MW (Calcd) | MW (Obs) | IC$_{50}$ (nM) Capsaicin | IC$_{50}$ (nM) Low pH | pA2 Value |
|---|---|---|---|---|---|---|---|
| 7 | 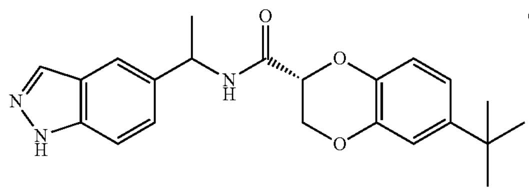 | Chiral | 379.46 | 380.2 | 29 | 226 | 7.794 |
| 8 | 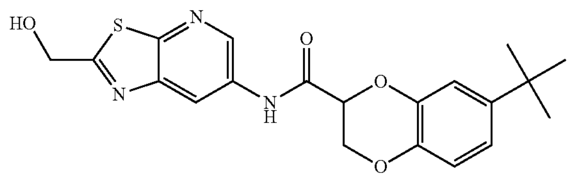 | | 399.47 | 400.5 | | 8 | 7.84 |
| 9 | 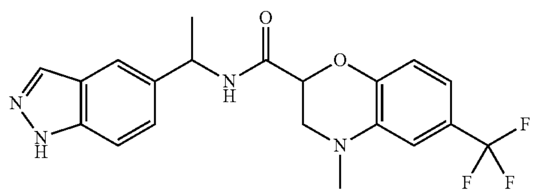 | | 404.39 | 405.5 | 42 | 117 | 7.46 |
| 10 | 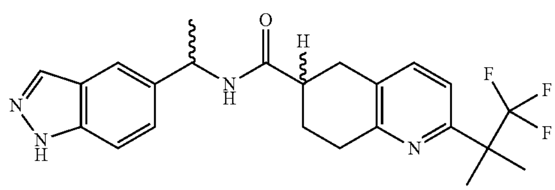 | | 430.47 | 431.4 | 8 | | 8.365 |
| 11 | 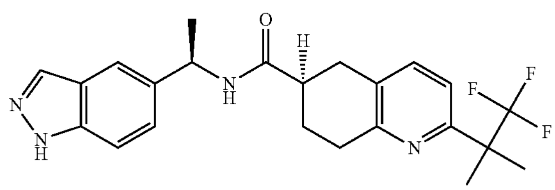 | Chiral | 430.47 | 431.4 | 9 | 23 | 8.747 |
| 12 | 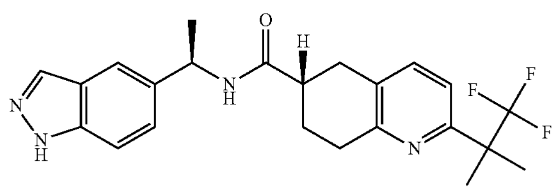 | Chiral | 430.47 | 431.3 | 2 | 6 | 9.682 |
| 13 | 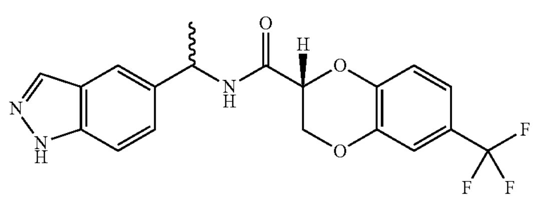 | Chiral | 391.35 | 391.8 | 64 | | 7.427 |

TABLE 1-continued

AMIDE COMPOUNDS

| ID | Structure* | | MW (Calcd) | MW (Obs) | IC$_{50}$ (nM) Capsaicin | IC$_{50}$ (nM) Low pH | pA2 Value |
|---|---|---|---|---|---|---|---|
| 14 | [structure] | Chiral | 391.35 | 392.3 | 820‡ | | |
| 15 | [structure] | Chiral | 450.48 | 451 | 19 | 18 | 8.2966 |
| 16 | [structure] | Chiral | 411.36 | 412.3 | | 571 | 6.375 |
| 17 | [structure] | Chiral | 380.32 | 381.1 | 140 | | |
| 18 | [structure] | Chiral | 419.44 | 420.1 | 6 | 18 | 7.495 |
| 19 | [structure] | Chiral | 419.44 | 420.1 | 9 | 67 | 7.7707 |

TABLE 1-continued

AMIDE COMPOUNDS

| ID | Structure* | | MW (Calcd) | MW (Obs) | IC$_{50}$ (nM) Capsaicin | IC$_{50}$ (nM) Low pH | pA2 Value |
|---|---|---|---|---|---|---|---|
| 20 | 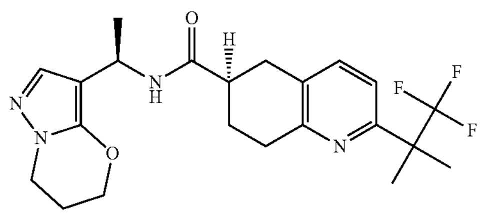 | Chiral | 436.48 | 437.4 | 310 | | |
| 21 | 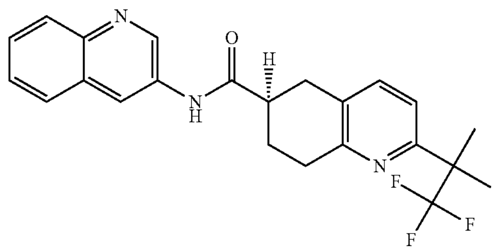 | Chiral | 413.44 | 414.1 | 33 | 40 | 7.641 |
| 22 | 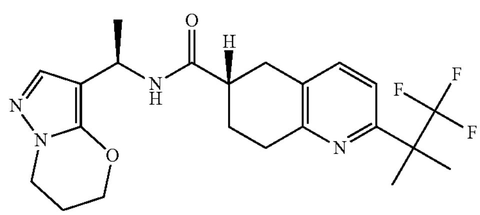 | Chiral | 436.48 | 437.4 | 76 | | 7.2255 |
| 23 | 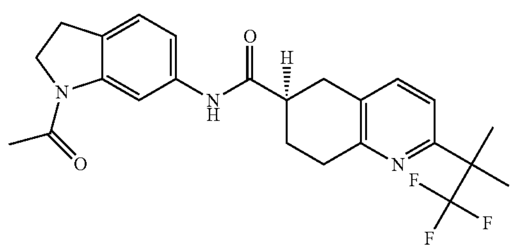 | Chiral | 445.48 | 446.5 | 2 | 9 | 8.2281 |
| 24 | 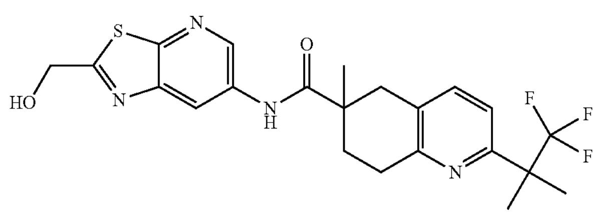 | | 464.51 | 465 | | 121 | 7.16 |
| 25 | 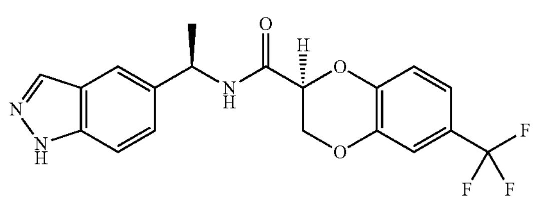 | Chiral | 391.35 | 392.5 | 150 | | 6.725 |

TABLE 1-continued

AMIDE COMPOUNDS

| ID | Structure* | | MW (Calcd) | MW (Obs) | IC$_{50}$ (nM) Capsaicin | IC$_{50}$ (nM) Low pH | pA2 Value |
|---|---|---|---|---|---|---|---|
| 26 | [structure] | Chiral | 391.35 | 392.5 | 93 | | 7.648 |

‡Inhibition of 54% at 1 uM. Higher Concentrations not tested.
*The isomers are purified using the means known to one skilled in the art and the stereochemistry of the isolated isomer is assigned arbitrarily and is not verified.

Determination of pA$_2$ Values Against Capsaicin Stimulation pA$_2$ values of antagonists against the capsaicin agonist dose-response are determined using a Ca$^{2+}$ imaging assay with cells expressing high levels of human VR1 (for explanation of theory behind pA$_2$ determinations, see *A Pharmacological Primer: Theory, Applications, and Methods* 2$^{nd}$ edition by Terry P. Kenakin, pp. 102-108, Academic Press, New York, 2006).

Cell preparation, test compound additions, and capsaicin additions are all performed as mentioned above for the IC$_{50}$ determinations, however instead of running a dose-range of test compound against one concentration of agonist, a dose-range of capsaicin is run against vehicle and a few concentrations of test compound. After test compound addition, capsaicin plus the appropriate concentration of antagonist in saline is added at varying concentrations to achieve final concentrations covering the range of 17 pM-3 uM final capsaicin and the same final concentration of antagonist, or vehicle control, that is already in the well from the antagonist pre-incubation step described above. Changes in the fluorescence signal (λex=470-495 nm, λem=515-575 nm) are monitored throughout the experiment before agonist addition and for at least 2 min after agonist addition (enough time for the fluorescence response to reach and then decline from the absolute maximum, agonist-induced signal attained). For each well, final relative fluorescence units (RFUs) are calculated as the difference between the maximum fluorescence signal obtained in the experiment after agonist addition and the signal level seen at baseline before agonist, but after antagonist, addition (the absolute minimum level of fluorescence signal observed in the 10 seconds prior to agonist addition). These final RFU values are plotted against the corresponding capsaicin concentrations to obtain dose response curves across the capsaicin dose range tested; one dose response curve for each concentration of antagonist tested and one for the capsaicin dose-response without any antagonist (vehicle control). Data are fit to an ideal curve utilizing the 4-parameter sigmoid curve-fit function in Graph-Pad Prism software (version 4, GraphPad Software, Inc., San Diego, Calif., USA) from which an EC$_{50}$ value is obtained. The dose ratio (DR) is then calculated for each concentration of antagonist tested as the ratio of the EC$_{50}$ value of the dose-response curve of capsaicin in the presence of a given concentration of antagonist divided by the EC$_{50}$ value of the dose-response curve of capsaicin without antagonist (vehicle control). For each antagonist, at least three concentrations are tested. Dose Ratio values are then used to make a standard Schild plot—log [antagonist concentration] plotted against log [DR-1], see Kenakin reference above for theoretical background and method. A linear regression curve-fit is then performed on these plotted points. If the linear regression provided an R$^2$ value 0.8 AND there are at least two concentrations of antagonist tested that provided a DR value greater than 1, then pA$_2$ values are calculated and reported as pA$_2$=Log(DR-1)-Log [antagonist] for the lowest concentration of antagonist tested for which (DR-1)>0. If these conditions are not met, then the antagonist is rerun in a pA$_2$ assay using different antagonist concentrations until the above conditions are met.

Half-Life in Human Liver Microsomes (HLM)

Exemplary compounds of the invention are tested (1 μM), and are incubated with 3.3 mM MgCl$_2$ and 0.78 mg/mL HLM (HL101) in 100 mM potassium phosphate buffer (pH 7.4) at 37° C. on the 96-deep well plate. The reaction mixture is split into two groups, a non-P450 and a P450 group. NADPH is only added to the reaction mixture of the P450 group. An aliquot of samples of the P450 group is collected at 0, 10, 30, and 60 minute time points, where the 0 minute time point indicated the time when NADPH is added into the reaction mixture of the P450 group. An aliquot of samples of the non-P450 group is collected at -10 and 65 minute time points. Collected aliquots are extracted with an acetonitrile solution containing an internal standard. The precipitated protein is spun down in a centrifuge (2000 rpm, 15 min). The compound concentration in supernatant is measured by LC/MS/MS system. The half-life value (T$_{1/2}$) is obtained by plotting the natural logarithm of the peak area ratio of compounds/internal standard versus time. The slope of the line of best fit through the points yields the rate of metabolism (k). This is converted to a half-life value using following equations: Half-life=ln 2/k.

Pharmacokinetic Evaluation of Compounds Following Intravenous and Oral Administration in Rats.

Male Sprague-Dawley rats are acclimatized for at least 24 hours prior to experiment initiation. During acclimation period, all animals receive food and water ad libitum. However, food but not water is removed from the animal's cages at least 12 hours before initiation of the experiment. During the first 3 hours of experimentation, the animals receive only water ad libitum. At least three animal each are tested for intravenous and oral dosage. For intravenous formulation, compounds are dissolved (0.25 to 1 mg/mL) in a mixture of 3% dimethyl sulfoxide, 40% PEG 400 and the rest percentage of 40% Captisol in water (w/v). For oral formulation, compounds of this invention are dissolved (2 mg/mL) in a mixture of 5% of 10% Tween 80 in water (v/v) and 95% of 0.5% methyl cellulose in water (w/v). The animals are weighed before dosing. The determined body weight is used to calculate the dose volume for each animal.

For intravenous dosing: Dose volume (mL/kg)=1 mg/kg/formulation concentration (mg/mL).

In instances where the formulation concentrations are less than 0.5 mg/mL, the dosing volume is about 2 mL/kg. PO rats are typically dosed through oral gavage at 2.5 mL/kg to achieve a dose level of 5 mg/kg. For IV dosing, blood samples are collected (using a pre-heparinized syringe) via the jugular vein catheter at 2, 5, 15, 30, 60, 120, 180, 300, 480, and 1440 minutes post dosing. For PO dosing, blood samples are collected (using a pre-heparinized syringe) via the jugular vein catheter before dosing and at 5, 15, 30, 60, 120, 180, 300, 480, and 1440 minutes post dosing. About 250 uL of blood is obtained at each time point from the animal. Equal volumes of 0.9% normal saline are replaced to prevent dehydration. The whole blood samples are maintained on ice until centrifugation. Blood samples are then centrifuged at 14,000 rpm for 10 minutes at 4° C. and the upper plasma layer transferred into a clean vial and stored at −80° C. The resulting plasma samples are then analyzed by liquid chromatography-tandem mass spectrometry. Following the measurement of plasma samples and dosing solutions, plasma concentration-time curve is plotted. Plasma exposure is calculated as the area under the concentration-time curve extrapolated to time infinite ($AUC_{inf}$). The $AUC_{inf}$ is averaged and the oral bioavailability (% F) for individual animal is calculated as:

AUCinf(IV,average)/AUCinf(PO), normalized to their respective dose levels.

The % F is reported as the mean % F of all oral dosed animals.

Example 1

Calcium Imaging Assay

VR1 protein is a heat-gated cation channel that exchanges approximately ten calcium ions for every sodium ion resulting in neuronal membrane depolarization and elevated intracellular calcium levels. Therefore the functional activity of compounds at the VR1 receptor may be determined by measuring changes in intracellular calcium levels in neurons such as the dorsal root ganglion.

DRG neurons are grown on PDL coated 96-well black-walled plates, in the presence of DMEM medium containing 5% Penstrep, 5% Glutamax, 200 µg/ml hygromycin, 5 µg/ml blasticide and 10% heat inactivated FBS. Prior to assay, cells are loaded with 5 µg/ml Fura2 in normal saline solution at 37° C. for 40 minutes. Cells are then washed with normal saline to remove dye before commencement of the experiment.

The plated neurons are transferred into a chamber on the stage of a Nikon eclipse TE300 microscope after which neurons are allowed to attain a stable fluorescence for about 10 minutes before beginning the experiment. The assay consists of two stages, a pretreatment phase followed by a treatment phase. First, a solution of the test compound is added from a multivalve perfusion system to the cells for 1 minute (pretreatment). Immediately following, capsaicin (250 nM) is added in the presence of the test compound (treatment) for a specific period between 20 and 60 seconds.

Fura2 is excited at 340 and 380 nM to indicate relative calcium ion concentration. Changes in wavelength measurements are made throughout the course of the experiment. The fluorescence ratio is calculated by dividing fluorescence measured at 340 nM by that at 380 nM. Data are collected using Intelligent Imaging's Slidebook software. All compounds that inhibit capsaicin induced calcium influx greater than 75% are considered positives.

Example 2

High Throughput Analysis of VR1 Antagonists for Determination of In Vitro Efficacy Using a Calcium Imaging Assay Inhibition of the capsaicin response in the presence and absence of the test compound was measured and assessed, using the method for calcium uptake assay, described hereinabove with respect to the data presented in Table 1. No such reduction in response is observed in the absence of the test compound.

Example 3

Whole-Cell Patch Clamp Electrophysiology

Dorsal root ganglion (DRG) neurons are recovered from either neonatal or adult rats and plated onto poly-D-lysine coated glass coverslips. The plated neurons are transferred into a chamber to allow drug solutions to be added to the cells using a computer-controlled solenoid-valve based perfusion system. The cells are imaged using standard DIC optics. Cells are patched using finely-pulled glass electrodes. Voltage-clamp electrophysiology experiments are carried out using an Axon Instruments Multiclamp amplified controlled by pCLAMP8 software.

The cells are placed into a whole-cell voltage clamp and held at a voltage of −80 mV while monitoring the membrane current in gap-free recording mode. 500 nM capsaicin is added for 30 seconds as a control. Test compounds at various concentrations are added to the cells for 1 minute prior to a 30 second capsaicin application. Differences between control experiments and drug positive capsaicin experiments are used to determine the efficacy of each test compound. All compounds that inhibit capsaicin induced current greater than 50% are considered positives.

All publications, patents and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims All such modifications coming within the scope of the appended claims are intended to be included therein.

In general, the nomenclature used in this application is based on AUTONOM™ v.4.0, a Beilstein Intitute computerized system for the generation of IUPAC systematic nomenclature. Chemical structures shown herein were prepared using ISIS®/DRAW version 2.5. Any open valency appearing on a carbon, oxygen or nitrogen atom in the structures herein indicates the presence of a hydrogen atom. Where a chiral center exists in a structure but no specific stereochemistry is shown for the chiral center, both enantiomers associated with the chiral structure are encompassed by the structure.

The chemical names of compounds given in this application were generated using Open Eye Software's Lexichem naming tool, Symyx Renaissance Software's Reaction Planner or MDL's ISIS Draw Autonom Software tool, and are not verified. Preferably, in the event of inconsistency, the depicted structure governs.

What is claimed is:

1. A compound selected from
   2-(2,2,2-Trifluoro-1,1-dimethyl-ethyl)-5,6,7,8-tetrahydro-quinoline-6-carboxylic acid[1-(1H-indazol-5-yl)-ethyl]-amide;
   (R)-2-(2,2,2-Trifluoro-1,1-dimethyl-ethyl)-5,6,7,8-tetrahydro-quinoline-6-carboxylic acid [(R)-1-(1H-indazol-5-yl)-ethyl]-amide; and
   (S)-2-(2,2,2-Trifluoro-1,1-dimethyl-ethyl)-5,6,7,8-tetrahydro-quinoline-6-carboxylic acid [(R)-1-(1H-indazol-5-yl)-ethyl]-amide;
   or a pharmaceutically acceptable salt thereof, and isotopic variants thereof, stereoisomers and tautomers thereof.

2. A pharmaceutical composition comprising a pharmaceutically acceptable carrier and a pharmaceutically effective amount of a compound of claim 1.

3. A method for treating a disease or condition which comprises administering to a patient in need of a therapeutically acceptable amount of a compound of claim 1, or a pharmaceutical composition of claim 2, wherein the disease is: pain including acute, inflammatory and neuropathic pain; chronic pain; dental pain; headache including migraine, cluster headache and tension headache.

4. The method of claim 3 wherein the disease or condition is neuropathic pain.

5. The method of claim 3 wherein the pain is associated with a condition selected from the group consisting of post-mastectomy pain syndrome, stump pain, phantom limb pain, oral neuropathic pain, Charcot's pain, toothache, venomous snake bite, spider bite, insect sting, postherapeutic neuralgia, diabetic neuropathy, reflex sympathetic dystrophy, trigeminal neuralgia, osteoarthritis, rheumatoid arthritis, fibromyalgia, Guillain-Barre syndrome, meralgia paresthetica, burning-mouth syndrome, bilateral peripheral neuropathy, causalgia, sciatic neuritis, peripheral neuritis, polyneuritis, segmental neuritis, Gombault's neuritis, neuronitis, cervicobrachial neuralgia, cranial neuralgia, egniculate neuralgia, glossopharyngial neuralgia, migranous neuralgia, idiopathic neuralgia, intercostals neuralgia, mammary neuralgia, mandibular joint neuralgia, Morton's neuralgia, nasociliary neuralgia, occipital neuralgia, red neuralgia, Sluder's neuralgia, splenopalatine neuralgia, supraorbital neuralgia, vidian neuralgia, sinus headache, tension headache, labor, childbirth, intestinal gas, menstruation, cancer, and trauma.

* * * * *